United States Patent
Atala et al.

(10) Patent No.: US 8,940,292 B2
(45) Date of Patent: Jan. 27, 2015

(54) ENHANCEMENT OF ANGIOGENESIS TO GRAFTS USING CELLS ENGINEERED TO PRODUCE GROWTH FACTORS

(75) Inventors: Anthony Atala, Winston-Salem, NC (US); Shay Soker, Greensboro, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 634 days.

(21) Appl. No.: 10/766,642

(22) Filed: Jan. 28, 2004

(65) Prior Publication Data
US 2005/0002915 A1 Jan. 6, 2005

Related U.S. Application Data

(60) Provisional application No. 60/443,129, filed on Jan. 28, 2003.

(51) Int. Cl.
*A61L 27/38* (2006.01)
*A61K 48/00* (2006.01)
(Continued)

(52) U.S. Cl.
CPC ............. *A61L 27/3886* (2013.01); *A61K 48/00* (2013.01); *A61L 27/3808* (2013.01); *A61L 27/3834* (2013.01); *C12N 5/0658* (2013.01); *C12N 5/0686* (2013.01); *C12N 5/0697* (2013.01); *A61K 38/1866* (2013.01); *A61K 35/34* (2013.01); *A61K 35/44* (2013.01); *A61K 35/12* (2013.01); *C12N 2501/165* (2013.01);
(Continued)

(58) Field of Classification Search
CPC .................................................. A61L 27/3886
USPC ......... 435/375, 325, 347, 366, 374, 395, 459, 435/455; 424/422, 93.7; 604/890.1
See application file for complete search history.

(56) References Cited

U.S. PATENT DOCUMENTS

| | | | |
|---|---|---|---|
| 1,995,970 A | 3/1935 | Dorough | |
| 2,676,945 A | 4/1954 | Higgins | |

(Continued)

FOREIGN PATENT DOCUMENTS

| WO | 9819712 A1 | 5/1998 | |
|---|---|---|---|
| WO | WO 98/19712 | * 5/1998 | ............. A61K 48/00 |

(Continued)

OTHER PUBLICATIONS

Lazarous et al, Cardiovascular Research, 1999, vol. 44, pp. 294-302.*
(Continued)

*Primary Examiner* — Allison Fox
(74) *Attorney, Agent, or Firm* — Thomas Engellenner; Reza Mollaaghababa; Pepper Hamilton LLP

(57) ABSTRACT

The present invention provides methods and compositions of engineered cells for use in the continuous or transient delivery of growth factors and angiogenesis modulating agents, such as vascular endothelial growth factor (VEGF), in conjunction with constructs for replacing or augmenting organ functions. In one aspect of the invention, the genetically engineered cells can be immature cells that are capable of differentiating and assimilating into the target region. The methods of the present invention can be used to enhance vascularization locally at a target site in need of repair, growth, or implantation through the incorporation of autologous cells which have been genetically engineered to secrete a growth factor or angiogenesis modulating agent.

27 Claims, 9 Drawing Sheets

(51) Int. Cl.
  *C12N 5/077* (2010.01)
  *C12N 5/071* (2010.01)
  *A61K 38/18* (2006.01)
  *A61K 35/34* (2006.01)
  *A61K 35/44* (2006.01)
  *A61K 35/12* (2006.01)

(52) U.S. Cl.
  CPC ... *C12N2502/1347* (2013.01); *C12N 2502/253* (2013.01); *C12N 2502/28* (2013.01); *C12N 2502/99* (2013.01); *C12N 2533/32* (2013.01); *C12N 2533/52* (2013.01); *C12N 2533/54* (2013.01); *C12N 2533/72* (2013.01); *C12N 2533/90* (2013.01)
  USPC ..................... 424/93.7; 424/93.21; 424/423

(56) References Cited

U.S. PATENT DOCUMENTS

| | | | |
|---|---|---|---|
| 2,683,136 A | 7/1954 | Higgins | |
| 2,703,316 A | 3/1955 | Schneider | |
| 2,758,987 A | 8/1956 | Salzberg | |
| 2,951,828 A | 9/1960 | Zelle et al. | |
| 3,531,561 A | 9/1970 | Trehu | |
| 4,251,387 A | 2/1981 | Lim et al. | |
| 5,266,480 A | 11/1993 | Naughton et al. | |
| 5,514,378 A | 5/1996 | Mikos et al. | |
| 5,654,273 A | 8/1997 | Gallo et al. | |
| 5,709,854 A * | 1/1998 | Griffith-Cima et al. | 424/93.7 |
| 5,738,876 A | 4/1998 | Enevold | |
| 5,785,964 A | 7/1998 | Naughton et al. | |
| 5,851,833 A | 12/1998 | Atala | |
| 5,855,610 A | 1/1999 | Vacanti et al. | |
| 5,858,721 A | 1/1999 | Naughton et al. | |
| 5,891,477 A * | 4/1999 | Lanza et al. | 424/501 |
| 6,140,039 A | 10/2000 | Naughton et al. | |
| 6,165,487 A | 12/2000 | Ashkar et al. | |
| 6,171,344 B1 | 1/2001 | Atala | |
| 6,297,221 B1 * | 10/2001 | Parmacek et al. | 514/44 |
| 6,376,244 B1 | 4/2002 | Atala | |
| 6,383,478 B1 | 5/2002 | Prokop et al. | |
| 6,428,802 B1 | 8/2002 | Atala | |
| 6,432,081 B1 | 8/2002 | Atala | |
| 6,479,064 B1 | 11/2002 | Atala | |
| 6,482,645 B2 | 11/2002 | Atala | |
| 6,519,492 B1 | 2/2003 | Yoo et al. | |
| 6,569,428 B1 | 5/2003 | Isner et al. | |
| 6,576,019 B1 | 6/2003 | Atala | |
| 6,620,203 B2 | 9/2003 | Atala | |
| 6,673,339 B1 | 1/2004 | Atala et al. | |
| 6,692,738 B2 * | 2/2004 | MacLaughlin et al. | 424/93.21 |
| 6,753,181 B2 | 6/2004 | Atala | |
| 2003/0007954 A1 * | 1/2003 | Naughton et al. | 424/93.7 |
| 2003/0119714 A1 | 6/2003 | Naylor et al. | |
| 2003/0216811 A1 * | 11/2003 | Badylak | 623/17.16 |
| 2004/0161412 A1 * | 8/2004 | Penn et al. | 424/93.7 |
| 2005/0050228 A1 | 3/2005 | Perham et al. | |
| 2006/0251630 A1 * | 11/2006 | Stewart et al. | 424/93.21 |

FOREIGN PATENT DOCUMENTS

| | | | | |
|---|---|---|---|---|
| WO | WO 01/86893 | * | 11/2001 | A61L 26/00 |
| WO | WO 02/073187 | | 9/2002 | |

OTHER PUBLICATIONS

ATCC Catalog Detail http://www.atc.org/SearchCatalogs/longview.cfm?view=ce,6466490,TIB-192&text=M1&max=20 accessed Jan. 7, 2005.*
Lee et al, Circulation, 2000, vol. 102, p. 898-901.*
Yla et al, Lancet, 2000, vol. 355, pp. 213-222.*
Springer et al, Molecular Cell, 1998, vol. 2, p. 549-558.*
Springer et al, J Gene Med, 2000, vol. 2, p. 279-288.*
U.S. Appl. No. 60/405,274, filed Aug. 22, 2002 by Penn et al.*
U.S. Appl. No. 60/424,065, filed Nov. 6, 2002, by Askari et al.*
Meana et al, Burns, 1998, vol. 24, pp. 621-630.*
Lu et al, Circulation, 2001, vol. 104, pp. 594-599.*
Rinsch et al, Gene Therapy, 2001, vol. 8, Issue 7, pp. 523-533.*
Badylak et al, "Endothelial cell adherence to small intestinal submucosa: an acellular bioscaffold" Biomaterials (1999) 20:2257-2263.*
Losordo et al, "Gene Therapy for Myocardial Angiogenesis: Initial Clinical Results With Direct Myocardial Injection of phVEGF165 as Sole Therapy for Myocardial Ischemia" Circulation (1998) 98:2800-2804.*
Cima, L.G. et al. "Tissue Engineering by Cell Transplantation Using Degradable Polymer Substrates", Journal of Biomechanical Engineering vol. 113, p. 143-151 (1991).
Lanza, Robert P. et el. "Generation of Histocompatible Tissues Using Nuclear Transplantation" Nature Biotechnology. vol. 20, p. 689-696 (2002).
Schuch, Gunter et al. "In Vivo Administration at Vascular Endothelial Growth Factor (VEGF) and Its Antagonist, Soluble Neuropilin-1, Predicts a Role of VEGF in The Progression of Acute Myeloid Leukemia in Vivo", Blood, vol. 100, No. 13, p. 4622-46282 (2002).
Kaushal, S. et al., Nat Med, 2001, 7(9): p. 1035-40.
L'Heureux, N. et al., Nat Med, 2006, 12(3): p. 361-5.
Niklason, L et al., Science, 1999, 284(5413): p. 489-93.
Niklason, L. et al., Transpl Immunol, 1997, 5(4): p. 303-6.
Ingram, D.A. et al., Blood, 2004, 104(9): p. 2752-60.
Korbling, M. et al., Transfusion, 2006, 46(10): p. 1795-802.
Powell, T.M. et al., Arterioscler Thromb Vasc Biol, 2005, 25(2): p. 296-301.
Michon, B. et al., Transfusion, 2007, 47(10): p. 1837-42.
Winters, J.L., J Clin Apher, 2006, 21(2): p. 132-41.
Gehling, U.M. et al., J Hepatol, 2005, 43(5): p. 845-53.
Tondreau, T. et al., Stem Cells, 2005, 23(8): p. 1105-12.
Yin, A.H. et al., Blood, 1997, 90(12): p. 5002-12.
Hill, J.M. et al., N Engl J Med, 2003, 348(7): p. 593-600.
Michaud, S.E. et al., Atherosclerosis, 2006, 187(2): p. 423-32.
Freshney, Culture of Animal Cells. A Manual of Basic Technique, 2d Ed., A. R. Liss, Inc., New York, 1987, Ch. 9, pp. 107B126, Ch. 11 and 12, pp. 137B168.
Geoddel, Gene Expression Technology: Methods in Enzymology 185, Academic Press, San Diego, CA (1990).
Sambrook et al., Molecular Cloning: A Laboratory Manual, 2nd Edition, Cold Spring Harbor Laboratory press (1989).
McCutcheon's, Emulsifiers and Detergents, 1986, North American and International Editions, McCutcheon Division, MC Publishing Co., Glen Rock, N.J., U.S.A.
Judith Neugebauer, A Guide to the Properties and Use of Detergents in Biology and Biochemistry, Calbiochem, Hoechst Celanese Corp., 1987.
Kirker-Head, C.A., Vet. Surg. 24 (5): p. 408-19 (1995).
Bivalacqua, Am J Physiol Heart Circul Physiol, 292, 2006, pp. 1278-1290.

* cited by examiner

ENHANCEMENT OF ANGIOGENESIS TO GRAFTS USING CELLS ENGINEERED TO PRODUCE GROWTH FACTORS

PRIORITY

This application claims priority to U.S. provisional application Ser. No. 60/443,129 filed Jan. 28, 2003.

FIELD OF THE INVENTION

The present invention concerns genetically engineering cells to secrete growth factors and/or angiogenesis modulating agents and methods of enhancing angiogenesis of implanted organ constructs or implanted cultured cell populations.

BACKGROUND OF THE INVENTION

Injury, congenital abnormalities, disease and aging result in disorders of organs and tissues. Organ transplantation yields a high risk of rejection, even with a good histocompatibility match. Immunosuppressive drugs such as cyclosporin and FK506 are usually given to the patient to prevent rejection. However, these immunosuppressive drugs have a narrow therapeutic window between adequate immunosuppression and toxicity. Prolonged immunosuppression can weaken immune systems, which can lead to a threat of infections developing. In some instances, even immunosuppression is not enough to prevent organ rejection. Therefore, current reconstruction techniques prefer using native tissues from multiple body sites. Nonetheless, many complications are associated with the use of native non-autologous tissues.

In an attempt to avoid these problems various methods have been reported in which the patients own autologous cells have been cultured in vitro. For example, U.S. Pat. No. 5,429,938 issued to Humes, describes a method of reconstructing renal tubules using cultured kidney cells. The reconstructed renal tubules can be implanted into the patient.

Naughton et al. disclosed a three-dimensional tissue culture system in which stromal cells are laid over a polymer support system (see U.S. Pat. No. 5,863,531) and parenchyma cells are cultured on the stromal matrix. Vacanti et al. have also disclosed methods for culturing cells in a three-dimensional matrix made of a biodegradable polymer.

A current barrier in the formation of tissues is an adequate vascular supply. Because the nutrition to the cells by diffusion can only penetrate the surface of tissues, neovascularization is a requirement for any solid tissue larger than a few cubic millimeters (Mooney et al. (1999) *Sci Am.* 280(4):60-65). Cells within a bioengineered organ or at the center of an injected cell mass need an extensive blood vessel network to supply nutrients and oxygen and remove waste products. Many techniques have been used to attempt to circumvent this obstacle. Cells have been seeded and grown on micro-porous frameworks as well as scaffolds etched with mini networks imitating vascular systems. However, the slow process of native blood vessels naturally invading the transplanted tissue is not always sufficient for adequate graft survival.

There exists a need for better methods and compositions capable of increasing and stimulating rapid vascularization into a surgical site. In particular, new compositions capable of modulating angiogenesis and stimulating tissue formation would satisfy a long-felt therapeutic need.

SUMMARY OF THE INVENTION

The present invention provides methods and compositions of engineered cells for use in the continuous or transient delivery of growth factors and angiogenesis modulating agents in conjunction with constructs for replacing or augmenting organ functions. In one aspect of the invention, the genetically engineered cells are cells which form an organ construct. The methods of the present invention can be used to enhance vascularization locally at a target site in need of repair, growth, or implantation through the incorporation of autologous cells which have been genetically engineered to secrete a growth factor or angiogenesis modulating agent. The engineered cells can be seeded onto a polymeric scaffold or can be suspended in a biodegradable, natural or polymer matrix, such as collagen, which can be injected at the target site such that the growth factor secreting cells are able to assimilate and differentiate into the growing tissue.

In another aspect, the genetically engineered cells can be used in tandem with an implanted organ construct or at a site where tissue formation is desired. For example, the genetically engineered cells can then be implanted into a subject such that angiogensis modulating agents are secreted locally at the site of organ implantation. The present invention can also be used to enhance the vascularization of an implanted seeded matrix composition allowing the implant to develop into an organ-supplementing structure in vivo. When implanted in vivo, the engineered cells produce vascularization enhancing effects of the implanted cells or organ construct. The genetically engineered cells can again be suspended in a pharmaceutically acceptable carrier, which in this instance can include microcapsules, such as alginate-PLL capsules, which protect the encapsulated cells from the host immune system, while allowing the release of the growth factor, such as VEGF (vascular endothelial growth factor).

In one embodiment, cells can be engineered to constitutively secrete the angiogenesis modulating agent. In another embodiment, cells can be engineered to transiently secrete the angiogenesis modulating agent. In one embodiment, the growth factor is vascular endothelial growth factor (VEGF). In another embodiment, the growth factor is selecting from the group consisting of VEGF, acidic and basic fibroblast growth factors (FGF), epidermal growth factor (EGF), platelet derived growth factor (PDGF), platelet derived endothelial cell growth factor (PD-ECGF), transforming growth factors-beta (TGF-beta), transforming growth factor-alpha (TGF-α), insulin-like growth factors (IGF), erythropoietin (Epo), tumor necrosis factor-alpha (TNF-α), tumor necrosis factor-beta (TNF-β), interferon-γ (INF-γ), and colony stimulating factors (CSFs), angiopoietin, interleukin-8, growth hormone, or variants thereof. In yet another embodiment, the angiogenesis modulating agent is a growth factor.

In one embodiment, the cells are isolated from a subject and cultured in vitro. The cells can be selected from the group consisting of kidney cells, endothelial cells, heart cells, liver cells, pancreatic cells, spleen cells, urothelial cells, mesenchymal cells, smooth muscle cells, skeletal muscle cells, myocytes, myoblasts, cardiac muscle cell, fibroblasts, chondrocytes, adipocytes, fibromyoblasts, and ectodermal cells, hepotocytes, epithelial cells, mesodermal cells, dermal cells, bladder cell, ureteral cell, gonadal cell, parenchymal cell, intestinal cells, and parenchymal cells, bone cells, osteoblasts, osteocytes, nerve cell, hematopoietic stem cell, embryonic stem cell, gastrointestinal mucosal cells, hepatic cells, and sinusoidal capillary cells. In one embodiment, the cell is an immature cell. In another embodiment, the cell is a fibroblast. In a preferred embodiment, the cell is a myoblast.

In one aspect of the invention, allogenic or autologous cells are genetically engineered to produce a growth factor or angiogenesis modulating agent by transfecting the cells with the cDNA of the agent or growth factor of choice. In a preferred embodiment, the cells are immature cells. The transfected immature cells can differentiate and assimilate into the target area. Alternatively, the transfected cells can transiently produce the angiogensis modulating agent and a second population of cells, i.e., immature cells, can be co-administered at the target region. The second population of cells will assimilate into the target region. In one embodiment, the genetically engineered cells can then suspended in a pharmaceutically acceptable carrier which is a biodegradable, natural or polymer matrix. The cell suspension can be injected at the target site such that the growth factor secreting cells are able to assimilate and differentiate into the growing tissue. In a preferred embodiment, the pharmaceutical acceptable carrier comprises collagen. In another embodiment, the genetically engineered cells can be cultured onto a biomatrix which can be implanted in vivo to form an organ construct.

In yet another aspect of the invention, the isolation and genetic engineering of satellite cells was combined with tissue transplantation allowing for transient VEGF expression in skeletal muscle formation in vivo.

In one embodiment of the invention, the angiogenesis modulating agent secreting genetically engineered cells suspended in a pharmaceutically acceptable carrier can be used clinically in urologic reconstructive surgery. In another embodiment, the compositions and methods of the present invention can be used for other therapeutic applications, including but not limited to, wound healing, ischemic diseases, such as renovascular abnormalities, and erectile dysfunction. In wound healing, normal repair includes a rigorous angiogenic response which delivers nutrients and inflammatory cells to the injured tissue. This process facilitates the removal of debris and assists in the development of granulation tissue for wound closure. Delivery of the genetically engineered cells and the resultant production of the growth factor at the wounded area will accelerate angiogenesis and wound healing. In one embodiment, the cells are encapsulated preventing incorporation into the wound site. In another embodiment, the cells are suspended in a biodegradable, nature, or polymer matrix and can assimilate into the wound area. In yet another embodiment, the angiogenesis modulating agent can be induced through the incorporation of an inducible promoter.

In another aspect of the invention, the cells, which are genetically engineered to produce angiogenesis modulating factors are encapsulated. In one embodiment, encapsulation involves the use of microspheres, which allow nutrients to reach the immunoprotected cells, while the angiogenesis modulating agent proteins secreted from the cells diffused into the surrounding tissues. The microspheres protect the coated cells from the host immune environment. In one embodiment, the pharmaceutical acceptable carrier comprises alginate-PLL capsules.

In one aspect of the invention, genetically engineering cells that secret VEGF are encapsulated in alginate microspheres are then implanted into a host at a graft site to enhance angiogenesis. The release of VEGF can stimulate endothelial cell migration, cluster formation and newly formed capillaries at the implant sites.

In another aspect of the invention, encapsulated cells can be supplied to a surgical site inducing rapid formation of new blood vessels and capillaries capable of invading the native or engineered tissues. VEGF is a proangiogenic factor known to act specifically on endothelial cells. In one embodiment, the encapsulated cells of this invention are used to enhance vascularization of implanted organ constructs. In another embodiment, the encapsulated cells enhance vascularization at any surgical site. In yet another embodiment, the encapsulated cells can be used to enhance vascularization of the heart.

In one aspect of the invention, therapeutic angiogenesis is induced through the delivery of the encapsulated growth factor secreting cells at a site in need of repair. In one embodiment, new collateral blood vessels can be induced to the myocardium in order to achieve localized restoration of blood flow. The compositions and methods of the present invention are useful in a large number of disorders including heart disease, stroke, tissue inflammation, ulcerative conditions, arthritis, asthma, tumor growth, diabetic retinopathy, and other ischemic disorders.

In yet another embodiment, the degree of angiogenesis modulating agent secretion and the period of delivery can be regulated by modulating the number of engineered cells which are encapsulated per microsphere, as well as the number of microspheres injected. For example, ischemic disease may require a more prolonged delivery of VEGF than a wound healing application. Dosing schedules can be manipulated using the methods of the present invention. In a preferred embodiment, transient and local VEGF can be administered to promote localized angiogenesis with minimal systemic side effects.

The present invention also provides methods and compositions for augmenting organ functions using small-scale matrix implants generated by seeding tissue-specific or undifferentiated cells onto a matrix materials (e.g., a wafer, sponge, or hydrogel). The seeded matrix composition can then be cultured in vitro to form a three-dimensional biomatrix in which the cells have grown to produce a tissue layer that is capable of developing into a neomophic organ augmenting structure. Once implanted, the three-dimensional biomatrix develops and proliferates at one or more target site in the organ to augment organ function at the site(s). In one aspect of the invention, a population of the undifferentiated cells which are used to seed the matrix can be genetically engineered to secrete a growth factor or angiogenesis modulating agent. In one embodiment, the genetically engineered cells produce the growth factor or angiogenesis modulating agent transiently. In another aspect of the invention, genetically engineered cells are suspended in a pharmaceutically acceptable carrier and implanted with the seeded matrix. In one embodiment, the pharmaceutically acceptable carrier encapsulates the cell while allowing secretion of the angiogenesis modulating agent. In another embodiment, the pharmaceutically acceptable carrier is a biodegradable, nature, or polymer matrix, which allows the genetically engineered cells to assimilate into the target tissue.

In one aspect of the invention artificial organ constructs are disclosed for augmenting function of an organ comprising: a three-dimensional biomatrix formed by perfusing a matrix material with at least one population of cultured cells, such that the cells attach to the matrix material and produce a tissue layer capable of augmenting organ function e.g., to augment an organ such as the heart, kidney, liver, pancreas, spleen, bladder, ureter or urethra.

In another aspect of the invention the augmenting organ structure is a kidney function augmenting structure comprising: a three-dimensional biomatrix formed by perfusing a matrix material with a population of renal cells, such that the renal cells attach to the matrix and produce a tissue layer that differentiates into a nephron structure, or a part of a nephron structure, thereby augmenting kidney function. In one embodiment, a group of cells from the population of renal cells used to seed the matrix have been genetically engineered to stably or transiently produce an angiogenesis modulating agent. These genetically engineered cells can be incorporated into the newly formed tissue layer. In another embodiment, a separate population of renal cells are genetically engineered to stably or transiently produce an angiogenesis modulating agent, encapsulated within a pharmaceutically acceptable carrier, and then co-implanted with the three-dimensional biomatrix.

In yet another aspect of the invention, the matrix has been initially perfused with a population of endothelial cells genetically engineered to stably or transiently produce an angiogenesis modulating agent, such that the endothelial cells attach to the matrix material to produce an endothelial tissue layer comprising a vascular system, followed by seeding with a second population of cells, such that the second cell population attaches to the endothelial tissue layer comprising the vascular system and differentiates to augment organ function.

In one aspect, the invention is drawn to augmenting organ function without replacing the entire organ, or reconstructing the entire organ. For example, to augment kidney function, a small biopsy can be taken from the kidney and the renal cells then expanded in vitro. The cells are sorted to remove damaged cells. A population of the normal cells are genetically engineered to stably or transiently secrete a growth factor or angiogenesis modulating factor. The normal cells and genetically engineered cells can be placed on a matrix (e.g., EGA wafer, sponge, hydrogel) and cultured. The matrix is then cultured until the cells produce a renal tissue layer that is capable of differentiating into a neomorphic organ structure to produce a biomatrix. The biomatrix is then implanted back into the patient, either into desired locations within the kidney, or near the urinary tract (e.g., close to the ureters or bladder).

All kidney cells types can be isolated, i.e., proximal tubules, glomeruli, distil tubules and collecting ducts. The cells can be seeded separately or together. When the cells are seeded together, it may be desirable to seed different types of cells sequentially onto the matrix, or in other instances, various cell types can be seeded together. The mixture of cells will regenerate into kidney tissue in a few weeks after implantation.

In one embodiment of the invention, the kidney cells are placed on wafers of a polymer material, such as ethyl glycol acetate (EGA) or decellularized tissue. The wafers can be placed in any configuration suitable for implantation into a localized region, e.g., can be rolled, can be flat, etc. In one embodiment, the wafer can be placed in one location of the organ, e.g., a kidney. In another embodiment, a number of wafers can be placed at different locations in the organ.

In one preferred embodiment, the matrices are miniaturized for greater ease of implantation. In many applications mini-matrices are desirable having sizes in which the greatest dimension is on the order of 50 millimeters or less, preferably 25 millimeters or less, and most preferably 10 millimeters or less. For example, polymeric wafers can have dimensions of about 2-5 mm, preferably about 2-3 mm. The wafers preferably are thin enough to allow vascularity to occur between the cells on the wafers and those of the surroundings. In one embodiment, the matrix can be seeded with genetically engineered cells capable of stably or transiently producing growth factors or angiogenesis modulating agents.

During in vitro growth, the cells develop and produce a tissue layer which envelopes the matrix material. The tissue layer is capable of developing into a neomorphic organ augmenting structure and supports the growth and development of additional cultured cell populations. In one embodiment, the tissue layer can be derived from renal cells. In another embodiment, the tissue layer can be derived from genetically engineered renal cells capable of constitutively or transiently producing an angiogenesis modulating agent. In another embodiment, the tissue layer can be derived from endothelial cells that that develop to produce a primitive vascular system. In yet another embodiment, the tissue layer can be derived from genetically engineered endothelial cells capable of constitutively or transiently producing an angiogenesis modulating agent. This primitive vascular system can continue to grow and develop, and further support the growth of other parenchyma cells.

In one embodiment, the augmentation target is an organ selected from the group consisting of heart, kidney, liver, pancreas, spleen, bladder, ureter and urethra. In another embodiment, the augmentation target is a part of an organ selected from the group consisting of heart, kidney, liver, pancreas, spleen, bladder, ureter and urethra. In a preferred embodiment, the target organ is a kidney.

In another aspect, the invention features a method for reconstructing an artificial kidney construct comprising seeding tissue-specific or undifferentiated cells which have been genetically engineered to produce a growth factor or angiogenesis modulating agent onto a matrix material, such as a wafer, sponge, or hydrogel), such that cells attach to the matrix; culturing the cells in and on the matrix until the cells produce a tissue structure; and implanting the seeded matrix at a target site for organ augmentation in vivo.

DETAILED DESCRIPTION

Figure 1:
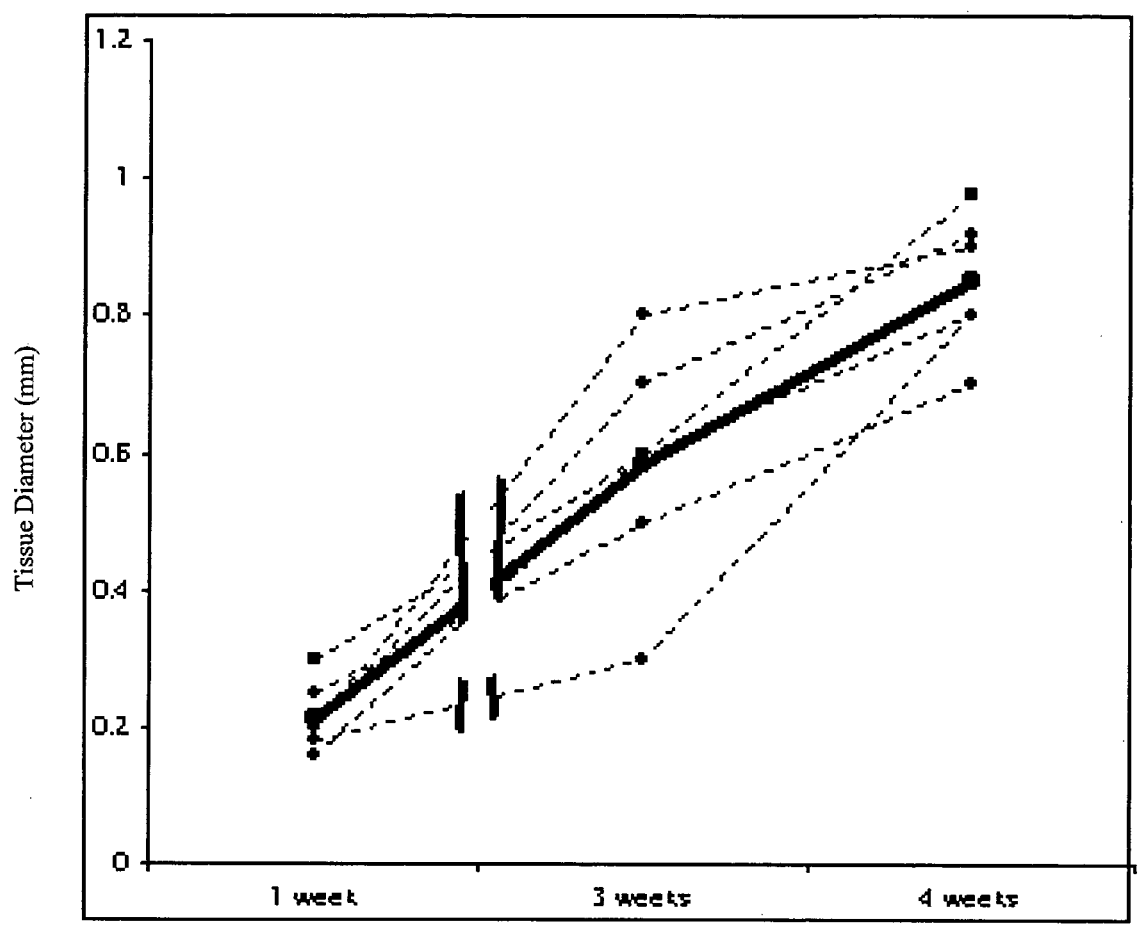
FIG. 1 is a graph of tissue diameter (mm) over time (weeks) of engineered muscle tissue retrieved at 1, 3 and 4 weeks after transplantation with myoblasts transfected with functional VEGF-cDNA.

The practice of the present invention employs, unless otherwise indicated, conventional methods of microbiology, molecular biology and recombinant DNA techniques within the skill of the art. Such techniques are explained fully in the literature. (See, e.g., Sambrook, et al. Molecular Cloning: A Laboratory Manual (Current Edition); DNA Cloning: A Practical Approach, Vol. I & II (D. Glover, ed.); Oligonucleotide Synthesis (N. Gait, ed., Current Edition); Nucleic Acid Hybridization (B. Hames & S. Higgins, eds., Current Edition); Transcription and Translation (B. Hames & S. Higgins, eds., Current Edition); CRC Handbook of Parvoviruses, Vol. I & II (P. Tijessen, ed.); Fundamental Virology, 2nd Edition, Vol. I & II (B. N. Fields and D. M. Knipe, eds.)). The invention also uses techniques described a tissue engineering literatures (see e.g., Principles of Tissue Engineering by Lanza et al (Current Edition). So that the invention may more readily be understood, certain terms are first defined:

The term "angiogenesis" as used herein refers to a process of tissue vascularization that involves the development of new vessels. Angiogenesis is a complex process involving the breakdown of extracellular matrix, with proliferation and migration of endothelial and smooth muscle cells ultimately resulting in the formation and organization of new blood vessels (Folkman, J., and Klagsbrun, M., Science 235:442-7, 1987). Angiogenesis typically occurs via one of three mechanisms: (1) neovascularization, where endothelial cells migrate out of pre-existing vessels beginning the formation of the new vessels; (2) vasculogenesis, where the vessels arise from precursor cells de novo; or (3) vascular expansion, where existing small vessels enlarge in diameter to form larger vessels (Blood, C. H., and Zetter, B. R., Biochem. Biophys. Acta. 1032:89-118, 1990). Angiogenesis is an important process in normal processes of neonatal growth and in the female reproductive system during the corpus luteum growth cycle (Moses, M. A., et al., Science 248: 1408-10, 1990). Under normal conditions, all processes involving the new formation or the remodeling of existing or new blood vessels is a self-limiting process, and the expansion of the specific cell types is controlled and concerted. Angiogenesis is also involved in wound healing and in the pathogenesis of a large number of clinical diseases including tissue inflammation, arthritis, asthma, tumor growth, diabetic retinopathy, and other conditions. Clinical manifestations associated with angiogenesis are referred to as angiogenic diseases.

The term "growth factors" as used herein refers to substances that promote cell growth. It is used to indicate molecules that function as growth simulators (mitogens) but also as growth inhibitors. Growth factors are also known to stimulate cell migration (e.g., mitogenic cytokines), function as chemotactic agents, inhibit cell migration or invasion of tumor cells, modulate differentiated functions of cells, be involved in apoptosis and promote survival of cells. Such factors can be secreted as diffusible factors and can also exist in membrane-anchored forms. They can, therefore, act in an autocrine, paracrine, juxtacrine or retrocrine manner. A cytokine is one type of growth factor. Examples of growth factors include, but are not limited to, VEGF, fibroblast growth factors (FGF), epidermal growth factor (EGF), platelet derived growth factor (PDGF), Transforming growth factors-beta (TGF-beta), transforming growth factor-alpha (TGF-α), insulin-like growth factors, erythropoietin (Epo), tumor necrosis factor-alpha (TNF-α), tumor necrosis factor-beta (TNF-β), interferon-γ (INF-γ), and colony stimulating factors (CSFS) or variants thereof.

The term "angiogenesis modulating agent" as used herein refers to any agent that can induce angiogenesis or the proliferation of endothelial cells. For example, an angiogenesis modulating agent includes a cytokine, a growth factor, an enzyme, an enzymatic inhibitor, or an antibody. A "cytokine" is polypeptide which acts as a humoral regulator at nano- to picomolar concentrations and which, either under normal or pathological conditions, can modulate the functional activities of individual cells and tissues. A cytokine can mediate interactions between cells directly and/or can regulate processes taking place in the extracellular environment. Cytokines comprise interleukins, lymphokines, monokines, interferons, colony stimulating factors, and chemokines, in addition to a variety of other proteins.

One class of angiogenesis modulating agents are polypeptide angiogenic factors, such as cytokines and growth factors, which includes, but is not limited to, angiopoeitin-1, epidermal growth factor (EGF), hepatocyte growth factor (HGF), tumor necrosis factor (TNF-alpha), platelet derived endothelial cell growth factor (PD-ECGF), platelet derived growth factor (PDGF), insulin-like growth factor (IGF), interleukin-8, growth hormone, angiopoietin, vascular endothelial growth factor (VEGF), acidic and basic fibroblast growth factors (FGFs), transforming growth factor alpha (TGF-α), CYR 61 (Babic et al., Proc. Natl. Acad. Sci. USA, 95:6355, 1998; Kireeva et al., Mol. Cell. Biol. 16:1326, 1996) and platelet-derived growth factor (PDGF). These molecules have been shown to induce angiogenesis in vivo. Other similar molecules that display angiogenic activity are the heparin binding growth factors (HBGFs). Other angiogenesis modulating agents have been described in addition to polypeptide angiogenic factors. For example, prostaglandins $E_1$ and $E_2$, which are lipid-derived angiogenic factors, are well known inflammatory cell attractants with angiogenic properties (J. Natl. Cancer Inst. 69,475-482, 1982). In addition, nicotinamide causes an angiogenic response when tested in chick cornea or in a chick CAM assay (Science 236, 843-845, 1987). In addition, negative angiogenic regulatory molecules include angiostatin (O'Reilly et al., Cell 79:315, 1994); endostatin (O'Reilly et al., Cell. 88:277, 1997); and thrombospondin (Good et al., Proc. Natl. Acad. Sci. USA, 87:6624, 1990).

The term "pharmaceutically acceptable carrier," as used herein, refers to any materials which do not have toxic or injurious effects on biological functions. Natural or synthetic polymers can be used as the pharmaceutically acceptable carrier, although synthetic polymers are preferred for reproducibility and controlled release kinetics. Synthetic polymers that can be used to form the microspheres include bioerodible polymers such as poly(lactide) (PLA), poly(glycolic acid) (PGA), poly(lactide-co-glycolide) (PLGA), poly(caprolactone), polycarbonates, polyamides, polyanhydrides, polyamino acids, polyortho esters, polyacetals, polycyanoacrylates and degradable polyurethanes, and non-erodible polymers such as polyacrylates, ethylene-vinyl acetate polymers and other acyl substituted cellulose acetates and derivatives thereof, non-erodible polyurethanes, polystyrenes, polyvinyl chloride, polyvinyl fluoride, poly(vinyl imidazole), chlorosulphonated polyolefins, and polyethylene oxide. Examples of natural polymers include proteins such as albumin, collagen, synthetic polyamino acids, and prolamines, and polysaccharides such as alginate, heparin, and other naturally occurring biodegradable polymers of sugar units.

The normally charged outer layer of the microcapsules can be covered by water soluble non-ionic polymers such as poly (ethylene oxide) (PEO) which act to shield the charge. These polymers are grafted to the polycationic polymers, such as poly-L-lysine (PLL) molecules used as at least one of the layers of the microcapsule, such that they create a non-ionic barrier between the outer layer of the microcapsule (made of essentially either polycationic polymers, such as PLL, or polyanionic polymers, such as alginate) and the target tissue.

PLA, PGA and PLA/PGA copolymers are particularly useful for forming microspheres. PLA polymers are usually prepared from the cyclic esters of lactic acids. Both L(+) and D(−) forms of lactic acid can be used to prepare the PLA polymers, as well as the optically inactive DL-lactic acid mixture of D(−) and L(+) lactic acids. Methods of preparing polylactides are well documented in the patent literature. The following U.S. patents, the teachings of which are hereby incorporated by reference, describe in detail suitable polylactides, their properties and their preparation: U.S. Pat. No. 1,995,970 to Dorough; U.S. Pat. No. 2,703,316 to Schneider; U.S. Pat. No. 2,758,987 to Salzberg; U.S. Pat. No. 2,951,828 to Zeile; U.S. Pat. No. 2,676,945 to Higgins; and U.S. Pat. Nos. 2,683,136; 3,531,561 to Trehu.

By altering the properties of the polymer and the properties of the dosage form, one can control the contribution of each of these release mechanisms and alter the release rate of Factors. Slowly eroding polymers such as poly L-lactide or high molecular weight poly(lactide-co-glycolide) with low glycolide compositions will cause the release to become diffusion controlled. Increasing the glycolide composition and decreasing the molecular weight enhances both water uptake and the hydrolysis of the polymer and adds an erosion component to the release kinetics. In a preferred embodiment, the pharmaceutically acceptable carrier comprises alginate-PLL capsules.

A pharmaceutically acceptable carrier can also be biodegradable. Biodegradable refers to material that can be absorbed or degraded in a patient's body. Representative materials for forming the biodegradable structure include natural or synthetic polymers, such as, for example, collagen, poly (alpha esters) such as poly (lactate acid), poly (glycolic acid) (PGA), polyorthoesters and polyanhydrides and their copolymers, which degraded by hydrolysis at a controlled rate and are reabsorbed. These materials provide the maximum control of degradability, manageability, size and configuration. Preferred biodegradable polymer material include polyglycolic acid and polygalactin, developed as absorbable synthetic suture material. Polyglycolic acid and polygalactin fibers may be used as supplied by the manufacturer. Other biodegradable materials include cellulose ether, cellulose, cellulosic ester, fluorinated polyethylene, phenolic polymer, poly-4-methylpentene, polyacrylonitrile, polyamide, polyamideimide, polyacrylate, polybenzoxazole, polycarbonate, polycyanoarylether, polyester, polyestercarbonate, polyether, polyetheretherketone, polyetherimide, polyetherketone, polyethersulfone, polyethylene, polyfluoroolefin, polyimide, polyolefin, polyoxadiazole, polyphenylene oxide, polyphenylene sulfide, polypropylene, polystyrene, polysulfide, polysulfone, polytetrafluoroethylene, polythioether, polytriazole, polyurethane, polyvinyl, polyvinylidene fluoride, regenerated cellulose, silicone, urea-formaldehyde, or copolymers or physical blends of these materials. The material may be impregnated with suitable antimicrobial agents and may be colored by a color additive to improve visibility and to aid in surgical procedures.

The pharmaceutical acceptable carrier can be non-biodegradable such the growth factor can be secreted through the carrier while the cells remain immunoisolated from the target tissue into which they are implanted. Semipermeable microcapsules can be produced through interfacial polymerization as described in U.S. Pat. No. 4,251,387. In a preferred embodiment, alginate-PLL capsules are used. Microencapsulation of cells generally involves three steps: (a) generating microcapsules enclosing the cells (e.g., by forming droplets of cell-containing liquid alginate followed by exposure to a solution of calcium chloride to form a solid gel), (b) coating the resulting gelled spheres with additional outer coatings (e.g., outer coatings comprising polylysine and/or polyomithine) to form a semipermeable membrane; and (c) liquefying the original core gel (e.g., by chelation using a solution of sodium citrate). The three steps are typically separated by washings in normal saline.

Alginates are linear polymers of mannuronic and guluronic acid residues. Monovalent cation alginate salts, e.g., Na-alginate, are generally soluble. Divalent cations such as $Ca^{2+}$, $Ba^{2+}$ or $Sr^{2+}$ tend to interact with guluronate, providing crosslinking and forming stable alginate gels. Alginate encapsulation techniques typically take advantage of the gelling of alginate in the presence of divalent cation solutions. Alginate encapsulation of cells generally involves suspending the cells to be encapsulated in a solution of a monovalent cation alginate salt, generating droplets of this solution, and contacting the droplets with a solution of divalent cations. The divalent cations interact with the alginate at the phase transition between the droplet and the divalent cation solution, resulting in the formation of a stable alginate gel matrix being formed. A variation of this technique is reported in U.S. Pat. No. 5,738,876, wherein the cell is suffused with a solution of multivalent ions (e.g., divalent cations) and then suspended in a solution of gelling polymer (e.g., alginate), to provide a coating of the polymer.

A preferred method of microencapsulating cells is the alginate-polyamino acid technique. Cells are suspended in sodium alginate in saline, and droplets containing islets are produced. Droplets of cell-containing alginate flow into calcium chloride in saline. The negatively charged alginate droplets bind calcium and form a calcium alginate gel. The microcapsules are washed in saline and incubated with poly-L-lysine (PLL) or poly-L-ornithine (or combinations thereof); the positively charged poly-1-lysine and/or poly-L-ornithine displaces calcium ions and binds (ionic) negatively charged alginate, producing an outer poly-electrolyte membrane. A final coating of sodium alginate may be added by washing the microcapsules with a solution of sodium alginate, which ionically bonds to the poly-L-lysine and/or poly-L-ornithine layer. See U.S. Pat. No. 4,391,909 to Lim et al (all U.S. patents referenced herein are intended to be incorporated herein in their entirety). This technique produces what has been termed a "single-wall" microcapsule. Preferred microcapsules are essentially round, small, and uniform in size. (Wolters et al., *J. Appli Biomater.* 3:281 (1992)).

The alginate-polylysine microcapsules can also then be incubated in sodium citrate to solubilize any calcium alginate that has not reacted with poly-1-lysine, i.e., to solubilize the internal core of sodium alginate containing the islet cells, thus producing a microcapsule with a liquefied cell-containing core portion. See Lim and Sun, Science 210:908 (1980). Such microcapsules are referred to herein as having "chelated", "hollow" or "liquid" cores. A "double-wall" microcapsule is produced by following the same procedure as for single-wall microcapsules, but prior to any incubation with sodium citrate, the microcapsules are again incubated with poly-1-lysine and sodium alginate.

Chelation of the alginate (degelling) core solubilizes the internal structural support of the capsule, may adversely affect the durability of the microcapsule, and is a harsh treatment of the encapsulated living cells. Degelling of the core may also cause leaching out of the unbound poly-lysine or solubilized alginate, resulting in a fibrotic reaction to the implanted microcapsule. The effect of core liquidation on glucose-stimulated insulin secretion by the encapsulated cells has been studied. Fritschy et al., Diabetes 40:37 (1991). The present inventors examined the function of islets enclosed in microcapsules that had not been subjected to liquefaction of the core (i.e., 'solid' or non-chelated microcapsules). It was found that culture of solid microcapsules prior to use enhanced the insulin response of the enclosed islets to glucose stimulation.

Many alternative techniques used for encapsulating cells are known in the art and can be used with this invention. U.S. Pat. No. 5,084,350 discloses microcapsules enclosed in a larger matrix, where the microcapsules are liquefied once the microcapsules are within the larger matrix. Tsang et al., U.S. Pat. No. 4,663,286 discloses encapsulation using an alginate polymer, where the gel layer is cross-linked with a polycationic polymer such as polylysine, and a second layer formed using a second polycationic polymer (such as polyornithine); the second layer can then be coated by alginate. U.S. Pat. No. 5,762,959 to Soon-Shiong et al. discloses a microcapsule having a solid (non-chelated) alginate gel core of a defined ratio of calcium/barium alginates, with polymer material in the core. U.S. Pat. Nos. 5,801,033 and 5,573,934 to Hubbell et al. describe alginate/polylysine microspheres having a final polymeric coating (e.g., polyethylene glycol (PEG)); Sawhney et al., Biomaterials 13:863 (1991) describe alginate/polylysine microcapsules incorporating a graft copolymer of poly-1-lysine and polyethylene oxide on the microcapsule surface, to improve biocompatibility; U.S. Pat. No. 5,380,536 describes microcapsules with an outermost layer of water soluble non-ionic polymers such as polyethylene(oxide). U.S. Pat. No. 5,227,298 to Weber et al. describes a method for providing a second alginate gel coating to cells already coated with polylysine alginate; both alginate coatings are stabilized with polylysine. U.S. Pat. No. 5,578,314 to Weber et al. provides a method for microencapsulation using multiple coatings of purified alginate. U.S. Pat. No. 5,693,514 to Dorian et al. reports the use of a non-fibrogenic alginate, where the outer surface of the alginate coating is reacted with alkaline earth metal cations comprising calcium ions and/or magnesium ions, to form an alkaline earth metal alginate coating. The outer surface of the alginate coating is not reacted with polylysine. U.S. Pat. No. 5,846,530 to Soon-Shiong describes microcapsules containing cells that have been individually coated with polymerizable alginate, or polymerizable polycations such as polylysine, prior to encapsulation.

The phrases "augmenting organ function" or "augmenting function of an organ" as used herein refers to increasing, enhancing, improving, the function of an organ that is operating at less than optimum capacity. The term is used to refer to a gain in function so that the organ is operating at a physiologically acceptable capacity for that subject. For example, the physiological acceptable capacity for an organ from a child, e.g., a kidney or heart, would be different from the physiological acceptable capacity of an adult, or an elderly patient. The entire organ, or part of the organ can be augmented. Preferably the augmentation results in an organ with the same physiological response as a native organ. In a preferred embodiment, an organ is augmented in capacity when it is functioning to at least 10% of its natural capacity.

The phrases "three-dimensional biomatrix" or "augmenting construct" or "neomorphic organ augmenting structure" as used herein refers to a mini-matrix that has been perfused with the cells and cultured until the cells form a tissue layer. The tissue layer can be a single monolayer, or multiple layers. Tissue-specific cells refer to cells derived from the specific organ requiring augmentation, e.g., cells from a kidney organ for organ augmentation, and cells from a heart for heart organ augmentation. The cells in the three-dimensional biomatrix establish a "tissue-like" histology, can regenerate tissue-like architecture, and develop into primitive organoids with complex, multilayered structures that can eventually develop into the actual organ, or part of the organ. The three-dimensional biomatrix is an artificial organ, or part of an organ is the "functional equivalent" of the natural organ, i.e., behaves in the same, or similar manner as a natural organ, for example, the artificial kidney has the same functional characteristics as an in vivo kidney. For example, a kidney augmenting structure can be one that has a layer of tissue capable of developing into nephron structures, or part of a nephron structure. For kidney augmentation, the tissue specific cells can be an isolated population of cells selected from the group consisting of distil tubule cells, proximal tubule cells glomeruli cells, Bowman's capsule cells, and loop of Henlè cells. Alternatively, the tissue specific cells can be a mixed population of cells that includes distil tubule cells, proximal tubule cells, glomeruli cells, Bowman's capsule cells, and loop of Henlè cells. Various three-dimensional biomatrices that address specific diseases or disorders can be created. For example, the three-dimensional biomatrix can be specifically created to ameliorate disorders associated with the glomerulus by using an homogenous population of glomeruli cells that are used to perfuse the matrix material. Alternatively, the three-dimensional biomatrix can be a general construct created using a mixed population of renal cells.

When the three-dimensional biomatrix is brought into contact with a host tissue at a target site in the organ, it is able to grow and proliferate within the target site and replenish or augment the depleted activity of the organ at that site. The augmenting construct can be added at a single location in the organ. Alternatively, a plurality of augmenting constructs can be created and added to multiple sites in the organ.

The phrase "renal cells" as used herein refers to cells derived from any region of the kidney, such as cells from the distil tubule cells, proximal tubule cells, glomeruli cells, Bowman's capsule cells, or loop of Henlè cells. The term is used to refer a mixture of cells that includes all cells from the kidney. The term is also used to refer to an isolated sub-population of cells from a region of the nephron, e.g., a single population of only glomeruli cells. Cells form the kidney can be derived by taking a biopsy from the subject. Cell sorting techniques can be used to isolate healthy cells from diseased cells. Cell sorting techniques can also be used to isolated sub-populations of cells.

The term "nephron structure" as used herein refers the entire functional unit of the kidney that removes waste and excess substances from the blood to produce urine. Each of The million or so nephrons in each kidney are a tubule 1.2-2.2 inches (30-55 mm) long. At one end it is closed, expanded, and folded into a double-walled cuplike structure called the "Bowman's capsule", enclosing a cluster of capillaries called the "glomerulus". Fluid forced out of the blood through the capillary walls of the glomerulus into Bowman's capsule flows into the adjacent renal tubule, where water and nutrients are selectively reabsorbed from the fluid back into the blood, and electrolytes such as sodium and potassium are balanced in the loop of Henlè and proximal tubules. The final concentrated product is collected in the collecting duct as urine.

The term "part of a nephron structure" as used herein refers any section of the nephron. For example, a cell population can be sorted to produce an isolated population of only glomeruli cells. This isolated population of glomeruli cells can be used to seed a mini-matrix material and cultured to produce a three-dimensional mini-biomatrix with a glomeruli tissue layer that differentiates into a glomerulus. The same methodology can be applied to generate three-dimensional mini-biomatrices with specific cells derived from different regions of the nephron, that differentiate into the that part of the nephron, such as the distil tubule region. Other kidney disorders that are associated with a particular region of the nephron include those pathologies associated with the tubular cells.

The term "target site" as used herein refers to region in the organ that requires augmentation. The target site can be a single region in the organ, or can be multiple regions in the organ. The entire organ, or part of the organ can be augmented. Preferably the augmentation results in an organ with the same physiological response as a normal organ. The entire organ can be augmented by placing a plurality of biomatrices at suitable distances along the entire organ, e.g., along the entire longitudinal section of a kidney. Alternatively, part of the organ can be augmented by placing at least one biomatrix in one target site of the organ, e.g., the top of the kidney.

The term "attach" or "attaches" as used herein refers to cells adhered directly to the matrix or to cells that are themselves attached to other cells.

The phrase "mini-matrix material" as used herein refers to a supportive framework that allows cells to attach. Preferably, the "mini-matrix," has a greatest dimension which is less than about 50 millimeters. In one preferred embodiment, the matrix is a substantial flat structure having a ratio of its greatest dimension to its thickness of greater than 5:1. The mini-matrix material is composed of any material and/or shape that allows cells to attach to it, or in it (or can be modified to allow cells to attach to it, or in it); and allows cells to grow into at least one monolayer or at least one tissue layer. Cultured populations of cells can then be grown on the matrix, or within the matrix. In one embodiment, the matrix material is a polymeric matrix which provides the desired interstitial distances required for cell-cell interaction. In another embodiment, the matrix material is a hydrogel composed of crosslinked polymer networks which are typically insoluble or poorly soluble in water, but can swell to an equilibrium size in the presence of excess water. Due to the unique properties of hydrogels and their potential applications in such areas as controlled drug delivery, various types of hydrogels have been synthesized and characterized.

The size of the mini-matrix material also varies according to the area of the organ being augmented. The size is typically smaller than the entire organ. Preferably, the volume of the matrix can range from about 1 $mm^3$ to the size of the organ. Most preferably, the size in volume is about 0.01 $mm^3$ to about 30 $mm^3$, more preferably, about 0.1 $mm^3$ to about 20 $mm^3$, even more preferably about 1 $mm^3$, 2 $mm^3$, 3 $mm^3$, 4 $mm^3$, 5 $mm^3$, 6 $mm^3$, 7 $mm^3$, 8 $mm^3$, 9 $mm^3$, and 10 $mm^3$ in volume. Elongate or flat matrices are preferably in many applications. Preferably, the length of greatest dimension of the matrix is greater than 0.2 mm and less than 100 mm, more preferably ranging from about 0.50 mm to about 30 mm. In a preferred embodiment, the shape of the mini-matrix is substantially flat and has a ratio of its greatest dimension to its thickness of greater than 5:1, more preferably greater than 10:1.

The shape and dimensions of the mini-matrix material is determined based on the organ being augmented, and the type of mini-matrix material being used to create the mini-biomatrix. For example, if a polymeric matrix is used for kidney augmentation, the dimension of the polymeric matrix can vary in terms of width and length of the polymeric matrix, for example the dimensions can be about 1 mm width×1 mm length×1 mm height to about 10 mm width×20 mm length×1 mm height. The skilled artisan will appreciate that the size and dimensions of the polymric matrix will be determined based on the area of the organ being augmented, as well as the actual organ being augmented.

Alternatively, if the matrix material is a hydrogel that is being used to augment a kidney, then the volume of the hydrogel can be determined based on the size of the area being augmented in the kidney. For example, a volume of about 1 $mm^3$, 2 $mm^3$, 3 $mm^3$, 4 $mm^3$, 5 $mm^3$, 6 $mm^3$, 7 $mm^3$, 8 $mm^3$, 9 $mm^3$, and 01 $mm^3$ into which a population of cells cultured. In one embodiment, the hydrogel can be injected into one or more target sites in the organ. The volume of the hydrogel can be altered based on the organ and area of the organ being augmented. For example if the organ is a heart, and an area of infarction in the heart is being augmented, the volume of the hydrogel can range from a volume smaller than the size of the infarction to a volume that is the actual size of the infarction.

The term "biostructure" as used herein refers to parts of organs that have been decellularized by removing the entire cellular and tissue content from the part of the organ.

The term "decellularized" or "decellularization" as used herein refers to a biostructure (e.g., an organ, or part of an organ), from which the cellular and tissue content has been removed leaving behind an intact acellular infra-structure. Organs such as the kidney are composed of various specialized tissues. The specialized tissue structures of an organ, or parenchyma, provide the specific function associated with the organ. The supporting fibrous network of the organ is the stroma. Most organs have a stromal framework composed of unspecialized connecting tissue which supports the specialized tissue. The process of decellularization removes the specialized tissue, leaving behind the complex three-dimensional network of connective tissue. The connective tissue infra-structure is primarily composed of collagen. The decellularized structure provides a matrix material onto which different cell populations can be infused. Decellularized biostructures can be rigid, or semi-rigid, having an ability to alter their shapes. Examples of decellularized organs useful in the present invention include, but are not limited to, the heart, kidney, liver, pancreas, spleen, bladder, ureter and urethra.

The phrase "three-dimensional scaffold" as used herein refers to the residual infra-structure formed when a natural biostructure, e.g. an organ, is decellularized. This complex, three-dimensional, scaffold provides the supportive framework that allows cells to attach to it, and grow on it. Cultured populations of cells can then be grown on the three-dimensional scaffold, which provides the exact interstitial distances required for cell-cell interaction. This provides a reconstructed organ that resembles the native in vivo organ. This three-dimensional scaffold is perfused with a population of cultured endothelial cells which grow and develop to provide an endothelial tissue layer comprising a primitive vascular system that is capable of developing into a mature vascular system. The endothelial tissue layer and the primitive vascular system is also capable of supporting growth and development of at least one additional cultured cell population.

The term "primitive vascular system" as used herein refers to the early stages of development of a vascular system comprising blood vessels that supply blood to the tissue structures.

The term "therapeutically effective dose" as used herein refers to the quantity of a compound according to the invention necessary to locally alter the circulation. Amounts effective for this use will, of course, depend on the severity of the disease and the weight and general state of the patient. Typically, dosages used in vitro may provide useful guidance in the amounts useful for in situ administration of the pharmaceutical composition, and animal models may be used to determine effective dosages for treatment of particular disorders. Various considerations are described, e.g., in Gilman et al., eds., Goodman And Gilman's: *The Pharmacological Bases of Therapeutics,* 8th ed., Pergamon Press, 1990; and *Remington's Pharmaceutical Sciences,* 17th ed., Mack Publishing Co., Easton, Pa., 1990, each of which is herein incorporated by reference.

The term "subject," as used herein, refers to any living organism capable of eliciting an immune response. The term subject includes, but is not limited to, humans, nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered.

I. Growth Factors

A. Epidermal Growth Factor (EGF)

EGF, like all growth factors, binds to specific high-affinity, low-capacity receptors on the surface of responsive cells. Intrinsic to the EGF receptor is tyrosine kinase activity, which is activated in response to EGF binding. The kinase domain of the EGF receptor phosphorylates the EGF receptor itself (autophosphorylation) as well as other proteins, in signal transduction cascades, that associate with the receptor following activation. Experimental evidence has shown that the Neu proto-oncogene is a homologue of the EGF receptor. EGF has proliferative effects on cells of both mesodermal and ectodermal origin, particularly keratinocytes and fibroblasts. EGF exhibits negative growth effects on certain carcinomas as well as hair follicle cells. Growth-related responses to EGF include the induction of nuclear proto-oncogene expression, such as Fos, Jun and Myc. EGF also has the effect of decreasing gastric acid secretion.

B. Platelet-Derived Growth Factor (PDGF)

PDGF is composed of two distinct polypeptide chains, A and B, that form homodimers (AA or BB) or heterodimers (AB). The c-Sis proto-oncogene has been shown to be homologous to the PDGF A chain. Only the dimeric forms of PDGF interact with the PDGF receptor. Two distinct classes of PDGF receptor have been cloned, one specific for AA homodimers and another that binds BB and AB type dimers. Like the EGF receptor, the PDGF receptors have intrinsic tyrosine kinase activity. Following autophosphorylation of the PDGF receptor, numerous signal-transducing proteins associate with the receptor and are subsequently tyrosine phosphorylated.

Proliferative responses to PDGF action are exerted on many mesenchymal cell types. Other growth-related responses to PDGF include cytoskeletal rearrangement and increased polyphosphoinositol turnover. PDGF induces the expression of a number of nuclear localized proto-oncogenes, such as Fos, Myc and Jun. The primary effects of TGF-β are due to the induction, by TGF-β, of PDGF expression.

C. Fibroblast Growth Factors (FGFs)

There are at least 19 distinct members of the FGF family of growth factors. The two originally characterized FGFs were identified by biological assay and are termed FGF1 (acidic-FGF, aFGF) and FGF2 (basic-FGF, bFGF). Kaposi's sarcoma cells (prevalent in patients with AIDS) secrete a homologue of FGF called the K-FGF proto-oncogene. In mice the mammary tumor virus integrates at two predominant sites in the mouse genome identified as Int-1 and Int-2. The protein encoded by the Int-2 locus is a homologue of the FGF family of growth factors. Studies of human disorders as well as gene knock-out studies in mice show the prominent role for FGFs is in the development of the skeletal system and nervous system in mammals. FGFs also are neurotrophic for cells of both the peripheral and central nervous system. Additionally, several members of the FGF family are potent inducers of mesodermal differentiation in early embryos. Non-proliferative effects include regulation of pituitary and ovarian cell function.

The FGFs interact with specific cell-surface receptors. There have been identified 4 distinct receptor types identified as FGFR1-FGFR4. Each of these receptors has intrinsic tyrosine kinase activity like both the EGF and PDGF receptors. As with all transmembrane receptors that have tyrosine kinase activity, autophosphorylation of the receptor is the immediate response to FGF binding. Following activation of FGF receptors, numerous signal-transducing proteins associate with the receptor and become tyrosine-phosphorylated. The Flg proto-oncogene is a homologue of the FGF receptor family. The FGFR1 receptor also has been shown to be the portal of entry into cells for herpes viruses. FGFs also bind to cell-surface heparan-sulfated proteoglycans with low affinity relative to that of the specific receptors. The purpose in binding of FGFs to theses proteoglycans is not completely understood but may allow the growth factor to remain associated with the extracellular surface of cells that they are intended to stimulate under various conditions.

The FGF receptors are widley expressed in developing bone and several common autosomal dominant disorders of bone growth have been shown to result from mutations in the FGFR genes. The most prevalent is achondroplasia, ACH. ACH is characterized by disproportionate short stature, where the limbs are shorter than the trunk, and macrocephaly (excessive head size). Almost all persons with ACH exhibit a glycine to arginine substitution in the transmembrane domain of FGFR3. This mutation results in ligand-independent activation of the receptor. FGFR3 is predominantly expressed in quiescent chondrocytes where it is responsible for restricting chondrocyte proliferation and differentiation. In mice with inactivating mutations in FGFR3 there is an expansion of long bone growth and zones of proliferating cartilage further demonstrating that FGFR3 is necessary to control the rate and amount of chondrocyte growth.

Several other disorders of bone growth collectively identified as craniosynostosis syndromes have been shown to result from mutations in FGFR1, FGFR2 and FGFR3. Sometimes the same mutation can cause two or more different craniosynostosis syndromes. A cysteine to tyrosine substitution in FGFR2 can cause either Pfeiffer or Crouzon syndrome. This phenomenon indicates that additional factors are likely responsible for the different phenotypes.

D. Transforming Growth Factors-β (TGFs-β)

TGF-β was originally characterized as a protein (secreted from a tumor cell line) that was capable of inducing a transformed phenotype in non-neoplastic cells in culture. This effect was reversible, as demonstrated by the reversion of the cells to a normal phenotype following removal of the TGF-β. Subsequently, many proteins homologous to TGF-β have been identified. The four closest relatives are TGF-β-1 (the original TGF-β) through TGF-β-5 (TGF-β-1=TGF-β-4). All four of these proteins share extensive regions of similarity in their amino acids. Many other proteins, possessing distinct biological functions, have stretches of amino-acid homology to the TGF-β family of proteins, particularly the C-terminal region of these proteins.

The TGF-β-related family of proteins includes the activin and inhibin proteins. There are activin A, B and AB proteins, as well as an inhibin A and inhibin B protein. The Mullerian inhibiting substance (MIS) is also a TGF-β-related protein, as are members of the bone morphogenetic protein (BMP) family of bone growth-regulatory factors. Indeed, the TGF-β family may comprise as many as 100 distinct proteins, all with at least one region of amino-acid sequence homology.

There are several classes of cell-surface receptors that bind different TGFs-β with differing affinities. There also are cell-type specific differences in receptor sub-types. Unlike the EGF, PDGF and FGF receptors, the TGF-β family of receptors all have intrinsic serine/threonine kinase activity and, therefore, induce distinct cascades of signal transduction.

TGFs-β have proliferative effects on many mesenchymal and epithelial cell types. Under certain conditions TGFs-β will demonstrate anti-proliferative effects on endothelial cells, macrophages, and T- and B-lymphocytes. Such effects include decreasing the secretion of immunoglobulin and suppressing hematopoiesis, myogenesis, adipogenesis and adrenal steroidogenesis. Several members of the TGF-β family are potent inducers of mesodermal differentiation in early embryos, in particular TGF-β and activin A.

E. Transforming Growth Factor-α (TGF-α)

TGF-α, like the β, form, was first identified as a substance secreted from certain tumor cells that, in conjunction with TGF-β-1, could reversibly transform certain types of normal cells in culture. TGF-α binds to the EGF receptor, as well as its own distinct receptor, and it is this interaction that is thought to be responsible for the growth factor's effect. The predominant sources of TGF-α are carcinomas, but activated macrophages and keratinocytes (and possibly other epithelial cells) also secrete TGF-α. In normal cell populations, TGF-α is a potent keratinocyte growth factor; forming an autocrine growth loop by virtue of the protein activating the very cells that produce it.

F. Erythropoietin (Epo)

Epo is synthesized by the kidney and is the primary regulator of erythropoiesis. Epo (Accession No. NP 000790) stimulates the proliferation and differentiation of immature erythrocytes; it also stimulates the growth of erythoid progenitor cells (e.g. erythrocyte burst-forming and colony-forming units) and induces the differentiation of erythrocyte colony-forming units into proerythroblasts. When patients suffering from anemia due to kidney failure are given Epo, the result is a rapid and significant increase in red blood cell count.

G. Insulin-Like Growth Factor-I (IGF-I)

IGF-I (originally called somatomedin C) is a growth factor structurally related to insulin. IGF-I is the primary protein involved in responses of cells to growth hormone (GH): that is, IGF-I is produced in response to GH and then induces subsequent cellular activities, particularly on bone growth. It is the activity of IGF-I in response to GH that gave rise to the term somatomedin. Subsequent studies have demonstrated, however, that IGF-I has autocrine and paracrine activities in addition to the initially observed endocrine activities on bone. The IGF-I receptor, like the insulin receptor, has intrinsic tyrosine kinase activity. Owing to their structural similarities IGF-I can bind to the insulin receptor but does so at a much lower affinity than does insulin itself.

H. Insulin-Like Growth Factor-II (IGF-II)

IGF-II is almost exclusively expressed in embryonic and neonatal tissues. Following birth, the level of detectable IGF-II protein falls significantly. For this reason IGF-II is thought to be a fetal growth factor. The IGF-II receptor is identical to the mannose-6-phosphate receptor that is responsible for the integration of lysosomal enzymes (which contain mannose-6-phosphate residues) to the lysosomes.

I. Tumor Necrosis Factor

TNF-α (also called cachectin), like IL-1 is a major immune response—modifying cytokine produced primarily by activated macrophages. Like IL-1, TNF-a induces the expression of other autocrine growth factors, increases cellular responsiveness to growth factors and induces signaling pathways that lead to proliferation. TNF-α acts synergistically with EGF and PDGF on some cell types. Like other growth factors, TNF-α induces expression of a number of nuclear proto-oncogenes as well as of several interleukins.

TNF-β (also called lymphotoxin) is characterized by its ability to kill a number of different cell types, as well as the ability to induce terminal differentiation in others. One significant non-proliferative response to TNF-β is an inhibition of lipoprotein lipase present on the surface of vascular endothelial cells. The predominant site of TNF-β synthesis is T-lymphocytes, in particular the special class of T-cells called cytotoxic T-lymphocytes (CTL cells). The induction of TNF-β expression results from elevations in IL-2 as well as the interaction of antigen with T-cell receptors.

J. Interferon-γ (INF-γ)

IFN-α, IFN-β and IFN-w are known as type I interferons and are predominantly responsible for the antiviral activities of the interferons. In contrast, IFN-γ is a type II or immune interferon. Although IFN-γ, has antiviral activity it is significantly less active at this function than the type I IFNs. Unlike the type I IFNs, IFN-γ is not induced by infection nor by double-stranded RNAs. IFN-γ is secreted primarily by CD8+ T-cells. Nearly all cells express receptors for IFN-γ and respond to IFN-γ binding by increasing the surface expression of class I MHC proteins, thereby promoting the presentation of antigen to T-helper (CD4+) cells. IFN-γ also increases the presentation of class II MHC proteins on class II cells further enhancing the ability of cells to present antigen to T-cells.

K. Colony Stimulating Factors (CSFs)

CSFs are cytokines that stimulate the proliferation of specific pluripotent stem cells of the bone marrow in adults. Granulocyte-CSF (G-CSF) is specific for proliferative effects on cells of the granulocyte lineage. Macrophage-CSF (M-CSF) is specific for cells of the macrophage lineage. Granulocyte-macrophage-CSF (GM-CSF) has proliferative effects on both classes of lymphoid cells. Epo is also considered a CSF as well as a growth factor, since it stimulates the proliferation of erythrocyte colony-forming units. IL-3 (secreted primarily from T-cells) is also known as multi-CSF, since it stimulates stem cells to produce all forms of hematopoietic cells.

II. Vascular Endothelial Growth Factor (VEGF)

Angiogenesis, the process of new blood vessel formation from pre-existing vasculature, is regulated by different growth factors ((Klagsbrun et al. *Annu. Rev. Physiol.* (1991) 53: 217); (Risau W. (1997) *Nature* 386: 671)). These growth factors stimulate endothelial cells which are already present in the patients body to migrate to the implanted area of need, where they proliferate and differentiate into blood vessels (Polverini, P. J. (1996) *Crit. Rev. Oral. Biol. MED* 6: 230). Angiogenesis plays an essential role in embryonic development, normal growth of tissues, wound healing, the female reproductive cycle (i.e., ovulation, menstruation and placental development), as well as a major role in many diseases (Folkman, J. (1995) *N. Engl. J Med.* 26:1757.) Particular interest has focused on cancer, since tumors cannot grow beyond a few millimeters in size without developing a new blood supply. Angiogenesis is also necessary for the spread and growth of tumor cell metastases (Folkman, J. (1990) *J. Natl. Cancer Inst.* 82:4; Zetter, B. (1998) *Annu. Rev. Med.* 49:407).

One of the most important growth and survival factors for endothelium is vascular endothelial growth factor (VEGF). VEGF induces angiogenesis and endothelial cell proliferation and it plays an important role in regulating vasculogenesis. Vascular endothelial growth factor (VEGF) is a heparin-binding, homodimeric, heavily glycosylated protein of 46-48 kDa (24 kDa subunits) (See Ferrara, N., et al., *J. Cell Bio.* 47:211, 1991; Ferrara, N., et al., *Endocrin. Rev.* 13:18-32, 1991; Houck, K. A. et al. (1992) *J. Biol. Chem.* 267:26031; Park, J. E. et al. (1993) *Mol. Biol. Cell* 4:1317; Houck, K. A. et al. (1991) *Mol. Endocrinol.* 5:1806). Glycosylation is not required, however, for biological activity. Most types of cells, but usually not endothelial cells themselves, secrete VEGF. Since the initially discovered that VEGF, VEGF-A, increases vascular permeability, it was known as vascular permeability factor (Dvorak, H. F. et al. (1999) *Curr. Top. Microbiol. Immunol.* 237:97). In addition, VEGF causes vasodilatation, partly through stimulation of nitric oxide synthase in endothelial cells (Yang, R. et al. (1996) *J. Cardiovasc. Pharmacol.* 27:838). VEGF can also stimulate cell migration and inhibit apoptosis (Alon, T. et al. (1995) *Nat. Med.* 1:1024.)

VEGF-A, a dimeric glycoprotein that, as a result of slicing of a single gene, exists primarily as homodimers of one of five different moleculr species. In humans, the most common splice variants of VEGF-A are 121, 145, 165, 189 and 206 amino acids (aa). The sequence of VEGF can be found in Genbank at Accession No. P15692 and is shown below:

and D. Collen (1999) *Curr. Top. Microbiol. Immunol.* 237:133). Placenta growth factor (PlGF) is also closely related to VEGF-A. VEGF-A, -B, -C, -D, and PlGF are all distantly related to platelet-derived growth factors-A and -B. VEGF significantly influences vascular permeability and is a strong angiogenic protein in several bioassays, and has been shown to be a highly specific mitogen for vascular endothelial cells. In vitro, the two shorter forms of VEGF stimulate the proliferation of macrovascular endothelial cells, but does not appear to enhance the proliferation of other cell types.

Several studies have shown that association of high serum levels of VEGF with poor prognosis in cancer patients may be correlated with an elevated platelet count (O'Byrne, K. J. et al. (1999) *Lancet* 353:1493). Many tumors release cytokines that can stimulate the production of megakaryocytes in the marrow and elevate the platelet count, which can indirectly increase VEGF delivery to tumors. VEGF is implicated in several other pathological conditions associated with enhanced angiogenesis. For example, VEGF plays a role in both psoriasis and rheumatoid arthritis (Koch, A. E. et al. (1994) *J. Immunol.* 152:4149). Diabetic retinopathy is associated with high intraocular levels of VEGF. Inhibition of VEGF function may result in infertility by blockade of corpus luteum function (Ferrara, N. et al. (1998) *Nat. Med.* 4:336). Direct demonstration of the importance of VEGF in tumor growth has been achieved using dominant negative VEGF receptors (Millauer, B. et al. (1996) *Cancer Res.* 56:1615) to block in vivo proliferation, as well as blocking antibodies to VEGF[39] or to VEGF R2.

III. Vascularizing Engineered Tissues

There are many clinical situations in which a large muscle mass is required to replace tissue lost to surgical resection or trauma. It is possible that autologous muscle cell transplan-

```
  1 mnfllswvhw slalllylhh akwsqaapma egggqnhhev vkfmdvyqrs ychpietlvd 61 ifqeypdeie yifkpscvpl mrcggccnde glecvptees nitmqimrik phqgqhigem 121 sflqhnkcec rpkkdrarqe kksvrgkgkg qkrkrkksry kswsvyvgar cclmpwslpg 181 phpcgpcser rkhlfvqdpq tckcsckntd srckarqlel nertcrcdkp rr
```

VEGF$_{165}$ is the most predominant protein, but transcripts of VEGF$_{121}$ may be more abundant (Relf, M. et al. (1997) *Cancer Res.* 57:963). VEGF$_{206}$ is rarely expressed and has been detected only in fetal liver. Other splice variants, such as 183 aa, have also been described ((Kozlowska, U. et al. (1998) *Arch. Dermatol. Res.* 290:661); (Liu, J. J. et al. (1999) Invest. *Ophthalmol. Vis. Sci.* 40:752)). The 165, 189 and 206 aa splice variants have heparin-binding domains, which help anchor them in extracellular matrix and are involved in binding to heparin sulfate and presentation to VEGF receptors. This is a key factor for VEGF potency (i.e., the heparin-binding forms are more active). The 189 amino acid variant of VEGF (VEGF-189) is identical with vascular permeability factor (VPF). VEGF-121 and VEGF-165 are soluble secreted forms of the factor while VEGF-189 and VEGF-206 are mostly bound to heparin-containing proteoglycans in the cell surface or in the basement membrane. Rat and bovine VEGF are one amino acid shorter than the human factor, and the bovine and human sequences show a homology of 95%. The positions of all eight cysteine residues are conserved in VEGF and PDGF. A high-affinity glycoprotein receptor for VEGF of 170-235 kDa is expressed on vascular endothelial cells. Several other members of the VEGF family have been cloned including VEGF-B, -C, and -D. (Eriksson, U. and K. Alitalo (1999) *Curr. Top. Microbiol. Immunol.* 237:97; Carmeliet, P.

tation on biodegradable polymer matrices may provide a new therapy to engineer large muscle which can be used to treat these patients. A number of challenges must be met to engineer and maintain large masses of living cells, upon transfer from the in vitro culture conditions into the host, in vivo. To achieve the goals of engineering large complex tissues, vascularization of the regenerating tissue is essential.

Growth and regeneration of muscle depends on satellite cells, which are able to multiply and generate new muscle fibers. In pathological situations, satellite cell function may be disrupted, leading to the connective tissue deposition and fibrosis. Satellite function may also be affected due to poor vascularization or cell loss secondary to trauma. One of the strategies for the engineering of muscle tissue involves the autologous harvesting of cells, their expansion in vitro, and their subsequent implantation in vivo into affective sites requiring repair or replacement. A major obstacle in the novo formation of muscle tissue, as well as other solid tissues, is an adequate vascular supply. Cells within a bioengineered organ, or at the center of an injected cell mass, need an extensive blood vessel network to supply nutrients and oxygen and remove waste products. Many techniques have been used to circumvent this obstacle. For example, cells have been seeded and grown on micro-porous frameworks as well as scaffolds etched with mini networks imitating vascular systems.

A tissue with more than a few millimeters in volume cannot survive by diffusion of nutrients and requires formation of new blood capillaries to supply essential nutrients and oxygen (Mooney et al. *Sci Am* (1999) 280(4):60-65). The requirements of vessels for "de novo" vascularization of engineered tissues share many similarities with the process of revascularization of an ischemnic tissue. However, while angiogenic processes taking place in ischemic limbs or infracted myocardium have been studied extensively, studies on bioengineered tissue vascularization have not been performed until recently. Efforts have been aimed at incorporating the knowledge acquired on angiogenesis in ischemic tissues into practical approaches to the vascularization of bioengineered tissues. The angiogenic process in the bioengineered tissue must be controlled in order to obtain a functional vascular network (Saaristo et al. *FASEB J.* (2002) 16(9): 1041-1049). The generation of new vessels should follow the kinetics of normal development in the vasculature. High concentrations of angiogenesis modulating agents may be required for the initial differentiation, proliferation, and recruitment of EC to form endothelial tubes. One aspect of the present invention provides methods and compositions for the expression of angiogenesis modulating agents using genetically engineered cells. Examples 1, 2. and 3 demonstrate high levels of VEGF secretion by genetically engineered CHO cells and myoblasts.

One of the most potent angiogenic growth factors, VEGF, acts specifically on endothelial cells, and has been shown to induce rapid formation of blood vessel and capillaries in vivo (Dvorak et al. *Am J. Pathol* (1995) 146:29); (Keck et al. "Vascular permeability factor, an endothelial cell mitogen related to PDGF" *Science* (1989) 246) VEGF protein was applied during implantation or its cDNA was transfected into cells. The former approach did not significantly increase vascularity, and the latter one was associated with unregulated, chronic VEGF expression leading to the formation of vascular abnormalities, i.e. hemangiomas, tissue hemorrhage and vessel proliferative diseases (Henry T D and Abraham J A: *Curr Interv Cardiol Rep.* 2: 228-241., 2000; Lee R J, et al. *Circulation.* 102: 898-901., 2000; Springer M L, et al. *J Gene Med.* 2: 279-88., 2000). Because of such findings, a system of transient and local VEGF administration to promote localized angiogenesis with minimal systemic side effects, as disclosed in this invention, is highly desired.

The problem of adequate blood supply has also become a major obstacle for the bioengineering of urological tissues. Whenever there is a lack of native urological tissue, reconstruction is usually performed with native non-urologic tissues, or recently, with autologous engineered tissues derived from the patients own cells. These reconstructive urologic procedures, which require tissue transfer techniques, rely on adequate vascularization at the surgical site for a successful outcome. In addition to the well established tissue transfer methods which rely on appropriate surgical techniques, several pharmacological approaches have been proposed in an effort to enhance vascularization. Investigators have attempted to promote neovascularization in vivo with the use of several angiogenic stimulating growth factors. However, the present invention provides methods that can be easily incorporated into known bioengineering procedures and will help provide improved vascularization at the site of implantation. In one aspect, the present invention involves the implantation of a population of cells that have been transfected with an angiogenesis modulating agent. In one embodiment, the population of cells can be a group of undifferentiated cells that have been selected for and have been transfected with an angiogenesis modulating agent and can induce assimilation and differentiation of cells in the target region. In another embodiment, two populations of cells can be implanted into the target region—the first population can be a group of undifferentiated cells that assimilated into the target regions and the second population of cells will be transfected with an angiogenesis modulation agent. The second population of cells may or may not assimilate into the target region.

In one aspect of the present invention, a novel system is disclosed consisting of cells engineered to secrete angiogenesis modulating agents. In one embodiment, these cells are encapsulated in an alginate polymer system designed to prevent immunorejection. The present invention was tested in an animal model designed to closely reproduce conditions analogous to free graft transfer in vivo. In another embodiment, collagen based matrices, which have been used clinically as acellular free grafts, or more recently as cellular grafts for tissue engineering, can be used. When using native tissue grafts, the amount of inherent vascularity varies according to tissue type, site of harvest, and from subject to subject. Regardless of the tissue obtained for grafting, the vascular plexus within the native tissue influences the degree of vascularization. Native vessels exposed on the surface of the graft improve the opportunity for graft take. Using a collagen based matrix which is initially avascular, allows for an accurate assessment of neo-vascularity, obviating the influence of any native vessels.

In a preferred embodiment, the grafts are mainly cellular (skin), rather than mostly acellular (dermis). Neovascularization in cellular grafts, while simultaneously deleting any effects of native vascularity, was demonstrated in Example 1, in which the biodegradable polymer matrices were seeded with cells experimentally, using a controlled environment with the same number of cells per implant.

In another aspect of the present invention, tissue neovascularization can be enhanced using transient expression of VEGF and vascular endothelial cells (EC) within the tissue that incorporate into blood capillaries. Various types of EC, including but not limited to, human umbilical vein EC (HUVEC), human dermal microvascular EC (HDMEC), bovine aortic EC (BAEC), bovine capillary EC (BCE), progenitor EC, and $CD34^+$ mononuclear cells can be used for angiogenesis and vasculogenesis. Gelatin, fibrin, collagen, fibronectin and Matrigel can be used as matrixes for 2D and 3D culture studies (Vailhe B, et al. In vitro models of vasculogenesis and angiogenesis. *Lab Invest.* 81: 439-52, 2001). However, cultured EC were rapidly undergoing apoptosis following implantation in vivo. The present invention overcomes this problem through the transient expression of VEGF which can act to prevent EC apoptosis in vitro and in vivo. Example 3 illustrates that transient expression of recombinant VEGF through adenovirus infection, for example, and implantation of vascular endothelial cells (EC), enhance the neovascularization of engineered muscle tissues.

The generation of new vessels should follow the kinetics of normal development in the vasculature. High concentration of VEGF may be required for the initial differentiation, proliferation, and recruitment of EC to form endothelial tubes and then subside to lower levels that are required for maturation and maintenance of the vessels. For this reason, regulated expression of VEGF is more appropriate for inducing neovascularization in bioengineered tissues. Adenovirus infection of cells permits temporal expression of viral-derived proteins and the duration of expression depends on the multiplicity of infection (MOI) and the cell type (Ragot T et al. *Nature.* 361: 647-50., 1993; Akli S, et al. *Nat Genet.* 3: 224-8., 1993; Le Gal La Salle G, et al. *Science.* 259: 988-90., 1993.). Large amount of VEGF were detected in conditioned media of infected primary myoblasts 10 days after infection with AdVEGF (see Example 3). However, the levels were dramatically reduced after 4 weeks and were undetectable after 10 weeks. VEGF expressing myoblasts formed tissue mass in vivo upon subcutaneous injection. Although tissue volumes decreased by about 40% after 1 week they remained largely unchanged in the next 7 weeks. In contrast, control myoblasts that were not infected with AdVEGF lost 80% of their volume in the first week and were undetectable by the third week. These results were accompanied by massive skin angiogenesis at the site of implantation and tissue neovascularization in mice injected with VEGF producing myoblasts but not in control myoblasts. These results indicate that transient delivery of VEGF to the newly formed tissue induces neovascularization and preserves tissue volumes over time. Since the goal of the study was to generate bioengineered muscle tissue we examined two muscle-related genes, Myosin heavy chain and MyoD. The former represents a functional muscle gene product whereas the latter is a transcription factor that regulates muscle development (Weintraub H, et al. *Science.* 251: 761-6., 1991). Myosin was consistently detected in large amounts in tissues formed by VEGF expressing myoblasts whereas in tissues from control myoblasts myosin was detected only at the first week. On the other hand, MyoD was abundant in tissues formed by VEGF expressing myoblasts in the first 3 weeks and then diminished. Since MyoD is one of the master regulators of muscle development its presence in the tissue is only required during the differentiation stage and not when the muscle tissue is mature (Weintraub H. *Cell.* 75: 1241-4., 1993). In tissues from control myoblasts MyoD was detected in the first week, probably due to its expression in cultured myoblast (Dalrymple K R, et al. *Differentiation.* 66: 218-26., 2000) but not at later time points. Taken together, the results indicate that the induction of neovascularization by VEGF supports the formation of muscle tissue from injected myoblasts.

In another embodiment, renal cells can be transfected to express an angiogenesis modulating agent. Renal cells could be easily differentiated from the native epithelial and mesenchymal cells, which could infiltrate the matrix. In addition, renal cells have been extensively characterized in vitro and in vivo (Amiel et al. *Urol Clin North Am* (1999) 26: 235); (Atala A. "Tissue engineering in the genitourinary system." In: *Synthetic biodegradable polymer scaffolds.* Boston Birkhuser, 1997); (Yoo et al. *J. Urol.* (1997) 157:208 (suppl)); Atala et al. *J. Urol* (1995) 153: 209A)). The use of renal cells to produce VEGF in vivo, as shown in Example 1, allow for the measurement of angiogenic and cellular parameters demonstrating the methods of this invention.

The microencapsulated engineered cells of the present invention are a novel system for the delivery of angiogenesis modulating agents. The encapsulation of these cells in alginate-PLL capsules protect the encapsulated cells from the host immune system, while allowing the constant release of the angiogenesis modulating agent as needed. Example 1 demonstrates that the engineered microcapsules were able to secrete VEGF protein at a steady state in vitro. When implanted in vivo, the engineered microcapsules showed a vascularization enhancing effect of the implanted matrix regions, with or without renal cells. The release of VEGF over a period of two weeks stimulated endothelial cell migration, cluster formation and newly formed capillaries at the implant sites. An increase in capillary-like structures was noted, particularly in the tissues surrounding the area of the injected microspheres. Immunocytochemical and histological analysis showed that endothelial cell migration and newly formed capillaries were organized around blood vessels in the skin and matrix implant regions on days 7 and 14 following implantation. These endothelial cell clusters were not detected in the control groups which did not receive the encapsulated cells.

CD-34 positive mononuclear blood cells (endothelial cell progenitors) isolated from human peripheral blood induce neovascularization. Fourteen percent of all CD31 positive capillaries contained the progenitors cells. By 6 weeks, the endothelial cell progenitors arrange into capillaries (Ashara et al. *Science* (1997) 275:964). The endothelial cell clusters detected in the matrices of this invention were consistent with endothelial cells progenitors, which migrate from existing blood vessels, due to the high levels of VEGF stimulation, and differentiate with time to mature endothelial cells responsible for typical blood vessel formation.

Example 1 also showed that the renal cells continued to expand in vitro within the matrix architecture. The renal cells were identified histologically, immunohistochemically, and by fluorescent labeling. Of specific interest, is the finding that cell expansion and migration within the matrix was more progressive in the experimental group which was exposed to the VEGF secreting encapsulated cells. These findings suggests that enhanced vascularization promotes proliferation and viability of cells within the graft.

IV. Transient Expression of Angiogenesis Modulating Agents

Unregulated VEGF expression has been shown to lead to the formation of vascular abnormalities, i.e. hemangiomas, or hemorrhage in tissues (Lee et al. *Circulation* (2000) 102(8): 898-901); Springer et al. *J Gene Med* (2000) 2(4):279-288). The consequences of long term release of VEGF systemically is also unknown and may play a role in pathological angiogenesis in vessel proliferative diseases, including tumor growth, diabetic retinopathy and progression of arteriosclerosis resulting from neovascularization of atherosclerotic plaques (Henry et al. *Curr Interv Cardiol Rep* (2000) 2(3): 228-241). Sustained overproduction of angiogenic factors such as VEGF may also result in deformed, nonfunctional blood vessels ((Lee et al. *Circulation* (2000) 102(8): 898-901); (Rinsch et al. *Gene Ther* (2001) 8(7): 523-533)). Because of such findings, a system of transient and local VEGF administration to promote localized angiogenesis with minimal systemic side effects is highly desired.

In one aspect of the present invention, cells are engineered to express angiogenesis modulating agents for a short time. In one embodiment, the angiogenesis modulating agent is expressed for less than 6 months. In a preferred embodiment, the angiogenesis modulating agent is expressed for less than one month. Preferably, the angiogenesis modulating agent is expressed less than 3 weeks. More preferably, the angiogenesis modulating agent is expressed for less than 7 days. Cells engineered to transiently express angiogenesis modulating agents, as disclosed by the present invention, is a needed alternative in therapeutic angiogenesis.

Muscle is a ubiquitous tissue throughout the human body, and any congenital and acquired conditions may affect its functionality. Growth and regeneration of muscle depends on satellite cells, which are able to multiply and generate new muscle fibers. In pathological situations, satellite cell function may be disrupted, leading to the connective tissue deposition and fibrosis. Satellite function may also be affected due to poor vascularization or cell loss secondary to trauma. The present invention involves the engineering of muscle tissue through autologous harvesting of cells, their expansion in vitro, transfecting a population of the harvested cells with the cDNA of an angiogenesis modulating agent, and the subsequent implantation in vivo into affective sites requiring repair or replacement.

Recent advances in our understanding of the angiogenic process and the isolation of potent and specific angiogenic factors have encouraged the therapeutic use of these growth factors (Koransky et al. *Trends Cardiovasc Med* (2002) 12(3): 108-114); (Soker et al. *World J. Urol* (2000) 18(1):10-18): (Lubiatowski, 2002). Treatment is divided into two approaches, therapeutic angiogenesis and therapeutic vasculogenesis. The first approach uses an angiogenic factor as pharmacological agents while therapeutic vasculogenesis illustrates the use of endothelial cells for revascularization (Nomi et al. *Mol Aspects Med* (2002) 23(6): 463). Evidence that VEGF is a specific endothelial cell growth factor has suggested its potential in therapeutic angiogenesis. VEGF is a major regulator of neovascularization under physiological and pathological condition and plays an important role in therapeutic angiogenesis. VEGF is widely expressed in different tissues by a variety of cell types and it is a potent angiogenic factor in a variety of in vivo models. VEGF expression is up-regulated in tissues undergoing vascularization during embryogenesis; it is a specific mitogen for endothelial cell and it stimulates endothelial cells to migrate and to forms tubes in vitro (Takeshita et al. *J. Clin Invest* (1994) 93(2) 662-670). In one aspect of this invention, VEGF is used as an angiogenesis modulating agent for muscle tissue engineering. In another aspect of this invention, VEGF is used as an angiogenesis modulating agent for organ augmentation. VEGF can be used to direct endothelial cells to the implantation site, where they then form structures that develop blood vessels. VEGF does not necessarily undergo any gene modification and has a limited lifetime.

The method and compositions of the present invention achieve an adequate magnitude and duration (less than 3 weeks) of VEGF expression that would allow for the survival of the implanted myoblasts without untoward consequences due to VEGF over expression. The transient expression of VEGF disclosed in the present invention is sufficient to stimulate blood vessel growth and to support survival of the injected adult myoblasts cells even after regression of VEGF expression. Transfection efficiencies of approximately 30% with the lipid-based transfection technique was achieved. Greater transfection efficiencies may be achieved with other transfection techniques known in the art, such as viral vectors, including replication-deficient adenoviruses. However, the immune-response that occurs after in vivo transfection with adenoviral vectors, particularly earlier-generation vectors, limits the duration of transgene expression and may be undesirable when the persistence of the transplanted cells is of paramount importance. RT-PCR, Western blot and fluorescence analyses in vitro and in vivo showed that the transfected plasmids, using the lipofection technique, were only expressed during the first week (See Example 2).

In one embodiment, myoblasts can be genetically engineered to secrete VEGF. As shown in Example 2, transfected myoblasts secreted $VEGF_{165}$ in vitro with a molecular weight of 28 and 23 kDa. Similar results have been reported in other studies and this may represent glycosylation variants of VEGF. In vivo, the tissue retrieved at different time points maintain its initial injected volume (0.8 cm$^3$). Histologic sections of the retrieved VEGF modified engineered muscle constructs show viable cells and a well-developed vascular network. In contrast, injection of the control cells producing monomeric non-functional VEGF resulted in a significant volume loss of the tissue and only minimal vascular recruitment. Example 2 demonstrates that the methods and compositions of the present invention can be used to generate well-vascularized muscle tissue using myoblasts that transiently express VEGF. Cells secreting non-functional VEGF were unable to recruit a sufficient vascular supply to allow for the adequate survival of the transplanted cells. Example 2 shows that VEGF not only increases the survival of injected cells, but is also necessary for formation of large tissue masses.

One aspect of the present invention relies upon the transfection of a plasmid encoding angiogenesis modulating agent cDNA yielding transient expression of the protein. Because VEGF is a very potent stimulator of angiogenesis, as well as vasculogenesis and blood vessel permeability, uncontrolled growth of blood vessels stimulated by chronic secretion of VEGF could lead to a pathological process. Chronic expression of VEGF has been shown to produce hemangiomas as well as hemorrhages, enhancement of tumor angiogenesis and death in animal studies.

The present invention allows localized neovascularization such that systemic effects are minimalized. In one embodiment, the amount of VEGF secreted and/or delivered to the target site can be controlled to minimize the potential deleterious effects on the surrounding tissues. Example 2 shows that localized angiogenesis is possible with a limited period of VEGF expression following injection of VEGF transfected cells. This transient VEGF secretion allowed growth of new vessels and sustained cell viability without any progression to hemangioma formation or hemorrhage.

In one aspect of the present invention, the gene for an angiogenesis modulating factor is transferred into cells, which are used for the creation of tissue in vivo. In one embodiment, the cells are immature cells. In another embodiment, the cells are autologous. In a preferred embodiment, the cells are primary cultures of muscle cells. Example 2 demonstrates the feasibility of VEGF gene transfer into primary cultures of muscle cells, which are subsequently used for the creation of well-vascularized muscle tissues in vivo. This approach has important implications in tissue engineering, such as the ability to transiently express VEGF in order to promote angiogenesis without deleterious effects of chronic expression, improvement of vascular supply to ischemic tissues, including cardiac and skeletal muscles and the generation of a vascular network in large solid engineered tissue organs and it could be employed for the repair and engineering of muscle structures in the genitourinary tract.

V. Isolation and Culture of Cells

Cells can be isolated from a number of sources, for example, from biopsies, or autopsies, a stem cell population that is programmed to differentiate into the desired organ cells, a heterologous cell population that has been encapsulated to render it non-immunogenic, xenogenic cells, and allogenic cells. Also within the scope of the invention are methods which involve transfecting the cell population with factors such as growth factors which improve tissue formation.

The isolated cells are preferably allogenic, autologous cells, obtained by biopsy from the subject. For example, kidney cells can also be derived from the subject's dysfunctional kidney and cultured in vitro. The biopsy can be obtained using a biopsy needle, or a rapid action needle which makes the procedure quick and simple. The area for biopsy can be treated with local anaesthetic with a small amount of lidocaine injected subcutaneously. The small biopsy core of the organ, e.g., a kidney can then be expanded and cultured in vitro, as described by Atala, et al., (1992) *J. Urol.* 148, 658-62; Atala, et al. (1993) *J. Urol.* 150: 608-12. Cells from relatives or other donors of the same species can also be used with appropriate immunosuppression.

Methods for the isolation and culture of cells are discussed in Fauza et al. (1998) *J. Ped. Surg.* 33, 7-12 and Freshney, Culture of Animal Cells, A Manual of Basic Technique, 2d Ed., A. R. Liss, Inc., New York, 1987, Ch. 9, pp. 107-126, incorporated herein by reference. Cells may be isolated using techniques known to those skilled in the art. For example, the tissue or organ can be disaggregated mechanically and/or treated with digestive enzymes and/or chelating agents that weaken the connections between neighboring cells making it possible to disperse the tissue into a suspension of individual cells without appreciable cell breakage. Enzymatic dissociation can be accomplished by mincing the tissue and treating the minced tissue with any of a number of digestive enzymes either alone or in combination. These include but are not limited to trypsin, chymotrypsin, collagenase, elastase, and/or hyaluronidase, DNase, pronase and dispase. Alternatively, mechanical disruption can be used and this can be accomplished by a number of methods including, but not limited to, scraping the surface of the organ, the use of grinders, blenders, sieves, homogenizers, pressure cells, or insonicators. For a review of tissue disaggregation techniques, see Freshney, (1987), Culture of Animal Cells. A Manual of Basic Technique, 2d Ed., A. R. Liss, Inc., New York, Ch. 9, pp. 107-126.

Preferred cell types include, but are not limited to, kidney cells, endothelial cells, heart cells, liver cells, pancreatic cells, spleen cells, urothelial cells, mesenchymal cells, smooth or skeletal muscle cells, myocytes (muscle stem cells), cardiac muscle cell, fibroblasts, chondrocytes, adipocytes, fibromyoblasts, and ectodermal cells, including ductile and skin cells, hepotocytes, epithelial cells, mesodermal cells, dermal cells, bladder cell, ureteral cell, gonadal cell, parenchymal cell, Islet cells, cells present in the intestine, and other parenchymal cells, osteoblasts and other cells forming bone or cartilage. In some cases, it may also be desirable to include nerve cells. In a preferred embodiment, kidney cells are isolated. Kidney cells from all developmental stages, such as, fetal, neonatal, juvenile to adult may be used. In another preferred embodiment, endothelial cells (EC) are isolated.

Once the tissue has been reduced to a suspension of individual cells, the suspension can be fractionated into subpopulations from which the cells elements can be obtained. This also may be accomplished using standard techniques for cell separation including, but not limited to, cloning and selection of specific cell types, selective destruction of unwanted cells (negative selection), separation based upon differential cell agglutinability in the mixed population, freeze-thaw procedures, differential adherence properties of the cells in the mixed population, filtration, conventional and zonal centrifugation, centrifugal elutriation (counterstreaming centrifugation), unit gravity separation, countercurrent distribution, electrophoresis and fluorescence-activated cell sorting. For a review of clonal selection and cell separation techniques, see Freshney, (1987), Culture of Animal Cells. A Manual of Basic Techniques, 2d Ed., A. R. Liss, Inc., New York, Ch. 11 and 12, pp. 137-168. For example, kidney renal cells may be enriched by fluorescence-activated cell sortings. Also, different regions of the renal cells may be sorted into separate sub-populations. For example, separate sub-populations of glomeruli cells, bowman's capsule cells, distil tubule cells proximal tubule cells, loop of Henlè cells and collective duct cells.

Cell fractionation may also be desirable to sort healthy cells from diseased cells, for example, when the donor has diseases such as cancer or metastasis of tumors. A cell population may be sorted to separate malignant cells or other tumor cells from normal noncancerous cells. The normal noncancerous cells, isolated from one or more sorting techniques, may then be used for organ augmentation.

Isolated cells can be cultured in vitro to increase the number of cells available for coating the matrix material. The use of allogenic cells, and more preferably autologous cells, is preferred to prevent tissue rejection. However, if an immunological response does occur in the subject after implantation of the artificial organ, the subject may be treated with immunosuppressive agents such as, cyclosporin or FK506, to reduce the likelihood of rejection. In certain embodiments, chimeric cells, or cells from a transgenic animal, can be coated onto the matrix material. Alternatively stem cells may be used.

Stem cells can also be used to generate the neomorphic organ augmenting structures of the invention. In one aspect of the invention, the stem cells can be genetically engineered to constituitively or transiently produce an angiogenesis modulating agent. Stem cells can be derived from a human donor, e.g., pluripotent hematopoietic stem cells, embryonic stem cells, adult somatic stem cells, and the like. The stem cells can be cultured in the presence of combinations of polypeptides, recombinant human growth and maturation promoting factors, such as cytokines, lymphokines, colony stimulating factors, mitogens, growth factors, and maturation factors, so as to differentiate into the desired cells type, e.g., renal cells, or cardiac cells. Method for stem cell differentiation into kidney and liver cells from adult bone marrow stem cells (BMSCs) are described for example by Forbes et al. (2002) *Gene Ther* 9:625-30. Protocols for the in vitro differentiation of embryonic stem cells into cells such as cardiomyocytes, representing all specialized cell types of the heart, such as atrial-like, ventricular-like, sinus nodal-like, and Purkinje-like cells, have been established (See e.g., Boheler et al. (2002) *Circ Res* 91:189-201). Multipotent stem cells from metanephric mesenchyme can generate at least three distinct cell types; glomerular, proximal and distal epithelia, i.e., differentiation into a single nephron segment (See e.g., Herzlinger et al. (1992) *Development* 114:565-72). Human and primate embryonic stem cells have been successfully differentiated in vitro into derivatives of all three germ layers, including beating cardiac muscle cells, smooth muscles, and insulin-producing cells, among others (Itskovitz-Eldor et al. *Mol. Med.* (2000) 5: 88-95; Schuldiner et al. *Proc. Natl. Acad. Sci. USA* (2000) 97: 11307-11312; Kaufman et al. *Blood* (1999) 94: (Suppl. 1, part 1 of 2) 34a.)

Stem cells capable of differentiating into specified tissues in vitro may be obtained from early-stage embryos. A staged developmental strategy may allow such cells to be isolated. In addition, nuclear transplantation can be used to generate cells that are histocompatible (Lanza et al. *Nature Biotechnology* 2002 20: 689-696). Furthermore, genetically engineered primordial or embryonic stem cells can be transplanted into a host animal such that the stem cells can differentiate into the needed cells and tissue. Following differentiation, the cells or tissue can be harvested using methods known in the art and used in the present invention. The host animal is preferably a developing fetus with an undeveloped immune system.

The organ cells, e.g., kidney cells, could be transfected with specific genes prior to coating the matrix material. The neomorphic organ augmenting structure could carry genetic information required for the long term survival of the host or the organ being augmented.

Isolated cells can be normal or genetically engineered to provide additional or normal function. For example, cells can be transfected with compounds that reduce the programs of the disease at the target site in the organ. Cells may also be engineered to reduce or eliminate an immune response in the host. For example, the expression of cell surface antigens such as class I and class II histocompatibility antigens may be suppressed. This may allow the transplanted cells to have reduced chance of rejection by the host. In addition, transfection could also be used for gene delivery. Methods for genetically engineering cells with retroviral vectors, polyethylene glycol, or other methods known to those skilled in the art can be used. These include using expression vectors which transport and express nucleic acid molecules in the cells (See Goeddel; *Gene Expression Technology: Methods in Enzymology* 185, Academic Press, San Diego, Calif. (1990).

The cells grown on the matrix may be genetically engineered to produce angiogenesis modulating agents or gene products beneficial to transplantation, e.g., anti-inflammatory factors, e.g., anti-GM-CSF, anti-TNF, anti-IL-1, and anti-IL-2. Alternatively, the endothelial cells may be genetically engineered to "knock out" expression of native gene products that promote inflammation, e.g., GM-CSF, TNF, IL-1, IL-2, or "knock out" expression of MHC in order to lower the risk of rejection. In addition, the cells may be genetically engineered for use in gene therapy to adjust the level of gene activity in a patient to assist or improve the results of tissue transplantation.

Methods for genetically engineering cells with retroviral vectors, polyethylene glycol, or other methods known to those skilled in the art can be used. These include using expression vectors which transport and express nucleic acid molecules in the cells. (See Geoddel; *Gene Expression Technology: Methods in Enzymology* 185, Academic Press, San Diego, Calif. (1990).

VI. Engineering Cells to Constitutively or Transiently Express an Angiogenesis Modulating Agent.

Vector DNA is introduced into prokaryotic or eukaryotic cells via conventional transformation or transfection techniques. Suitable methods for transforming or transfecting host cells can be found in Sambrook et al. *Molecular Cloning: A Laboratory Manual*, 3rd Edition, Cold Spring Harbor Laboratory press (2001), and other laboratory textbooks. The seeded cells can be engineered using a recombinant DNA construct containing the gene of interest that transforms or transfects the cells.

The sequences of the growth factors and angiogenesis modulating factors can be found in GenBank (i.e., the sequence of VEGF can be found at Accession No. P15692) Cloning vectors and protocols are well known in the art (See, for example, Promega Corp., Strategene, Clontech, Invitrogen). In one embodiment, the angiogenesis modulating factor is cloned into the expression vector pRc/CMV (Invitrogen). In a preferred embodiment, the expression vector pIRES2-EGFP (Clontech) is used for transient expression of the gene of interest.

Common transfection techniques include, but are not limited to the calcium phosphate method, DEAE-dextran, electroporation, or lipofection. Transfection efficiency using the calcium phosphate method can be improved using optimized culture conditions and liposome-based transfection reagent. LipofectAMINE (Gibco Life Techonology) is the preferred method of transfection yielding higher efficiency and less plate-to-plate variation with liposome-based reagents as compared to transfection with calcium phosphate. Protocols for transient and stable transfection are well known in the art (See Sambrok et al. supra.).

The transfected cells are encapsulated to all immunoprotection of the cell while still enabling the angiogenesis modulating agent to be secreted. The seeded matrix comprising the encapsulated transfected cells expresses the active gene product, such as an angiogenesis modulating agent or growth factor. The level of gene activity may be increased by either increasing the level of gene product present or by increasing the level of the active gene product which is present in the biomatrix comprising the matrix material and tissue, e.g., endothelial tissue layer or renal tissue layer. The biomatrix culture can express the active target gene product can then be implanted into the patient to enhance vascularization of the implanted matrix.

The biomatrix cultures containing such genetically engineered cells can then implanted into the subject to allow for the amelioration of the symptoms of the disease. The gene expression may be under the control of a non-inducible (i.e., constitutive) or inducible promoter. The level of gene expression and the type of gene regulation can be controlled depending upon the type of growth factor or angiogenesis modulation factor. For example, transient expression of VEGF may be beneficial to enhance angiogenesis while eliminating side effects caused by long term expression. Alternatively stable expression of a growth factor, such as bFGF, may be allow enhance angiogenesis with minimal side effects from long term expression.

VII. Matrix Materials

The methods and composition of the present invention are created using matrix materials as the substrate onto which cells are deposited, and on which cells grown and adhere. It is important to recreate, in culture, the cellular microenvironment found in vivo for the particular organ targeted for augmentation. Retaining an infra-structure that is similar or the same as an in vivo organ creates the optimum environment for cell-cell interactions, development and differentiation of cell populations. The extent to which the cells and tissue layers are grown prior to use in vivo may vary depending on the type of organ being augmented.

The invention provides a method of augmenting organ function using a matrix material that supports the maturation, development and differentiation, of additional cultured cells in vitro to form components of adult tissues analogous to their in vivo counterparts. The matrix allows optimum cell-cell interactions, thereby allowing a more natural formation of cellular phenotypes and a tissue microenvironment. The matrix also allows cells to continue to grow actively, proliferate and differentiate to produce a neomorphic organ augmenting structure that is also capable of supporting the growth, proliferation and differentiation of additional cultured cells populations.

Cells grown on the matrix materials, in accordance with the present invention, may grow in multiple layers, forming a cellular structure that resembles physiologic conditions found in vivo. The matrix can support the proliferation of different types of cells and the formation of a number of different tissues. Examples include, but are not limited to, kidney, heart, skin, liver, pancreas, adrenal and neurological tissue, as well as tissues of the gastrointestinal and genitourinary tracts, and the circulatory system.

The seeded matrices of the invention can be used in a variety of applications. For example, the matrices can be implanted into a subject. Implants, according to the invention, can be used to replace or augment existing tissue. For example, to treat a subject with a kidney disorder by augmenting the natural kidney. The subject can be monitored after implantation of the matrix implant, for amelioration of the kidney disorder. In one embodiment, encapsulated cells genetically engineered to produce angiogenesis modulating agents can be co-implanted with the matrix thereby enhancing angiogenesis. In another embodiment, the genetically engineered cells can be suspended in a pharmaceutically acceptable carrier such that the angiogenesis modulating agent secreting cells commingle with the cells of the matrix implant.

Also within the scope of the invention are compositions and methods of organ augmentation using a neomorphic organ augmenting structure with one population of cultured cells to produce a tissue layer from the single population. Alternatively, the neomorphic organ augmenting structure can comprise multiple layers derived from at least two different cell populations, e.g., a smooth muscle cell population, and a urothelial cell population. In a preferred embodiment, the neomorphic organ augmenting structure comprises an endothelial layer with a primitive vascular system and at least one other tissue layer derived from parenchyma cells.

Once perfused onto the matrix material, the endothelial cells will proliferate and develop on the polymeric matrix to form an endothelial tissue layer. During in vitro culturing, the endothelial cells develop and differentiate to produce a primitive vascular system which is capable of developing into a mature vascular system, and is also capable of further development and is also capable of supporting the growth of parenchyrna cells perfused into the matrix material. Importantly, because the polymeric matrix has an infra-structure that permits culture medium to reach the endothelial tissue layer and the parenchyma cells, the different cell populations continue to grow, divide, and remain functionally active. The parenchyma cells proliferate, and differentiate into neomorphic organ structures that have a morphology which resembles the analogous structure in vivo. The extent to which the endothelial cells and parenchyma cells are grown prior to use in vivo may vary depending on the type of organ being augmented. Organs that can be augmented include, but are not limited to, heart, kidney, liver, pancreas, spleen, bladder, ureter and urethra.

(i) Polymeric Matrices

In a preferred embodiment, the matrix material is a polymeric matrix. Examples of suitable polymers include, but are not limited to, collagen, poly(alpha esters) such as poly(lactate acid), poly(glycolic acid), polyorthoesters and polyanhydrides and their copolymers, cellulose ether, cellulose, cellulosic ester, fluorinated polyethylene, phenolic, poly-4-methylpentene, polyacrylonitrile, polyamide, polyamideimide, polyacrylate, polybenzoxazole, polycarbonate, polycyanoarylether, polyestercarbonate, polyether, polyetherketone, polyetherimide, polyetherketone, polyethersulfone, polyethylene, polyfluoroolefin, polylmide, polyolefin, polyoxadiazole, polyphenylene oxide, polyphenylene, sulfide, polypropylene, polystyrene, polysulfide, polysulfone, polytetrafluoroethylene, polythioether, polytriazole, polyurethane, polyvinylidene fluoride, regenerated cellulose, urea-formaldehyde, or copolymers or physical blends of these materials.

Polymers, such as polyglycolic acid, which is a suitable biocompatible structures for producing an organ augmenting structure. The biocompatible polymer may be shaped using methods such as, solvent casting, compression molding, filament drawing, meshing, leaching, weaving and coating.

In solvent casting, a solution of one or more polymers in an appropriate solvent, such as methylene chloride, is cast as a branching pattern relief structure. After solvent evaporation, a thin film is obtained.

In compression molding, a polymer is pressed at pressures up to 30,000 pounds per square inch into an appropriate pattern. Filament drawing involves drawing from the molten polymer and meshing involves forming a mesh by compressing fibers into a felt-like material.

In leaching, a solution containing two materials is spread into a shape close to the final form of the organ. Next a solvent is used to dissolve away one of the components, resulting in pore formation (See Mikos, U.S. Pat. No. 5,514,378, hereby incorporated by reference).

In nucleation, thin films in the shape of the organ is exposed to radioactive fission products that create tracks of radiation damaged material. Next, the polycarbonate sheets are etched with acid or base, turning the tracks of radiation-damaged material into pores. Finally, a laser may be used to shape and burn individual holes through many materials to form an organ structure with uniform pore sizes.

The polymeric matrix can be fabricated to have a controlled pore structure that allows nutrients from the culture medium to reach the deposited cell population, but prevent cultured cells from migrating through the pores. In vitro cell attachment and cell viability can be assessed using scanning electron microscopy, histology and quantitative assessment with radioisotopes.

The polymeric matrix can be shaped into any number of desirable configurations to satisfy any number of overall system, geometry or space restrictions. The polymeric matrix can be shaped to different sizes to conform to the organs of different sized patients. The polymeric matrix may also be shaped to facilitate special needs of a patient, for example, a disabled patient, who may have a different abdominal cavity space may require a organ or part of an organ reconstructed to adapt to fit the space.

In other embodiments, the polymeric matrix is used for the treatment of laminar structures in the body such as urethra, vas deferens, fallopian tubes, lacrimal ducts. In those applications the polymeric substrate can be shaped as a hollow tube.

The neomorphic organ augmenting structure of the invention, functioning to augment an organ, can be flat, tubular, or of complex geometry. The shape of the organ will be decided by its intended use. The artificial organ can be implanted to repair, augment, or replace diseased or damaged parts of organs. Flat sheets or wafers may be used. The flat sheets can be shaped to a desired shape and geometry to fit within the target site of an organ, e.g., rolled into a cylinder or tube. Tubular grafts may be used, for example, to replace cross sections of tubular organs such as esophagus, trachea, intestine, and fallopian tubes. These organs have a basic tubular shape with an outer surface and luminal surface.

A polymeric matrix can be permeated with a material, for example liquified copolymers (poly-DL-lactide co-glycolide 50:50 80 mg/ml methylene chloride) to alter its mechanical properties. This can be performed by coating one layer, or multiple layers until the desired mechanical properties are achieved. The size of the polymeric matrix is determined based on the extent of organ augmentation required. For example, the matrix can dimensions of about 1 mm length×1 mm width×1 mm depth. The shape and size of the matrix depends on the region of the organ being augmented.

In one embodiment, the organ being augmented is a kidney, and the matrix can be a flat piece with dimensions of about 1 cm×1 cm and a thickness less than about 1 mm. Preferably, the length of greatest dimension of the matrix is greater than 0.2 mm and less than 100 mm, more preferably ranging from about 0.50 mm to about 30 mm. In a preferred embodiment, the shape of the mini-matrix is substantially flat and has a ratio of its greatest dimension to its thickness of greater than 5:1, more preferably greater than 10:1.

In another embodiment, the polymeric matrix can be rolled into a tube after the cells have been seeded to provide a larger volume of the organ structure. The size and shape of the polymeric matrix can be a disc, a wafer, a rolled wafer, a square, rectangle and the like. The configuration of the polymeric matrix is determined based on the area being augmented and, the organ being augmented. The size and shape of the polymeric matrix are selected such that the neomorphic organ augmenting structure that is produced has a ratio of its greatest dimension to its thickness of greater than 5:1, more preferably greater than 10:1.

In one embodiment, the augmenting organ structure an be used to augment organs comprising multiple layers, e.g., a bladder. This can be performed by using one side of the polymeric matrix to create a tissue layer by coating one side of the polymeric matrix with a suspension of a first homogenous cell population, e.g., renal cells. The first homogenous cell suspension is incubated in culture medium until the cells develop and proliferate to produce a monolayer and cells of the monolayer attach to the polymeric matrix. Once the monolayer is established, the first homogenous cell suspension is deposited over the first monolayer, and the cells are cultured until they develop and proliferate to produce second monolayer of cells over the first monolayer, thereby producing a bilayer. The process is repeated until a polylayer comprising multiple layers of the first homogenous cell population is generated. The polylayer is cultured to produce a tissue layer with morphological and functional characteristics that allow it to differentiate into an organ augmenting structure.

In another embodiment, both sides of the polymeric matrix are used to create a polylayer of a homogenous cell population. This is performed by coating one side of the polymeric matrix with a suspension of a homogenous cell population, e.g., renal cells, and culturing the cells until they develop into a monolayer. Repeating the procedure on the opposite side of the polymeric matrix. The process is repeated on both sides of the polymeric matrix until a polylayer comprising multiple layers of the homogenous cell population is generated on both sides of the matrix. The polymeric matrix comprising the polylayers on both sides is cultured to produce a tissue layer with morphological and functional characteristics that allow it to differentiate into an organ augmenting structure. In yet another embodiment, both sides of the polymeric matrix can be used to create polylayers of different cell populations. This is performed by coating one side of the polymeric matrix with a suspension of a first homogenous cell population, e.g., endothelial cells, and culturing the cells until they develop into a monolayer. Repeating the procedure on the opposite side of the polymeric matrix with a different homogenous cell population, e.g., renal cells.

In one embodiment, the organ being augmented is the kidney. The organ augmenting structure is created by using renal cells, or an isolated populations of distil tubule cells, proximal tubule cells, or glomeruli cells seeded in or on a matrix material. The kidney can be surgically opened along its longitudinal axis, and the neomorphic organ augmenting structure is placed in at least one target site in the kidney. In another embodiment, a plurality of neomorphic organ augmenting structures can be created and added at multiple target sites within the kidney. The number of neomorphic organ augmenting structure to be added depends of the extend of damage to the kidney. For example, if half of the upper half of the kidney is damaged, then about 1 to about 10 augmenting constructs in the form of wafers can be positioned equally along the upper half of the kidney. The number of augmenting constructs to be implanted also depends on the size of the wafers used to create them. If the wafers are of large dimension e.g., 1 cm×1 cm×1 cm, then a fewer number of wafers are needed to augment the upper half of the kidney. Alternatively, if the wafers are small e.g., 1 mm×1 mm×1 mm, then many of these are needed to augment the same upper half of the kidney.

(ii) Hydrogels

In one embodiment, the matrix material is a hydrogel composed of crosslinked polymer networks which are typically insoluble or poorly soluble in water, but can swell to an equilibrium size in the presence of excess water. For example, the cells can be placed in a hydrogel and the hydrogel injected into desired locations within the organ. In one embodiment, the cells can be injected with collagen alone. In another embodiment, the cells can be injected with collagen and other hydrogels. The hydrogel compositions can include, without limitation, for example, poly(esters), poly(hydroxy acids), poly(lactones), poly(amides), poly(ester-amides), poly (amino acids), poly(anhydrides), poly(ortho-esters), poly (carbonates), poly(phosphazines), poly(thioesters), polysaccharides and mixtures thereof. Furthermore, the compositions can also include, for example, a poly(hydroxy) acid including poly(alpha-hydroxy) acids and poly(beta-hydroxy) acids. Such poly(hydroxy) acids include, for example, polylactic acid, polyglycolic acid, polycaproic acid, polybutyric acid, polyvaleric acid, and copolymers and mixtures thereof. Due to the unique properties of hydrogels and their potential applications in such areas as controlled drug delivery, various types of hydrogels have been synthesized and characterized. Most of this work has focused on lightly cross-linked, homogeneous homopolymers and copolymers.

The bulk polymerization, i.e., polymerization in the absence of added solvent, of monomers to make a homogeneous hydrogel produces a glassy, transparent polymer matrix which is very hard. When immersed in water, the glassy matrix swells to become soft and flexible. Porous hydrogels are usually prepared by a solution polymerization technique, which entails polymerizing monomers in a suitable solvent. The nature of a synthesized hydrogel, whether a compact gel or a loose polymer network, depends on the type of monomer, the amount of diluent in the monomer mixture, and the amount of crosslinking agent. As the amount of diluent (usually water) in the monomer mixture increases, the pore size also increases up to the micron range. Hydrogels with effective pore sizes in the 10-100 nm range and in the 100 nm-10 micrometer range are termed "microporous" and "macroporous" hydrogels, respectively. The microporous and macroporous structures of hydrogels can be distinguished from those of non-hydrogel porous materials, such as porous polyurethane foams. In the plastic foam area, micro- and macro-pores are indicated as having pores less than 50 micrometers and pores in the 100-300 micrometer range, respectively. One of the reasons for this difference is that hydrogels with pores larger than 10 micrometers are uncommon, while porous plastics having pores in the 100-300 micrometer range are very common.

Microporous and macroporous hydrogels are often called polymer "sponges." When a monomer, e.g., hydroxyethyl methacrylate (HEMA), is polymerized at an initial monomer concentration of 45 (w/w) % or higher in water, a hydrogel is produced with a porosity higher than the homogeneous hydrogels. The matrix materials of present invention encompass both conventional foam or sponge materials and the so-called "hydrogel sponges." For a further description of hydrogels, see U.S. Pat. No. 5,451,613 (issued to Smith et al.).

(iii) Decellularized Parts of Biostructures

In yet another embodiment, the neomorphic organ augmenting structure can be created using parts of a natural decellularized organ. Biostructures, or parts of organs can be decellularized by removing the entire cellular and tissue content from the organ. The decellularization process comprises a series of sequential extractions. One key feature of this extraction process is that harsh extraction that may disturb or destroy the complex infra-structure of the biostructure, be avoided. The first step involves removal of cellular debris and solubilization of the cell membrane. This is followed by solubilization of the nuclear cytoplasmic components an the nuclear components.

Preferably, the biostructure, e.g., part of an organ is decellularized by removing the cell membrane and cellular debris surrounding the part of the organ using gentle mechanical disruption methods. The gentle mechanical disruption methods must be sufficient to disrupt the cellular membrane. However, the process of decellularization should avoid damage or disturbance of the biostructure's complex infra-structure. Gentle mechanical disruption methods include scraping the surface of the organ part, agitating the organ part, or stirring the organ in a suitable volume of fluid, e.g., distilled water. In one preferred embodiment, the gentle mechanical disruption method includes stirring the organ part in a suitable volume of distilled water until the cell membrane is disrupted and the cellular debris has been removed from the organ.

After the cell membrane has been removed, the nuclear and cytoplasmic components of the biostructure are removed. This can be performed by solubilizing the cellular and nuclear components without disrupting the infra-structure. To solubilize the nuclear components, non-ionic detergents or surfactants may be used. Examples of non-ionic detergents or surfactants include, but are not limited to, the Triton series, available from Rohm and Haas of Philadelphia, Pa., which includes Triton X-100, Triton N-101, Triton X-114, Triton X-405, Triton X-705, and Triton DF-16, available commercially from many vendors; the Tween series, such as monolaurate (Tween 20), monopalmitate (Tween 40), monooleate (Tween 80), and polyoxethylene-23-lauryl ether (Brij. 35), polyoxyethylene ether W-1 (Polyox), and the like, sodium cholate, deoxycholates, CHAPS, saponin, n-Decyl β-D-glucopuranoside, n-heptyl β-D glucopyranoside, n-Octyl α-D-glucopyranoside and Nonidet P-40.

One skilled in the art will appreciate that a description of compounds belonging to the foregoing classifications, and vendors may be commercially obtained and may be found in "Chemical Classification, Emulsifiers and Detergents", McCutcheon's, Emulsifiers and Detergents, 1986, North American and International Editions, McCutcheon Division, MC Publishing Co., Glen Rock, N.J., U.S.A. and Judith Neugebauer, A Guide to the Properties and Uses of Detergents in Biology and Biochemistry, Calbiochem. R., Hoechst Celanese Corp., 1987. In one preferred embodiment, the non-ionic surfactant is the Triton. series, preferably, Triton X-100.

The concentration of the non-ionic detergent may be altered depending on the type of biostructure being decellularized. For example, for delicate tissues, e.g., blood vessels, the concentration of the detergent should be decreased. Preferred concentrations ranges non-ionic detergent can be from about 0.001 to about 2.0% (w/v). More preferably, about 0.05 to about 1.0% (w/v). Even more preferably, about, 0.1% (w/v) to about 0.8% (w/v). Preferred concentrations of these range from about 0.001 to about 0.2% (w/v), with about 0.05 to about 0.1% (w/v) particular preferred.

The cytoskeletal component, comprising consisting of the dense cytoplasmic filament networks, intercellular complexes and apical microcellular structures, may be solubilized using alkaline solution, such as, ammonium hydroxide. Other alkaline solution consisting of ammonium salts or their derivatives may also be used to solubilize the cytoskeletal components. Examples of other suitable ammonium solutions include ammonium sulphate, ammonium acetate and ammonium hydroxide. In a preferred embodiment, ammonium hydroxide is used.

The concentration of the alkaline solutions, e.g., ammonium hydroxide, may be altered depending on the type of biostructure being decellularized. For example, for delicate tissues, e.g., blood vessels, the concentration of the detergent should be decreased. Preferred concentrations ranges can be from about 0.001 to about 2.0% (w/v). More preferably, about 0.005 to about 0.1% (w/v). Even more preferably, about, 0.01% (w/v) to about 0.08% (w/v).

The decellularized, lyophilized structure may be stored at a suitable temperature until required for use. Prior to use, the decellularized structure can be equilibrated in suitable isotonic buffer or cell culture medium. Suitable buffers include, but are not limited to, phosphate buffered saline (PBS), saline, MOPS, HEPES, Hank's Balanced Salt Solution, and the like. Suitable cell culture medium includes, but is not limited to, RPMI 1640, Fisher's, Iscove's, McCoy's, Dulbecco's medium, and the like.

VIII. Cell Adhesion

In some embodiments, attachment of the cells to the matrix material is enhanced by coating the matrix material with compounds such as basement membrane components, agar, agarose, gelatin, gum arabic, collagens types I, II, III, IV, and V, fibronectin, laminin, glycosaminoglycans, mixtures thereof, and other hydrophilic and peptide attachment materials known to those skilled in the art of cell culture. A preferred material for coating the matrix material is collagen.

In other embodiments, matrix materials can be treated with factors or drugs prior to implantation, before or after the matrix material is coated with cultured cells, e.g., to promote the formation of new tissue after implantation. Factors including drugs, can be incorporated into the matrix material or be provided in conjunction with the matrix material. Such factors will in general be selected according to the tissue or organ being reconstructed or augmented, to ensure that appropriate new tissue is formed in the engrafted organ or tissue (for examples of such additives for use in promoting bone healing, (see, e.g., Kirker-Head, (1995) Vet. Surg. 24: 408-19). For example, when matrix materials are used to augment vascular tissue, vascular endothelial growth factor (VEGF), can be employed to promote the formation of new vascular tissue (see, e.g., U.S. Pat. No. 5,654,273 issued to Gallo et al.). Other useful additives include antibacterial agents such as antibiotics.

IX. Establishment of an Endothelial Tissue Layer

In one aspect, the invention pertains to using a cultured population of endothelial cells perfused on, or in the polymeric matrix material, or part of a decellularized organ, such that the endothelial cells grow and develop to produce a primitive vascular system. The endothelial cells may be derived from organs, such as, skin, liver, and pancreas, which can be obtained by biopsy (where appropriate) or upon autopsy. Endothelial cells can also be obtained from any appropriate cadaver organ. The endothelial cells can be expanded by culturing them in vitro to the desired cell density prior to infusion into the matrix material.

Endothelial cells may be readily isolated by disaggregating an appropriate organ, or part of an organ or tissue which is to serve as the source of the cells. This may be accomplished using techniques known to those skilled in the art. For example, the tissue or organ can be disaggregated mechanically and/or treated with digestive enzymes and/or chelating agents that weaken the connections between neighboring cells making it possible to disperse the tissue into a suspension of individual cells without appreciable cell breakage.

Enzymatic dissociation can be accomplished by mincing the tissue and treating the minced tissue with any of a number of digestive enzymes either alone or in combination. These include, but are not limited to, trypsin, chymotrypsin, collagenase, elastase, and/or hyaluronidase, DNase, pronase, and dispase. Mechanical disruption can also be accomplished by a number of methods including, but not limited to, the use of grinders, blenders, sieves, homogenizers, pressure cells, or insonators to name but a few. (See e.g. Freshney, (1987) Culture of Animal Cells. A Manual of Basic Technique, 2d Ed., A. R. Liss, Inc., New York, Ch. 9, pp. 107-126.)

After reducing the tissue to a suspension of individual cells, the suspension can be fractionated into subpopulations from which the endothelial cells can be obtained. This also may be accomplished using standard techniques for cell separation including, but not limited to, cloning and selection of specific cell types, selective destruction of unwanted cells (negative selection), separation based upon differential cell agglutinability in the mixed population, freeze-thaw procedures, differential adherence properties of the cells in the mixed population, filtration, conventional and zonal centrifugation, centrifugal elutriation (counterstreaming centrifugation), unit gravity separation, countercurrent distribution, electrophoresis and fluorescence-activated cell sorting. (See e.g. Freshney, (1987) Culture of Animal Cells. A Manual of Basic Techniques, 2d Ed., A. R. Liss, Inc., New York, Ch. 11 and 12, pp. 137-168.)

The growth of cells in the matrix material, e.g., polymeric matrix, may be enhanced by adding, or coating the matrix material with proteins (e.g., collagens, elastic fibers, reticular fibers) glycoproteins, glycosaminoglycans (e.g., heparan sulfate, chondroitin-4-sulfate, chondroitin-6-sulfate, dermatan sulfate, keratin sulfate, etc.), a cellular matrix, and/or other materials.

After perfusion of the endothelial cells, the matrix material should be incubated in an appropriate nutrient medium. Many commercially available media such as RPMI 1640, Fisher's, Iscove's, McCoy's, Dulbecco's medium, and the like, may be suitable for use. The culture medium should also be changed periodically to remove the used media, depopulate released cells, and add fresh media. It is important to grow the endothelial cells to a stage where an endothelial tissue layer comprising a primitive vascular system has developed prior to perfusion of the endothelial tissue layer with the parenchyma cells.

X. Perfusion of Parenchyma Cells onto Matrix Material Endothelial Layer

Once the endothelial tissue layer has reached the appropriate degree of growth and developed to produce a primitive vascular system, additional populations of cultured cells such as parenchymal cells can be perfused onto the endothelial tissue layer. Parenchyma cells perfused onto the endothelial tissue can be incubated to allow the cells to adhere to the endothelial tissue layer. The parenchyma cells can be cultured in vitro in culture medium to allow the cells to grow and develop until the cells resemble a morphology and structure similar to the that of the native tissue. Growth of parenchyma cells on the endothelial tissue layer results in the differentiation of parenchyma cells into the appropriate neomorphic organ augmenting structures.

Alternatively, after perfusing the parenchyma cells, the matrix can be implanted in vivo without prior in vitro culturing of the parenchyma cells. The parenchyma cells chosen for perfusion will depend upon the organ being augmented. For example, augmentation of a kidney will involve infusing cultured endothelial cells into or onto a matrix material, which is cultured until they develop into endothelial tissue layer comprising a primitive vascular system. The endothelial tissue can then be perfused with cultured kidney cells and cultured in vitro until the kidney cells begin to differentiate to form nephron structures.

The parenchyma cells may be obtained from cell suspensions prepared by disaggregating the desired tissue using standard techniques as described above. The cells may then be cultured in vitro to a desired density. After attaining the desired density, the cultured cells can be used to perfuse the matrix material with the endothelial tissue layer. The cells will proliferate, mature, and differentiate on the endothelial tissue layer. The choice of parenchyma cells will depend on the organ being augmented for example, when augmenting a kidney, the matrix material, e.g., a polymeric matrix and endothelial tissue layer is perfused with cultured kidney cells. When augmenting an liver, the polymeric matrix and endothelial tissue layer is perfused with cultured hepatocytes. When augmenting a pancreas, the polymeric matrix and endothelial tissue layer is perfused with cultured pancreatic endocrine cells. When augmenting a pancreas, the polymeric matrix and endothelial tissue layer is perfused with cultured pancreatic endocrine cells. When augmenting a heart, the polymeric matrix and endothelial tissue layer is perfused with cultured cardiac cells. For a review of methods which may be utilized to obtain parenchymal cells from various tissues, see, Freshney, (1987) Culture of Animal Cells. A Manual of Basic Technique, 2d Ed., A. R. Liss, Inc., New York, Ch. 20, pp. 257-288. Cells are cultured until they differentiate to produce neomorphic organ augmenting structures that resemble the morphology of the native in vivo tissue Growth factors and regulatory factors can be added to the media to enhance, alter or modulate proliferation and cell maturation and differentiation in the cultures. The growth and activity of cells in culture can be affected by a variety of growth factors such as insulin, growth hormone, somatomedins, colony stimulating factors, erythropoietin, epidermal growth factor, hepatic erythropoietic factor (hepatopoietin), and liver-cell growth factor. Other factors which regulate proliferation and/or differentiation include prostaglandins, interleukins, and naturally-occurring chalones.

XI. Creation of Three-Dimensional Biomatrices

In one aspect, the invention pertains to creating three-dimensional biomatrices, or organ augmenting structures/contructs. In one embodiment, the organ augmenting structures are created to address a specific disease or disorder that disrupts the function of the organ. For example, an organ augmenting structures can be a specific augmenting structure created to augment, and thereby ameliorate, glomerulopathies associated with abnormal glomeruli function (e.g., glomerulerulopathies, such as primary glomerulerulopathies associated with impaired glomeruli filtration (e.g., acute nephritic syndrome, rapidly progressive glomerulonephritis (RPGN), glomeruli sclerosis, nephrotic syndrome, asymptomatic abnormalities of the urinary sediment (hepaturia, proteinuria), and chornic glomerulonephritis), or secondary glomerulerulopathies, associated with systemic disease (e.g., diabetic nephropathy and immunologically mediated multisystem disease). The organ augmenting structures can be created using an isolated population of glomeruli cells that are grown to a tissue layer, and then the construct implanted to treat glomeruli sclerosis. In another example, the organ augmenting structures can be created using an isolated population of tubule cells to augment, and thereby ameliorate tubular disorder such as proximal tubule dysfunction andrenal tubular acidosis. This allows the methods and compositions of the invention to be used to specific disorders and pathologies associated with particular regions of the nephron.

Proximal tubule dysfunction may manifest aselective reabsorption defects leading to hypokalemia, aminoaciduria, glycosuria, phosphaturia, uricosuria, or bicarbonaturia. Renal tubular acidosis (RTA) results due to a defect in the reabsorption of filtered $HCO_3$, the excretion of H, or both. Renal tubular acidosis is characteristically associated with hyperchloremia and a normal glomerular function. RTA can be classified as Distal RTA (RTA-1), Proximal RTA (RTA-2) and hyperkalemic RTA (RTA-4). The last one is seen in many hyperkalemic states and the defect is characterized by the inability of the tubule to excrete enough $NH_4$ as a direct consequence of increased cellular stores of K.

In another embodiment, the organ augmenting structures can be a general augmenting structure created using a mixture of cells isolated from the organ being augmented. For example, an neomorphic organ augmenting structures seeded with renal cells comprising a mixture of distil tubule cells, proximal tubule cells, loop of Henle cells, and glomeruli cells.

In another embodiment, the augmenting construct can be used to augment heart function. In this example, the neomorphic organ augmentings structures can be created by seeding the matrix material with a population of myocardial cells.

In another embodiment, the augmenting construct can be used to augment bladder function. In this example, the augmenting construct can be created by seeding the matrix material with an isolated population of urothelial cells, or a population of cells comprising a mixture of smooth muscle cells and urothelial cells.

The biomatrices comprise a matrix material that as been perfused with at least one population of cultured cells, and incubated such that the dispersed cell population until it forms a monolayer and further incubating the cultured cells until they form a polylayer made up of multiple monolayers of cells, and eventually a tissue layer, e.g., renal tissue layer, or an endothelial layer with a primitive vascular system.

The sustained active proliferation of tissue layer eventually leads to the tissue layer resembling the equivalent parenchyma tissue of an in vivo organ. This may be due, in part, by the method of producing the polylayers. Polylayers are produced by culturing a first homogenous cell population one layer at a time on the matrix material until the cells of each layer are actively proliferating. The polylayers are incubated until the cells develop and proliferate to resemble the structure and morphology of the equivalent parenchyma tissue of an in vivo organ.

Polylayers developed by the method of the invention therefore produce proteins, growth factors and regulatory factors necessary to support the long term proliferation of the homogenous cell population. After the first polylayer has been established, this provides the surface for producing the second polylayer. The second polylayer comprises a second homogenous cell population that is different from the first homogenous cell population. The second polylayer is developed by culturing the second homogenous cell population one layer at a time until the cells of each layer are actively proliferating to produce a polylayer of cells, and eventually a tissue layer.

This tissue layer is capable of differentiating into a organ augmenting structure with further in vitro incubation, or in vivo incubation. The growth of cells in the tissue layer may be further enhanced by adding factors such as nutrients, growth factors, cytokines, extracellular matrix components, inducers of differentiation, products of secretion, immunomodulators, biologically-active compounds which enhance or allow growth of the cellular network or nerve fibers proteins, glycoproteins, and glycosaminoglycans.

In one embodiment, the matrix material used to create the biomatrix is a polymeric matrix. The tissue layer can be created on one side of the polymeric matrix, or both sides of the polymeric matrix until a tissue layer with the morphology and histology that allows differentiation into a organ augmenting structure is produced. In another embodiment, the polymeric matrix is a hydrogel into which a cultured cell population has been mixed. The cells are incubated in the hydrogel until they form a tissue layer that can differentiate into a organ augmenting structure.

XII. Implantation of the Three-Dimensional Biomatrix

The three-dimensional biomatrix or organ augmenting structures an be implanted into an organ requiring augmentation using standard surgical procedures. These surgical procedures may vary according to the organ being augmented. For kidney implantation, it may be desirable to implant a series of three-dimensional biomatrices into incisions formed along the avascular plane of the kidney, or the least vascular region of an organ. In other applications, the constructs of the invention can be introduced by less invasive procedures, e.g., via a cannula, needle, trocar or catheter-type instrument.

XIII. Uses

The compositions and methods of this invention have utility in research and drug development, as well as in wound treatment, surgery, tissue engineering, organ transplantation, and in the treatment of angiogenic disorders. The present invention allows growth factors and angiogenesis modulating agents to be delivered locally both continously and transiently. The invention could be used to modify or reduce scar tissue, speed up wound healing, and enhance tissue generation in problem wounds.

The methods and compositions of this invention provide the ability to successfully generate new tissue, augment organ function, and preserve the viability of impaired tissues, such as traumatically injured tissues or ischemic tissues. The present invention may enhance the viability of tissue, either through improving its vascular supply or the development of more functional tissue. The present invention may be useful to enhance a local wound to allow simple closure, either through skin grafting, or endogenous healing.

The methods and compositions of this invention can also be used in the treatment of ischemic ulcers or macular degeneration due to peripheral vascular disease, diabetes, aging and radiation necrosis. The present invention also finds use in enhancing microvascular tissue transfer which could be used to minimize scarring following surgery, plastic surgery, and prosthetic implants.

The methods and composition of the invention can also be used to augment organ function in a variety of organs.

(i) Kidney

In one embodiment, the invention pertains to methods and compositions for augmenting kidney function. Since virtually all kidney disease can cause renal failure, the major focus of treatment in most cases is to preserve kidney function. A subject typically has more kidney functioning power than necessary and most kidney diseases do not cause noticeable problems or symptoms until 90 percent of renal function is lost. Accordingly, the methods and compositions of the invention can be used to augment kidney function of a kidney in which at least about 2% function, preferably about 5% function, more preferably about 10% function, even more preferably about 15, 20, 25, 30, 35, 40, 45, 50, 55, 60, 65, 70, 75, 80, 85, 90% function. The methods and compositions of the invention can be used to ameliorate the symptoms of both acute and chronic renal failure. Kidney diseases that can be augmented include, but are not limited to, (for example, glomerulerulopathies, such as primary glomerulerulopathies associated with impaired glomeruli filtration (e.g., acute nephritic syndrome, rapidly progressive glomerulonephritis (RPGN), glomeruli sclerosis, nephrotic syndrome, asymptomatic abnormalities of the urinary sediment (hepaturia, proteinuria), and chornic glomerulonephritis), or secondary glomerulerulopathies, associated with systemic disease (e.g., diabetic nephropathy and immunologically mediated multisystem disease). This allows the methods and compositions of the invention to be used to specific disorders and pathologies associated with particular regions of the nephron. Proximal tubule dysfunction may manifest aselective reabsorption defects leading to hypokalemia, aminoaciduria, glycosuria, phosphaturia, uricosuria, or bicarbonaturia. Renal tubular acidosis (RTA) results due to a defect in the reabsorption of filtered $HCO_3$, the excretion of H, or both. Renal tubular acidosis is characteristically associated with hyperchloremia and a normal glomerular function. RTA can be classified as Distal RTA (RTA-1), Proximal RTA (RTA-2) and hyperkalemic RTA (RTA4). The last one is seen in many hyperkalemic states and the defect is characterized by the inability of the tubule to excrete enough $NH_4$ as a direct consequence of increased cellular stores of K.

(ii) Heart Disease

In another embodiment, the methods and compositions of the invention can be used to augment heart function in a subject with a heart disease or disorder. Heart failure is one of the leading causes of morbidity and mortality in the United States. Heart failure can result from any condition that reduces the ability of the heart to pump blood. Most frequently, heart failure is caused by decreased contractility of the myocardium, resulting from reduced coronary blood flow. Many other factors may result in heart failure, including damage to the heart valves, vitamin deficiency, and primary cardiac muscle disease. (Guyton (1982) Human Physiology and Mechanisms of Disease, Third Edition, W. B. Saunders Co., Philadelphia, Pa., p. 205). Heart failure is commonly manifested in association with myocardial infarction. (Manual of Medical Therapeutics (1989) Twenty-Sixth Edition, Little, Brown & Co., Boston (W. C. Dunagan and M. L. Ridner, eds.), pp. 106-09).

Heart failure in humans begins with reduced myocardial contractility, which leads to reduced cardiac output. The methods and composition of the invention may be used to augment heart function. For example by creating an neomorphic organ augmentive structure an area of the heart that has been damaged or infarcted or ischaemia.

Heart diseases include, but are not limited to angina pectoris, myocardial infarction, and chronic ischemic heart disease.

(iii) Urogenital disorders

In another embodiment, the methods and compositions of the invention can be used to augment urogenital organ function in a subject with a urogenital organ disease or a disorder. Examples of urogenital disorders include, but are not limited to those associated with the bladder, urethra, and ureter.

(iv) Spleen Disorders

The spleen is a small organ located next to the stomach that is part of the lymphatic system, the spleen helps protect the body against infection and filters blood. Patients who have had their spleen removed are more susceptible to certain types of infection. Accordingly, the methods and compositions of the invention can be used to ameliorate or control spleen disorders, for example by using cells recombinantly modified to express agents that control the disease or disorder. Example of spleen disorders include, but are not limited to, idiopathic purpura, Felty's syndrome, Hodgkin's disease, and immune-mediated destruction of the spleen.

Other embodiments and uses of the invention will be apparent to those skilled in the art from consideration of the specification and practice of the invention disclosed herein. All U.S. patents and other references noted herein for whatever reason are specifically incorporated by reference.

EXAMPLES

Example 1

VEGF Secretion from Encapsulated CHO VEGF Cells

I. Material and Methods
Matrix:

A biological acellular collagen matrix was isolated from Swine kidneys. Swine kidneys were harvested, agitated in triton 100X (Sigma St. Louis, Mo.) and ammonium hydroxide (Sigma). The matrices were washed extensively with saline, and allowed to dry. The matrices were lyophilized and cut into 3×3 mm sections. Scanning electron microscopy confirmed the acellular nature of the collagen matrices.

Renal Cells:

Kidneys from 5 day old C57 black mice (Jackson labs; Bar Harbore, Me.) were harvested, minced, suspended in Keratinocyte SFM medium (Gibco BRL; New York, N.Y.) containing Collagenase/Dispase 1 mg/ml (Boehringer Mannheim; Mannheim, Germany) and agitated for one hour at 37° C. The mixed culture of renal cells was filtered serially through 104 μm sieves until all undigested tissue was removed. The filtrate was washed twice with medium and seeded on the collagen matrices at a density of $30 \times 10^6$ cells/ml.

Isolation and Culturing of Cardiac Cells:

This example describes one method of culturing cardiac cells, which can be used with the present invention. Cardiac cells, e.g., from atrial tissue can be obtained from mammals. Atrial tissue can be obtained for example, from the right atrial appendages harvested from cardiovascular surgery patients undergoing procedures requiring heart-lung bypasses. The appendages can be removed and placed in ice-saline slush for rinsing. The tough epicardial covering can be removed using a scalpel to reduce the amount of connective tissue included in the cell harvest. The remaining atrial muscle can be minced into small (0.5-1.0 mm³) pieces and placed in cold Hank's Balanced Salt Solution (HBSS) without calcium or magnesium (Whittaker, Walkerville, Mass.). The minced atrial tissue can be digested in 0.14% collagenase solution (Worthington, Freehold, N.J.) at a concentration of 1.43 mg/ml. The pieces can be placed in 35 ml of this solution and digested in a shaker at 37° C. at 125 RPM for one hour. The supernatant can be removed from the atrial tissue and centrifuged at 3500 RPM for 10 minutes at 37° C. Another 35 ml of collagenase solution can be placed with the minced tissue while the supernatant was spinning and the digestion continued for another hour. The supernatant collagenase solution can be removed and set aside for use in the third digestion. The cell pellet can be resuspended in 2 ml of Eagle's Minimal Essential Medium (EMEM) with Earle's Salts (Whittaker) containing 30% newborn calf serum (Whittaker) and 0.1% antibiotic solution-10, 000 units/cc Penicillin G, 10,000 μg/cc Streptomycin and 25 μg/cc Amphotericin B (Gibco, Grand Island, N.Y.). This process can be continued for a further digestions.

The various digestions can be pooled, and the cell concentration can be checked using a hemacytometer and adjusted to $1 \times 10^5$ cells/ml with EMEM. The cells can be plated on 35 mm gelatin coated dishes (Corning, Corning, N.Y.) and incubated at 37° C. in 5% $CO_2$ atmosphere. Medium can be changed every three days for the first two weeks of growth, then every five to seven days thereafter. When the cultures spread out and approach confluence, they can be treated with trypsin and transferred to 60 mm gelatin coated dishes (Corning) in EMEM. When the cells approach confluence, they can be treated with trypsin and transferred to T-75 flasks (Corning) in MCDB 107(Sigma, Saint Louis, Mo.).

A portion of the cells grown in MCDB 107 can be plated on four chamber gelatin coated slide culture plates (Lab Tek, Naperville, Ill.). Control cells can be human umbilical endothelial cell and human skin fibroblast cultures (Beaumont Research Institute, Royal Oak, Mich.) that can be grown in M199 with 20% fetal bovine serum, 1% L-glutamine, 0.1% of 5 mg/ml insulin-5 mg/ml transferrin-5 µg/ml selenious acid (Collaborative Research Inc.), 0.6 ml heparin (0.015% in M199), 0.1% antibiotic-antimycotic solution (Gibco Laboratories: 10,000 units/ml sodium pennicilin G, 100,000 mcg/ml streptomycin sulfate and 25 mcg/ml amphotericin B), and 300 µg/ml of Endothelial Cell Growth Supplement (ECGS) from Biotechnology Research Inst., Rockville, Md. When control cultures and harvested cells spread out and approached confluence they can be rinsed with HBSS and fixed with 10% formalin for 10 minutes. The chambers can be removed and the cells remaining on the plates can be stained with immunoperoxidase stains for smooth muscle alpha-actin (Lipshaw, Detroit, Mich.), striated muscle specific myosin (Sigma, St. Louis, Mo.), myoglobin (Dako, Carpinteria, Calif.), factor VIII (Lipshaw, Detroit, Mich.), and atrial natriuretic factor peptide (Research and Diagnostic Antibodies, Berkeley, Calif.) The plates can then be examined using light microscopy.

A portion of cells growing in MCDB 107 can be plated on 96-well gelatin-coated plates (Corning). When they spread out and approach confluence they can be rinsed with HBSS and fixed with 2.5% glutaraldehyde, 0.2 M cacodyiate buffer, pH 7.4 (Polysciences, Inc., Warrington, Pa.), post-fixed with 1% osmium tetroxide (Polysciences, Inc.), embedded in Epon LX-112 resin (Ladd's Research, Burlington, Va.), stained with 0.03% lead citrate (Eastman Kodak, Rochester, N.Y.) and saturated uranyl acetate (Pelco Co., Tustin, Calif.) in 50% ethyl alcohol and then examined under transmission electron microscopy.

Fluorescent Labeling:

Renal cells used for the in vivo studies were tagged with DiI fluorescent dye (D-282, Molecular Probe; OR, US). Stock solution of 1 mg/ml was prepared in dimethylsulfoxide (DMSO), diluted 1:1000 and filtered. The cells were incubated in the solution for 20 minutes at 37° C., and washed 3 times with medium.

Engineering of CHO Cells to Constitutively Express VEGF:

CHO cells were chosen for the expression of recombinant VEGF. We have previously cloned the human cDNA encoding VEGF$_{165}$, (Soker et al. *Biol Chem* (1996) 271: 5761) and subcloned it into pRc/CMV expression vector (Invitrogen). In the resulting pCMV-VEGF plasmid, the expression of VEGF is driven by the cytomegalovirus promoter. VEGF expression vector was used to transfect CHO cells using Lipofectamine (Life Technologies; Rockville, Md.) and neomycin resistant clones were selected. Conditioned media was collected from individual clones and proteins were absorbed on heparheparin Sepharose. VEGF western blot was performed as described below. CHO clones which were shown to express high levels of VEGF (CHO/VEGF) were selected for subsequent experiments. CHO/VEGF clones were cultured in MEM a supplemented with 5% FBS (GibcoBRL) and 50 mg/ml G-418 (GibcoBRL) in order to ensure maintenance of the transfected VEGF cDNA.

CHO/VEGF Cell Microencapsulation:

CHO/VEGF cells were encapsulated within microspheres composed of Ca-alginate, and were coated with the positively-charged polyelectrolyte PLL, and recoated with alginate. Pellets of CHO/VEGF cells were resuspended in sodium alginate-in-saline (1.5% w/v, Ultrapure MVG; Pronova, Portsmouth, N.H.), to a final ratio of $0.5 \times 10^6$ cells/ml of alginate. The suspension was sprayed through a 22G needle located inside an air jet-head droplet-forming apparatus, into a solution of (N-[2-Hydroxyethyl]piperazine-N-[2-ethanesulfonic acid])-buffered calcium chloride (13 mM HEPES, 1.5% (w/v) $CaCl_2$, pH 7.4, Sigma), where they gelled for 20 min. The CHO/VEGF cell-Ca-alginate beads were washed 3 times with HEPES to remove free calcium ions. The alginate microspheres were coated with 0.06% (w/v) PLL of 21 kDa molecular weight (MW; Sigma) in saline for 15 minutes with gentle agitation. Unreacted PLL was removed by washing the microspheres 3 times with 13 mM HEPES-buffered saline and the microcapsules were additionally coated with 0.125% sodium alginate for 10 minutes.

In Vitro Release of VEGF from Microencapsulated CHO/VEGF Cells:

The microencapsulated CHO/VEGF cells were suspended in Alpha Medium with FBS (GibcoBRL), at a density of $0.06 \times 10^6$ encapsulated cells/well. Microcapsules were incubated at 37° C. with 50% $CO_2$. The medium was changed every week for six weeks and assayed for VEGF using western blot analyses. Unencapsulated cells were used as controls. For western blot analyses, the medium was incubated with heparin Sepharose for 24 hr at 4° C. The Sepharose was washed with buffer (150 mM NaCl, 0.1% Triton X-100 and 20 mM Tris) followed by PBS and subjected to SDS-Poly acrylamide gel electrophoresis. Proteins were electrophoretically blotted onto Imobilion P membranes (Millipore Corp). Blots were probed with human anti VEGF antibodies (Santa Cruz; Santa Cruz Calif.). Detection of antibodies was performed by chemiluminescence using an ECL system (Amersham Corp)

In Vivo Studies of VEGF from Microencapsulated CHO/VEGF Cells:

A total of 90 matrices were implanted in 8 week old athymic nude mice (Jackson lab; Bar Harbor, Mass.). Five mice were used for each group and time point. Two implants with or without renal cells were implanted subcutaneously in each animal. Twenty four hours after implantation, alginate-PLL microspheres containing CHO/VEGF cells were injected to the area of the implanted renal cell seeded matrices. Two control groups were studied: 1. Acellular matrices followed by the injection of empty alginate-PLL microspheres (without CHO/VEGF cells); and 2. Cell-matrices scaffolds followed by the administration of empty alginate-PLL microspheres. Matrix scaffolds, skin and alginate-PLL microspheres from the study and control groups were harvested at 3, 7 and 14 days after implantation. Neovascularization was identified histologically and immunohystochemically Histological and Immunocytochemical Analyses:

Matrices with or without renal cells, alginate-PLL microcapsules with or without engineered CHO/VEGF cells, and skin harvested from experimental groups were immersed in Ornitin Carbamoyl Transferase (OCT) and frozen in liquid nitrogen. Cryostat sections (10 µm) were analyzed histologically with Hematoxylin and Eosin, and immunohistochemically using three different antibodies.

Poly-clonal anti-human VEGF, antibodies (Santa Cruz; Santa Cruz, Calif.) which do not cross react with mouse VEGF, were used to detect human VEGF secreted by the encapsulated CHO/VEGF cells. Bound primary antibody was detected using the avidin-biotin-immunoperoxidase method. The presence and distribution of blood capillaries was confirmed by endothelial cell staining with anti antibody CD-31 (pharminogen; Rockville, Mass.), also known as platelet endothelial cell adhesion molecule (pECAM-1). To identify the renal cells seeded on the matrices, osteopontin (OPN) immunostaining was performed using rabbit anti-mouse polyclonal antibody (a gift from Dr. Samy Ashcar; Childrens Hospital and Harvard Medical School). Bound primary antibody was detected using the avidin-biotin-immunoperoxidase method.

In Vitro Release of VEGF:

Based on the M.W. of VEGF (23 kDa), PLL of 21 kDa and 1.5% sodium alginate with high gluronic content (≤65%) were chosen. PLL with a M.W. between 1-22 kDa created a semipermeable membrane with a M.W. cut off of 70 kDa, i.e., preventing the diffusion of cells and antibodies. The microcapsules containing the CHO/VEGF cells had a spherical shape with an average diameter of 0.6 mm+/−0.05 mm.

For the generation of cells that would constitutively express high levels of VEGF, CHO cells were used. These have been previously used for expression of various recombinant proteins, including VEGF. CHO cells were transfected with the pCMV-VEGF expression vector and clonal populations of stably transfected CHO cells were obtained. Among these, clones that secreted high levels of VEGF (CHO/VEGF) as measured by western blot analysis, were selected.

Western blot analyses for human VEGF proteins (23 kDa), performed on the cultured medium of the encapsulated cells, depicted high levels of VEGF at all retrieval time points. The medium was changed at week 1, 2, 3, and 4. Two plates of encapsulated cells were used for each time point.

In Vivo Studies of Renal Cell Expansion with VEGF:

Two matrices were implanted in each animal. The renal cells had been pre-tagged with the fluorescent dye Dil-C18. The carbo-fluorescent dye enabled the differentiation between the implanted renal cells and the host cells which would invade the matrix. In addition, the renal cells could be tracked within the implanted matrix itself. Bright fluorescent labeling was seen on the surface of the matrices seeded with renal cells at days 3, 7 and 14 post implantation. On day 14, the fluorescent labeled renal cells were detected at different internal sites within the matrix, demonstrating the migratory trajectory of the cells into the three dimensional structures.

Osteopontin (OPN) is secreted by proximal and distal tubular renal cells and the cells of the ascending loop of Henle. In order to further confirm the renal origin of the cells implanted on the matrix, immUllohistochemical studies were performed with the OPN antibody. At days 3 and 7 the majority of the OPN stained renal cells were seen on the outer surface of the matrix, while at day 14, positive staining was noted throughout the matrix. Empty matrices, not seeded with renal cells, stained negatively for OPN.

Renal cell expansion and migration within the matrix was more extensive in the experimental group which was exposed to the VEGF secreting encapsulated cells than the microspheres alone, as evidenced by histological, immunohistochemical, and fluorescent labeling analyses.

II. Analysis of VEGF Secretion from Encapsulated CHO VEGF Cells

Microencapsulated CHO/VEGF cells and the surrounding tissues were harvested from each animal and processed with OCT. Immunostaining with anti human VEGF showed high levels of VEGF at the inner core of the microcapsules at days 3, 7 and 14 post implantation. Tissues surrounding the microcapsules also stained positively for VEGF. Empty microspheres without CHO/VEGF cells stained negatively for VEGF.

Analyses of Vascularization:

Macroscopic examination of the CHO/VEGF microencapsulated cell implant sites showed a progressive increase in vascularization toward the areas adjacent to the matrices. At days 7 and 14, extensive vascularization was evident from the skin and surrounding regions to the implanted matrix. Control groups which received the empty microcapsules showed only minimal vascularization.

Microscopic examination using immunostaining with CD-31 showed positive staining for endothelial cells in the skin harvested from the study groups at all time points. Immunohistological staining for CD-31 were done in nude mice skin harvested at day 3, day 7, and day 14 and in renal-matrix grafts harvested at day 7. An increase in clusters and sinusoidal structures of newly formed capillaries was seen in the skin over time. A comparison between H&E staining and CD-31 staining of the skin showed that the newly formed capillaries were scattered around existing blood vessels. Histological sections of nude mice skin were harvested at day 7 and day 14 post implantation. Positively stained sinusoidal structures were less numerous in tissues harvested from animals implanted with matrix-seeded cells but with no CHO/VEGF encapsulated cells when compared to the study groups.

At day 3, scattered endothelial cells were detected in the harvested matrices from the study groups. Endothelial cells clusters which did not show defined capillaries or blood vessels were detected in matrices harvested at days 7 and 14. Positive staining was also seen in the tissues surrounding the microencapsulated CHO/VEGF cells, but not in the microcapsules themselves, confirming the high angiogenic ability of the released VEGF in stimulating endothelial cell migration and proliferation.

Example 2

Genetically Engineering Muscle Cells to Transiently Produce VEGF

This study demonstrates that in vivo engineered muscle tissues improve their vascularity when VEGF gene modified muscle cells are used. Desmin positive myoblasts were obtained that formed spontaneously contractile myofibers by 2 weeks in vitro. VEGF and GFP expression in vitro was respectively assessed by Western blot analysis and fluorescence, showing that the myoblasts were successfully transfected. Analysis of the in vivo recovered engineered tissues with RT-PCR and fluorescence showed expression of VEGF and GFP proteins. Immunohistochemical analysis of the recovered tissues confirmed the muscle phenotype. Neovascularization and muscle tissue mass significantly increased with the functional VEGF-transfected cells compared with the non-functional VEGF-transfected cells.

Myoblasts Isolation:

All procedures were done in according with Children's Hospital Animal Care Committee protocols. Myoblasts were derived from single muscle fibers as previously described by Rosenblatt et al (*In Vitro Cell Dev Biol Anim.* (1995) 31(10): 773-779). Under general anesthesia (Ketamine/Xylazine: Ketamine 75 mg/kg and Xylazine 10 mg/Kg IP) the flexor digitorum brevis (FDB), from Lewis rats, was removed by microdissection. The muscle was washed in Dulbecco's modified Eagles medium (DMEM, Gibco Life Technology) and incubated for 2 hours at 37° C. in 35 mm dishes containing filter-sterilized 0.2% (wt/vol) type I collagenase (Worthington Biochemical) in DMEM. The muscle tissues were transferred to plates with medium consisting of 10% horse serum (HS, Gibco Life Technology), 1% Penicillin/Streptomycin (Gibco Life Technology) and 0.5% chick embryo extract (CEE ultrafiltrate, GIBCO) in DMEM. Under a transilluminating microscope, single muscle fibers were isolated by repeated pipetting. The separated muscle fibers were plated in Matrigel (1 mg/ml, MATRIGEL® Basement Membrane Matrix, Becton Dickinson) precoated Petri dishes and incubated at 37° C. and 5% $CO_2$. Myoblasts migrating from the plated myofibers were trypsinized and plated in 35 mm plates precoated with Matrigel (0.1 mg/ml). The myoblasts were cultured in proliferation medium [DMEM containing 20% fetal bovine serum (FBS), 10% HS, 1% Penicillin/Streptomycin (Gibco Life Technology) and 1% CEE]. The myogenicity of the single fiber-derived cells was further confirmed by inducing differentiation with a low-serum medium (DMEM, 2% HS, 1% CEE and 1% Pen/Strept).

Immunohistochemical Analysis:

To confirm the purity of the cultured myoblasts, hematoxilin & eosin staining, and immunohistochemical analyses were performed using muscle-specific antibodies: sarcomeric tropomyosin (Santa Cruz Biotechnology, Inc), desmin (Santa Cruz Biotechnology, Inc) (Rando et al. *J Cell Biol.* (1994) 125(6):1275-1287). Cells were seeded into 8 well chamber slides (Lab-Tek®), incubated to sub-confluence and fixed in 2% formaldehyde for 5 minutes, in 4% formaldehyde for 5 minutes, and in ice-cold methanol. Cell layers were washed 3 times with PBS. After blocking with 5% horse serum, the slides were incubated in a 1:5 dilution of anti-desmin goat antibody and anti-sarcomeric mouse tropomyosin (Santa Cruz 1:100 dilution) at 4° C. overnight, followed by 30 min incubation in a 1:200 dilution of secondary antibody [byotinilated anti-goat and anti-mouse respectively (Vector BA-9500)]. The cells were incubated with fluorescein-avidin D (Vector A-2001), diluted 1:500 in 10 mM HEPES, 0.15 M NaCl, pH8.2, for 10 min at room temperature. Nuclei were counterstained with 4,6 diamino-2-phenylindole dye. Images were recorded using the IX-70 microscope with a Magna Fire Digital Imaging Camera System (Olympus).

Construction of GFP-VEGF Plasmid and Transfection:

Full-length cDNA for human $VEGF_{165}$ was directionally cloned into the MCS site of a pIRES2-EGFP plasmid (Clonotech). Skeletal myoblasts at 50-60% confluence were transfected with the bi-cystronic plasmid, encoding VEGF and green fluorescent protein (GFP) using LipofectAMINE PLUS™ (Gibco Life Technology). Control cells were transfeted with a plasmid encoding a non-functional VEGF-alkaline phosphatase (AP) fusion protein. Briefly, 4 µg of DNA were diluted into 25 µl of Optimem (Gibco) and 8 µl of PLUS Reagent were added. The solution was mixed and incubated at room temperature (RT) for 15 min. Another 25 µl of Optimem and 5 µl of LipofectAMINE Reagent was then added to the first solution, mixed and incubated for 15 min at RT. The final solution was diluted in 800 µl of Optimem and added to each well containing the myoblasts. After 6-7 h of incubation at 37° C. at 5% $CO_2$, 1 ml of medium with FBS was added.

In Vitro VEGF Expression:

Two days after transfection, the culture media were collected from VEGF-transfected, control-transfected and non-transfected myoblasts. Two ml of culture medium were centrifuged at 2000×rpm for 5 min to remove the cell debris and incubated with 30 ul of heparin agarose beads for 1 hour at 40° C. The Heparin agarose beads were washed 3 times with PBS and resuspended in 30 ul of Laemmli sample buffer (Li et al. *J. Cell Sci* (2000) 113(pt 9): 1525-34). and boiled 5 min at 95° C. Proteins were resolved on a 12% SDS-PAGE and transferred to PVDF membrane (Millipore) at 100 mA for 80 min. Filters were exposed to blocking solution containing 3% bovine serum albumin in Tris-Buffered Saline (TBS, pH7.4) for 1 hour at RT. Specific polyclonal antibody directed against VEGF (Santa Cruz, # sc-507) was used at 1:1000 for 4 hours at 4° C., followed by 3 washes with 0.1% Tween 20 in TBS. The filters were incubated with the secondary antibody coupled to horseradish peroxidase (Sigma, #A0545) at 1:8000 for 30 min at RT, followed by washes as previously described. Immuno-reactive bands were visualized using Western Lighting™ Chemiluminescence Reagent plus (Perkin-Elmer Life Sciences) and detected on Hyperfilm™ MP (Amersham Pharmacia biotech).

In Vitro GFP Expression:

Transfected cells were examined with a microscope equipped with phase-contrast and epifluorescence optics, using 20×, 40× and 400× Plan Neofluran objectives. Images were collected with a cooled camera and assembled with Maginfare and Adobe Photoshop software. Cytofluorimetric analysis was done on a FACScan instrument (Becton Dickinson, San Jose, Calif.) in-line with a Power Macintosh computer using the CELLQuest software. A minimum of 10,000 cells was analyzed in each experiment with a 488-nm excitation wavelength and 520-nm emission wavelength. Briefly, 48 hours after the transfection was started, the cells were trypsinized, washed twice with 2 ml of PBS, spun down at 1100 RPM for 7 minutes and resuspended in 0.5 ml PBS for analyses.

Cell Injections In Vivo:

GFP-expressing myoblasts were isolated using a FACScan instrument (Becton Dickinson, San Jose, Calif.) with a 488-nm excitation wavelength and a 520-nm emission wavelength. The isolated cells were cultured in proliferating medium for 2 days after transfection. For the injections, the cells were suspended in collagen type I (from rat tail, Collagen type 1, Becton and Dickinson) diluted in 10×MEM (Gibco) and $Na_2HCO_3$ at a concentration of $10 \times 10^6$ cells/ml and a 350 µl suspension was injected subcutaneously in nude mice. Five mice were used for each time point for a total of 40 animals. Each mouse had 2 injection sites.

In Vivo Studies:

Cells were suspended in collagen type I (Rat Tail, Collagen type 1, Becton and Dickinson) diluted in 10×MEM (Gibco) and $Na_2HCO_3$. Transfected myoblasts suspended in collagen (250 µl) were injected subcutaneously in nude mice at a concentration of $10 \times 10^7$ cells/ml. Five different mice were used at each time point for each experimental group, for a total of 40 animals. Each mouse had 2 injection sites.

Retrieval and Analyses of Engineered Tissue:

The newly formed tissues were surgically recovered from the injection sites at one, three, four and eight weeks after implantation. Recovered tissues underwent GFP fluorescence, immunohistochemical, PCR, and volumetric analysis at all time points. The sizes of the implants was measured with digital caliper (Mitutoyo) and volumes were calculated as $V = \frac{1}{6} \times Height \times Width \times Depth$.

The retrieved tissues were fixed overnight in 10% buffered Formalin (Fisher Scientific) and include in paraffin. Parts of the tissues were frozen in liquid nitrogen for molecular studies. Paraffined sections were cut at 5 µm (Laica RM 2145). Hematoxilin & Eosin staining, and Immunohistochemical analyses were performed using muscle-specific antibodies: Sarcomeric Tropomyosin (Santa Cruz Biotechnology, Inc) and Desmin (Santa Cruz Biotechnology, Inc). Analysis of neuvascularization was performed by analysis of positive FVIII (Sigma-Aldrich, St. Louis, Mo.) cells in the retrieved tissue (Folkman, J. *Endocrinology* (1998) 139(2): 441-442).

In order to see GFP signal, frozen sections were cut at 10 µm and examined with a microscope equipped with phase-contrast and epifluorescence optics, using 20× Plan Neofluran objectives. Images were acquired using IX-70 microscope with Magna Fire Digital Imaging Camera System (Olympus) and processed using Adobe Photoshop 5.0 and NIH Image for semi-quantitative analysis.

Micro-vessel density (MVD) was determined by counting the number of vWF-positive capillaries, using light microscopy. Eight high-power fields in each section were randomly selected and the number of capillaries was averaged and expressed as the number of capillary vessels per high-power field (0.2 mm$^2$).

RT-PCR:

RNA was isolated from cultured cells and cell pellets with RNAzol reagent (Tel-Test Inc., Friendswood, Tex.) according to the manufacturer's protocol. RNA (2 µg) was processed for c-DNA synthesis with Superscript II reverse transcriptase with random hexamers (Life Technologies, Rockville, Md.). c-DNA was used for each PCR reaction, at a final volume of 30 µl with 200 nM dNTP, 10 pM of each primer, 0.3U Taq-DNA-polymerase, reaction buffer, and MgCl2 (Life Technologies, Rockville, Md.), in a PTC-100 cycler (MJ-Research Inc., Watertown, Mass.). The cycling conditions consisted of 94° C. for 2 minutes, annealing at 63° C. for 40 seconds, and elongation at 72° C. for 1 minute. Cycle numbers varied between 22 and 37 cycles. All primers were obtained from Life Technology.

In Vitro Isolation and Transfection of Primary Myoblasts:

Myoblasts were successfully isolated from a culture of individual myofibers. Single muscle fibers were isolated from Lewis rats using collagenase digestion. Putative satellite cells, separated from the main fiber, appeared 12-24 hrs after plating. By 4-5 days, approximately 200-300 cells surrounded every single myofiber. The isolated myoblasts, if grown to confluence and differentiated in a low-serum medium, formed short myotubes that showed spontaneous contraction after 2 weeks. All the cells reacted positively to desmin and sarcomeric tropomyosin antibodies with immunostaining, indicating a homogeneous myoblast culture. Other protocols for isolating myoblasts are known in the art (See *Current Protocols in Human Genetics* Ed. Ann Boyle John Wiley & Sons, Inc. 2002).

The possibility of engineering muscle formation in vivo depends on the ability to maintain large volume of cells following implantation. In order to achieve this goal, vascularization of the regenerating tissue is essential. Myoblasts were transfected with a plasmid encoding VEGF$_{165}$ and GFProtein or with a plasmid encoding monomeric VEGF (VEGF$^{mono}$).

A system of transient and local VEGF administration to promote localized angiogenesis with minimal systemic side effects was developed. An expression vector encoding for human VEGF$_{165}$ and GFP via a bi-cystronic RNA was generated. In this system VEGF expression was coupled with the expression of GFP that could be detected in vitro and in vivo without disrupting the cells expressing these proteins. As control, we used a vector encoding for an inactive VEGF monomer (VEGF$^{mono}$). VEGF-GFP and VEGF$^{mono}$ plasmids were successfully used to transfect myoblasts. Two days after transfection, more than 30% of the cells expressed GFP, and the isolated cells appeared green under fluorescence microscopy (not shown). Transfected myoblasts were successfully differentiated into muscle fibers in vitro and maintained their contractile ability. GFP expression was observed in more than 50% of the newly formed fibers by fluorescence microscopy (not shown). This higher percentage is probably due to the fact that the new fibers were formed by fusion of a few cells and one GFP expressing cell within the fiber renders the entire fiber green. This result indicates that GFP expression did not interfere with myoblats function in vitro. The percentage of cells appearing green under fluorescent microscopy decreased with time, and at 4 weeks, no cells with fluorescent activity could be detected. Non-transfected cells did not display green fluorescence.

VEGF and GFP expression in vitro was assessed by Western blot analysis and fluorescence, respectively. Myoblasts were analyzed at light and fluorescent microscopy at low (I and II) and (III and IV) high confluence. The ability to form muscle fibers was not affected by VEGF-transfection [V and VI]. On day 2 after transfection more than 30% of the cells were expressing GFP as determined by FACS analysis. This result was confirmed by fluorescence microscopy: cells appeared green under fluorescence microscopy, however the percentage of cells expressing the protein decreased with time, and at 4 weeks, the cells lost their fluorescent activity. Not-transfected cells did not express any fluorescence. Western blot analysis of conditioned media was carried out two days after transfection, using anti-VEGF antibodies, showed a high expression of VEGF. Two immunoreactive bands with a molecular mass of approximately 25 kDa were detected, indicating secretion of VEGF from transfected myoblasts (not shown). RT-PCR analysis of transfected cells yielded a single 650$_{bp}$ DNA product, confirming recombinant VEGF$_{165}$ expression in the transfected myoblasts (not shown).

Transfected myoblasts successfully differentiated into muscle fibers in vitro and maintained their contractibility. GFP and VEGF expression in the new fibers was detected by fluorescence microscopy and Western blot analysis in vitro, respectively. More than 50% of the new fibers appeared to express GFP. This high percentage is probably due to the fact that the new fibers were formed by fusion of a few cells and if one of the cells within the fiber was expressing GFP the entire fiber will show green fluorescence.

Figure 2:
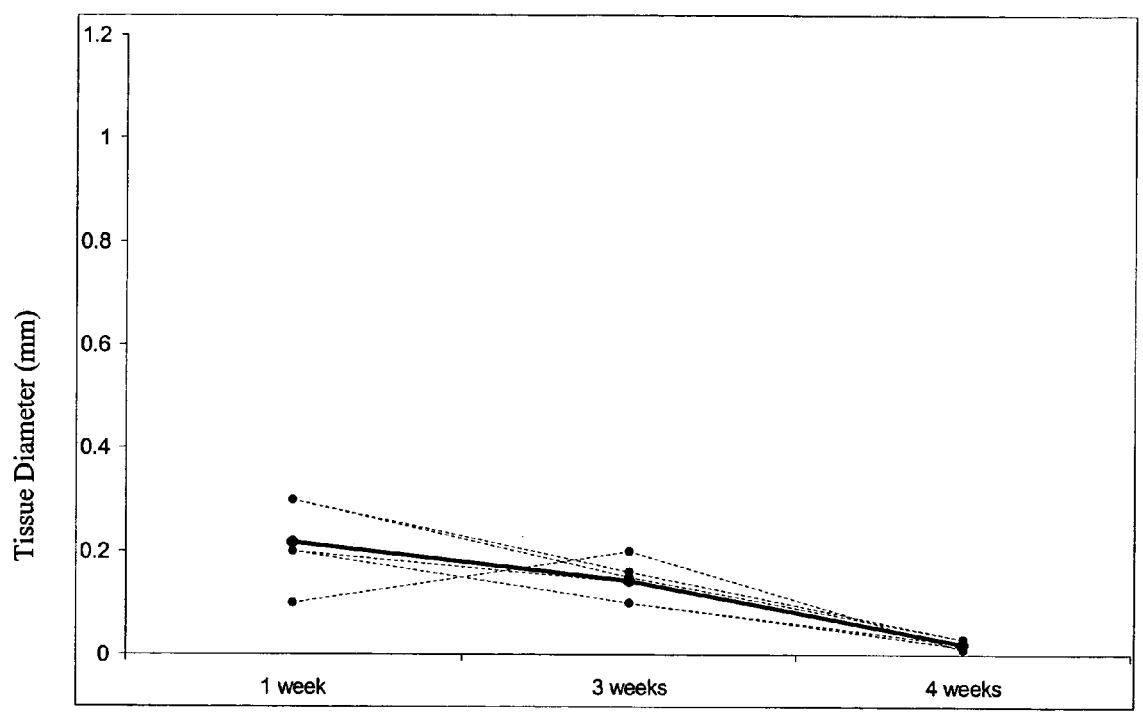
FIG. 2 is a graph of tissue diameter (mm) over time (weeks) of engineered muscle tissue retrieved at 1, 3 and 4 weeks after transplantation with myoblasts transfected with non-functional VEGF-cDNA.

In Vivo Muscle Engineering:

Transfected cells were suspended in collagene and injected subcutaneously in nude mice. The injected myoblasts were retrieved at 1, 3, 4 and 8 weeks after implantation and examined by fluorescence, PCR, volumetric and immunohistochemical analyses. Grossly, abundant neovascularization was evident around the VEGF-GFP-transfected cell injection sites. In contrast, injection of cells transfected with VEGF$^{mono}$ (a non-functional VEGF) resulted in a much smaller cell mass and only a limited neovascularization. The VEGF-transfected myoblasts maintained their initial volume for the duration of the study, whereas myoblasts transfected with the non functional VEGF lost their volume significantly from 300 mm$^3$ to an average of less than 30 mm$^3$ over 8 weeks. Muscle formation in the subcutaneous space of mice after injection with myoblasts transfected with functional VEGF-cDNA increased in diameter from approximately 0.2 mm to 0.8 mm as shown in FIG. 1. In contrast, the diameter of the muscle following injection with myoblasts transfected with non functional VEGF cDNA decreased over time (FIG. 2).

Microscopically neovascularization was evaluated by FVIII expression in the retrieved tissue and the VEGF-GFP transfected tissue showed a good endothelial grow with an efficiency capillary formation compared to the inactive VEGF transfected tissue which did not show any endothelial invasion of the neo-tissue. Fluorescence microscopy of the tissues retrieved from nude mice 1 week after implantation showed that cells were expressing GFP and VEGF. No expression of GFP was detectable at 3 and 4 weeks. These results were supported by RT-PCR analysis. GFP or VEGF expression was detectable in the tissue specimens retrieved at 3, 4 or 8 weeks. The retrieved tissues formed by the transfected myoblasts showed muscle formation and neovascularization. The ability to form muscle fibers in vivo was not affected by VEGF-transfection. Immunohistochemical analysis of the recovered tissues confirmed their muscle phenotype. Multinucleated desmin and sarcomeric tropomyosin positive cells were evident at all time points. Factor VIII immunostaining demonstrated the formation of capillary networks in the engineered muscle tissues.

Figure 3:
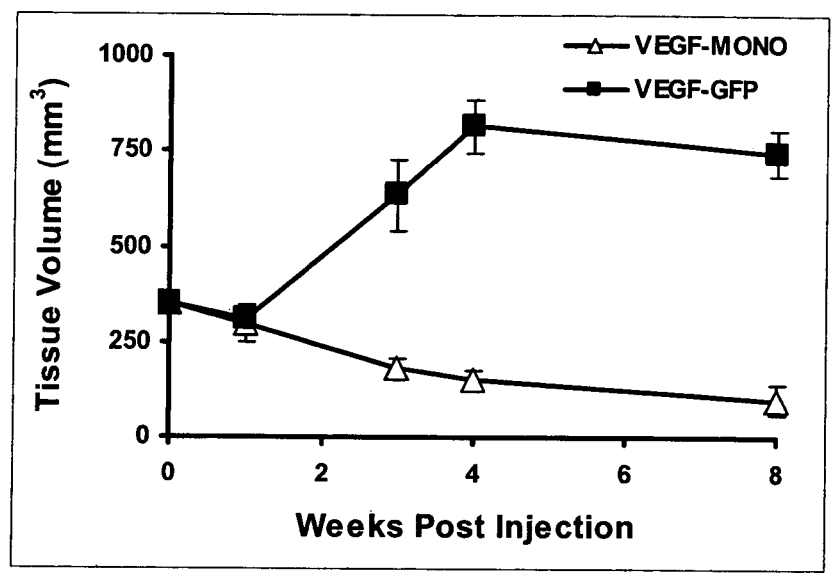
FIG. 3 is a graph of tissue volumes showing that tissues generated from $VEGF^{MONO}$ transfected myoblasts progressively lost their volume whereas tissues generated from VEGF-GFP transfected myoblasts maintained their volumes for the duration of the study.

To test the function of VEGF-expressing myoblasts in vivo, cells were suspended in collagen and injected subcutaneously into nude mice. The tissues were retrieved 1, 3, 4 and 8 weeks after injection and examined by fluorescence microscopy, RT-PCR and immunohistochemical analyses. Gross examination of the injection sites three weeks after injection showed the formation of bulkier tissue mass in the VEGF-GFP transfected myoblast group than the myoblasts transfected with VEGF$^{mono}$ plasmid at all time points (not shown), whereas the myoblasts transfected with the control plasmid showed only a scar under the skin. Volume measurements indicated a progressive volume in the tissues formed from VEGF-GFP transfected myoblasts up to 4 weeks after injection and their volumes were maintained for the duration of the study (FIG. 3). In contrast, tissues from myoblasts transfected with VEGF mono lost their volume progressively from about 350 mm$^3$ to less than 100 mm$^3$ over 8 weeks.

Immunohistochemical analysis of the recovered tissues using desmin and sarcomeric tropomyosin confirmed the muscle phenotype. Immunohistochemical analysis was performed on tissues formed from the VEGF-GFP transfected myoblasts. Multinucleated desmin positive cells were evident throughout the tissue (not shown). Similar results were obtained with anti-sarcomeric tropomyosin antibodies, indicating that VEGF-GFP expressing myoblasts formed muscle tissue in vivo.

Fluorescent microscopy of tissues retrieved after 1 week showed a number of GFP expressing clusters. However, after 3 weeks no GFP expression was detected. Similarly, VEGF expression in the tissue, as determined by RT-PCR, revealed expression after 1 week but no signal for VEGF could be detected after 3 weeks. This result indicates that VEGF and GFP are only transiently expressed by the myoblasts in vivo.

Tissue vascularization was evaluated by anti-von Willebrand factor (vWF) staining. The VEGF-GFP expressing tissues showed extensive capillary network formation (not shown), compared to the VEGF$^{mono}$ expressing myoblasts that showed no neovascularization. Microvessel density (MVD) was determined by counting the number of capillaries in several high-power fields. Tissues derived from the VEGF-GFP transfected myoblasts had approximately a 3 fold higher MVD than tissues from the VEGF$^{mono}$ transfected myoblasts (FIG. 4), indicating VEGF bioactivity in vivo. For this analysis, rat myoblasts, derived from cultures of a single muscle fiber, were transfected with a plasmid encoding VEGF and GFP or a control plasmid. Control-transfected cells and cells expressing VEGF-GFP, that were selected by FACS, were injected mixed with gelatin into the subcutaneous space of immune-deficient mice ($2.5 \times 10^7$ cells/mouse). Newly formed tissues from control-transfected myoblasts and VEGF-transfected myoblasts were surgically retrieved from the injection sites at one, two and three weeks after implantation and tissue volumes were determined. The recovered tissues from the VEGF-transfected myoblasts were fixed and embedded in paraffin. Tissue sections were immuno-stained with anti-von Willebrand factor (VWF) antibodies and photographed at 40 and 400-fold magnifications (not shown). Active neovascularization was observed near the VEGF-expressing muscle tissue, resulting in the formation of a developed vascular network inside the newly formed tissue.

Taken together our studies demonstrate the feasibility of VEGF gene transfer into primary cultures of muscle cells, which are subsequently used for the creation of well vascularized muscle tissue in vivo. This approach permits timed expression of VEGF in the newly formed muscle, leading to well vascularized tissue. These results demonstrate one aspect of the present invention which uses transient expression of VEGF, as shown here, using encapsulated cells for angiogenesis stimulation.

This Example demonstrated a transient and local system for the delivery of angiogenic modulating agents in order to improve the vascularization of engineered muscle tissue in vivo. Recent advances in our understanding of the angiogenic process and the isolation of potent and specific angiogenic factors have encouraged the use of specific strategies for therapeutic angiogenesis. VEGF is a major regulator of angiogenesis and a specific endothelial cell growth factor. Since temporal release of VEGF was desired, a system for transient expression of VEGF through naked plasmid DNA transfection was designed. The addition of a GFP marker that co-expressed with VEGF was used to visually determine the duration of VEGF expression. The most crucial time for the survival of the injected donor myoblasts is within the first 7 days and these results show that the transfected myoblasts expressed VEGF for 1 week in vivo. The angiogenic process in the bioengineered tissues should follow the kinetics of normal vascular development and VEGF may be required for the initial differentiation, proliferation and formation of endothelial tubes.

This Example showed that isolated myoblasts can proliferate well in vitro and were easy to expand in culture. In order to promote vascularization in vivo, the myoblasts were engineered to transiently express VEGF, by using plasmid DNA transfection. Approximately 30% of the myoblasts expressed the transfected genes, which did not interfere with their ability to differentiate and form functional multinucleated muscle fibers in vitro. These results suggest that recombinant protein expression does not induce physiological changes in the cultured myoblasts and does not interfere with their capability to form functional muscle. In the current study we have shown that myoblasts transfected with VEGF cDNA formed muscle tissue in vivo that maintained its volume for at least 8 weeks. When a non-functional form of VEGF was used instead, the regenerated muscle tissue progressively lost its volume. The volume loss was associated with a significant decrease in microvessel density, which emphasizes the important role of neovascularization in muscle tissue formation. The expression of VEGF and the marker GFP was detected after 1 week but not after 3 weeks. This result suggests that VEGF may be needed initially when the cells are forming tissue, but when the vascularized muscle tissue is already formed the angiogenic factors may be found endogenously. VEGF levels and the duration of VEGF expression may be further controlled by greater transfection efficiencies using viral vectors, including replication-deficient adenoviruses. Taken together, these results indicate that VEGF not only increases the survival of injected myoblasts, but it was also necessary for the formation of larger tissue masses.

In conclusion, the present study demonstrates the feasibility of genetically modifying primary cultures of muscle cells to express VEGF in order to improve the vascularity of engineered muscle tissue in vivo. Our results indicate that VEGF contributes to muscle mass formation, probably by inducing tissue neovascularization. This approach has important clinical implications, such as the improvement of a vascular supply to ischemic tissues, including cardiac and skeletal muscles, and the generation of vascular networks in large solid engineered tissues. This approach has important implications in tissue engineering, such as the ability to transiently express VEGF in order to promote angiogenesis without deleterious effects of chronic expression, improvement of vascular supply to ischemic tissues, including cardiac and skeletal muscles and the generation of a vascular network in large solid engineered tissue organs and it could be employed for the repair and engineering of muscle structures in the genitourinary tract.

Example 3

Muscle Formation, Neovascularization, and Volume Preservation in Engineered Tissues Using a Combination of VEGF and Endothelial Cells This Example illustrates the methods of this invention by demonstrating tissue neovascularization following the implantation of myoblasts and vascular EC in bioengineered tissues. Dermal capillary-derived EC were used in this Example because they represent the same type of the EC in the mouse skin blood vessels that serve the source of EC for subcutaneous neovascularization. Incorporation of EC into the developing tissue had no major effect on tissue volumes of VEGF expressing and control myoblasts. This finding may be explained by the observation that the transplanted vascular EC were a small fraction of the vascular network of the newly formed tissues and the majority was the host (i.e., mouse) EC. However, incorporation of vascular EC enhanced and prolonged MyoD expression and thus, contributed to muscle differentiation of the engineered tissue. These results suggest that EC within a bioengineered tissue may function not only to support the newly formed vascular network but their interactions with cells of the developing tissue may have an important role in tissue differentiation. This hypothesis is supported by two recent studies that highlighted the importance of EC and blood vessels in embryonic development of two separate organs. Removal of the dorsal aorta in *Xenopus laevis* embryos impaired normal pancreatic islet development and resulted in lack of insulin expression (Lammert E, Cleaver O and Melton D: Induction of pancreatic differentiation by signals from blood vessels. *Science*. 294: 564-7., 2001). On the other hand, overexpression of VEGF in the pancreas during embryonic development led to ectopic insulin production and hyperplasia of pancreatic islet tissue. In the other study, liver buds were removed from mice deficient of the VRGF receptor Flk-1 (VEGFR-2), that fail to form blood vessels, and cultured in vitro (Matsumoto K, Yoshitomi H, Rossant J and Zaret K S: Liver organogenesis promoted by endothelial cells prior to vascular function. *Science*. 294: 559-63., 2001). Although the explanted liver tissue grew in size only a small fraction of the cells could function as hepatic cells. Thus, when engineering tissues with large volumes one must supply EC in order to support tissue vascularization and to provide appropriate developmental cues that are normally delivered from the endothelium during embryonic development of the original tissue.

This study revealed three important points. First, that generation of well-vascularized tissue is possible with myoblasts, transiently expressing VEGF. Secondly, infection of myoblasts with adenovirus encoding for VEGF allowed transient VEGF production that induced proper tissue vascularization. Because VEGF is a very potent stimulator of angiogenesis, as well as blood vessel permeability, uncontrolled growth of blood vessels stimulated by chronic secretion of VEGF could lead to a pathological process. Chronic expression of VEGF has been shown to produce hemangiomas as well as hemorrhages, enhancement of tumor angiogenesis and death in animal studies (Lee R J, Springer M L, Blanco-Bose W E, Shaw R, Ursell P C and Blau H M: VEGF gene delivery to myocardium: deleterious effects of unregulated expression. *Circulation*. 102: 898-901., 2000). Lastly, via induction of tissue neovascularization, VEGF also supported muscle tissue formation.

The present study has important implications in tissue engineering, such as the ability to transiently express VEGF in order to promote angiogenesis without deleterious effects of chronic expression, improvement of vascular supply to ischemic tissues, including cardiac and skeletal muscles and the generation of vascularly network in large solid engineered tissue organs. In conclusion this study demonstrates the feasibility of VEGF gene transfer into primary cultures of muscle cells, which are subsequently used for the creation of well-vascularized muscle tissue in vivo. This approach could be employed for the repair and engineering of muscle structures in the genitourinary tract such as kidneys, bladder, and external genitals. For example, the methods of shown in this example can be used, for example, with the methods described in Example 6 to improve the neovascularization of a kidney structure.

I. Materials and Methods

Myoblasts Isolation, Characterization and Cell Culture:

All procedures were done according to the Children's Hospital Animal Care Committee protocols. Myoblasts were derived from single muscle fibers as previously described by Rosenblatt et al (Rosenblatt J D, Lunt A I, Parry D J and Partridge T A: Culturing satellite cells from living single muscle fiber explants. *In Vitro Cell Dev Biol Anim*. 31: 773-9., 1995). Under general anesthesia (Ketamine/Xylazine: Ketamine 75 mg/kg and Xylazine 10 mg/Kg IP) the flexor digitorum brevis (FDB), from FVB mouse, was removed by microdissection. The muscle was washed in Dulbecco's modified Eagles medium (DMEM, Gibco Life Technology) and incubated for 2 hours at 37° C. in 35 mm dishes containing filter-sterilized 0.2% (wt/vol) type I collagenase (Worthington Biochemical) in DMEM. The muscle tissues were transferred to plates with medium consisting of 10% horse serum (HS, Gibco Life Technology), 1% Penicillin/Streptomycin (Gibco Life Technology) and 0.5% chick embryo extract (CEE) ultrafiltrate (Gibco) in DMEM. Under a transilluminating microscope, single muscle fibers were isolated by repeated pipetting. The separated muscle fibers were plated in Matrigel (1 mg/ml, MATRIGEL® Basement Membrane Matrix, Becton Dickinson) precoated Petri dishes and incubated at 37° C. and 5% $CO_2$. Myoblasts migrating from the plated myofibers were trypsinized and plated in 35 mm plates precoated with Matrigel (0.1 mg/ml). The myoblasts were cultured in proliferation medium {DMEM containing 20% fetal bovine serum (FBS), 10% HS, 1% Penicillin/Streptomycin (Gibco Life Technology) and 1% CEE}. The myogenicity of the single fiber-derived cells was further confirmed by inducing differentiation with a low-serum medium (DMEM, 2% HS, 1% CEE and 1% Pen/Strept).

Immunohistochemical Analysis of Cultured Myoblasts:

The isolated myoblasts were washed with PBS and stained with 0.5 □g/ml of 4',6'-Diamidino-2-Phenylindole (DAPI) in PBS for 15 min in order to stain the nuclei. Subsequently, they were washed with PBS and fixed with 4% Formaldehyde in PBS at room temperature for 5 min and incubated with cold methanol for 5 min. To confirm the purity of the cultured myoblasts, cells were incubated with 1.5% horse serum in PBS at room temperature for 45 min for blocking. The cells were incubated with anti-desmin antibody (Santa-cruz sc-7559, 1:100 dilution). Biotinylated anti-goat antibodies (Vector BA-9500) diluted 1:200 were used as the secondary antibody. The cells were incubated with fluorescein-avidin D (Vector A-2001), diluted 1:500 in 10 mM HEPES, 0.15 M NaCl, pH8.2, for 10 min at room temperature. Images were recorded using the IX-70 microscope with a Magna Fire Digital Imaging Camera System (Olympus).

Human Endothelial Cell Culture:

Human microvascular ECs immortalized with SV-40 T antigen (HMEC-1, a gift from Dr. Michael Detmar, Massachusetts General Hospital, Boston, Mass.) were grown in Dulbecco's Modified Eagle's Medium (Cellgro) with D-Glucose (4,500 mg/l, Sigma), 10% fetal bovine serum, hydrocortisone (1 ug/ml, Sigma) and 1% penicillin/streptomycin at 37 C in a humidified atmosphere with 5% $CO_2$.

Infection of Cells with Adenovirus Vectors:

The recombinant E1-deleted adenoviral vectors encoding for murine $VEGF_{165}$ under cytomegalovirus promoter (Ad-VEGF) and β-galacosidase (obtained from the Harvard Human Gene Therapy Initiative, Boston, Mass.). HMEC-1 cells were seeded at a density of $1 \times 10^6$ cells into 10 cm culture dish and 48 hours later infected with AdLacZ at MOI=30 for 1 hour, followed by adding 10 ml of growth medium. Myoblasts, at 70% confluent in 15 cm culture dish, were infected with AdVEGF at MOI=30 in a similar way. Infected cells were used for injections 48 hours after infection.

Western Blot Analyses of VEGF:

Myoblasts infected with AdVEGF were plated into 35 mm culture plate. Culture medium was retrieved for Western analysis of VEGF proteins at 3, 7 and 10 days and at 2, 4, 7 and 9 weeks after infection. Two ml of culture medium were centrifuged at 2000×rpm for 5 min to remove the cell debris and incubated with 30 ul of Heparin agarose beads for 1 hour at 4° C. The Heparin agarose beads were washed 3 times with PBS and resuspended in 30 ul of sample buffer and boiled 5 min at 95° C. Proteins were resolved on a 12.5% SDS-PAGE and transferred to PVDF membrane (Millipore) at 100 mA for 80 min. The membrane was incubated with Tris-Buffered Saline containing 0.1% Tween-20 (TBS/T) and 3% bovine serum albumin in for 1 hour. Anti-VEGF antibodies (Santa Cruz, #sc-507) were used at 1:1000 dilution for 4 hours at 4 C, followed by 3 washes with TBS/T. The filters were incubated with the secondary antibody coupled to horseradish peroxidase (Sigma, #A0545) at 1:8000 dilution for 30 min, followed by 3 washes. Immuno-reactive bands were visualized using Western Lighting™ Chemiluminescence Reagent plus (Perkin-Elmer Life Sciences) and detected on Hyperfilm™ MP (Amersham Pharmacia biotech).

Implantation of Myoblast and Endothelial Cells:

Infected myoblasts and HMEC-1 were suspended in collagen type I (Rat tail Collagen type 1, Becton and Dickinson), diluted in 10×MEM and $Na_2HCO_3$, were injected subcutaneously to nude mice (500 µl per injection site) at the concentration of $1 \times 10^7$ and $2 \times 10^6$ cells/ml of AdVEGF infected myoblast and AdLacZ infected HMEC-1, respectively. The study consisted of 4 groups (12 mice per group): AdVEGF infected myoblasts and AdLacZ infected HMEC-1(EC+VEGF), AdVEGF infected myoblasts (VEGF), AdLacZ infected HMEC-1 and non-infected myoblasts (EC) and non-infected myoblasts (Control).

Retrieval and Analyses of the Engineered Muscle Tissue

The newly formed tissues were surgically recovered from the injection sites at 1, 3, 5 and 8 weeks after implantation (3 mice for each time point). The sizes of the implants was measured with digital caliper (Mitutoyo) and volumes were calculated as V=π/6×Height×Width×Depth. Parts of the retrieved tissues were fixed overnight in 4% buffered formaldehyde and embedded in paraffin. Other parts were frozen in OCT medium for LacZ staining or were snapped frozen in liquid $N_2$ for western blot analysis.

Tissue Staining:

Paraffin-embedded tissues were sectioned at 5 µm (Laica RM2145) and stained with hematoxylin and eosin (H&E) and with anti-mouse CD31 antibodies (Pharmingen #01951D). Frozen section were cut at 10 µm and fixed with 2% formaldhyde, 0.2% glutaraldehyde, 0.02% NP-40 and 0.01% sodium deoxycolate in PBS pH7.8 for 30 min at RT and then wash 3 times with PBS. Samples were incubated in LacZ staining solution (2 mM $MgCl_2$, 0.02% NP-40, 0.01% sodium deoxycolate, 5 mM K-ferricyanide, 5 mM K-ferrocyanide and 0.1% X-gal in PBS pH 7.8) at 37 C for 8 to 16 hours in dark. Images were acquired using IX-70 microscope with Magna Fire Digital Imaging Camera System (Olympus) and processed using Adobe Photoshop 5.0 and NIH Image for semi-quantitative analysis.

Myosin and MyoD Western Blot:

Small pieces of frozen tissue were pulverized and resuspended in lysis buffer (2 mM Tris-HCl pH7.4, 150 mM NaCl, 1% Triton-X, Complete™ protease inhibitor cocktail tablets (Rosh, #1697498), mixed with concentrated sample buffer and boiled 5 min at 95° C. Proteins were resolved on a 9% and 6% SDS-PAGE for MyoD and Myosin, respectively and transferred to PVDF membrane (Millipore) at 100 mA for 80 min. Monoclonal anti-MyoD (BD Biosciences, #554130) and anti-Myosin (skeletal, Sigma, # M8421) antibodies were used for primary antibodies, and anti mouse IgG (Sigma, #A2554) was used for secondary antibody. Immuno-reactive bands were visualized using Western Lighting™ Chemiluminescence Reagent plus, as described for VEGF Western blot analysis. The x ray films were scanned and band densities were evaluated using NIH image software.

II. Combination of VEGF and Endothelial Cells Enhance Muscle Formation

As illustrated below, the engineered tissues formed muscle, as evidenced by H&E staining and immunohistochemical probing. Neovascularization was detected in the engineered muscle tissues of VEGF-infected cells. EC were shown to participate in blood vessel formation by X-gal staining. In contrast, engineered muscle of non-infected cells had a significantly smaller mass of cells, less neovascularization and only a few HMEC-1 cells could be detected. The VEGF-expressing tissues maintained their initial volume for 8 weeks, whereas the non-infected tissues lost their volume significantly. Sustained expression of muscle specific genes, myosin and MyoD, was evident only in muscle tissues containing VEGF-infected myoblasts.

Myoblast Isolation In Vitro:

Myoblasts were chosen for the engineering of muscle tissue because of their in vitro proliferation capability and their ability to form muscle tissue in vivo. Myoblasts were isolated from a culture of individual myofibers. Putative muscle satellite cells, separated from the main fiber, appeared 12-24 hrs after plating and after 4-5 days 200-300 cells surrounded every single myofiber. Subsequently, the isolated myoblast were subcultured expanded in vitro. When the cells were grown to confluence under low-serum conditions they fused and formed multinucleated myotubes, as shown by nuclear DAPI staining (not shown). The isolated myoblasts formed myofibers on Matrigel coated dishes and multi nucleated fibers were observed by nuclei staining using DAPI. The myotubes acquired spontaneous contraction after 2 weeks in vitro (not shown). The myotubes stained positively for desmin, demonstrated their muscle origin and the high purity of the culture (not shown). Isolated myoblasts were stained with anti-desmin antibodies and the staining was developed using fluorescence-labeling as described in Materials and Methods. Almost all the cells were stained positively for desmin. These results indicate that the myoblast isolation technique yielded a uniform population of cells with muscle characteristics.

Figure 5:
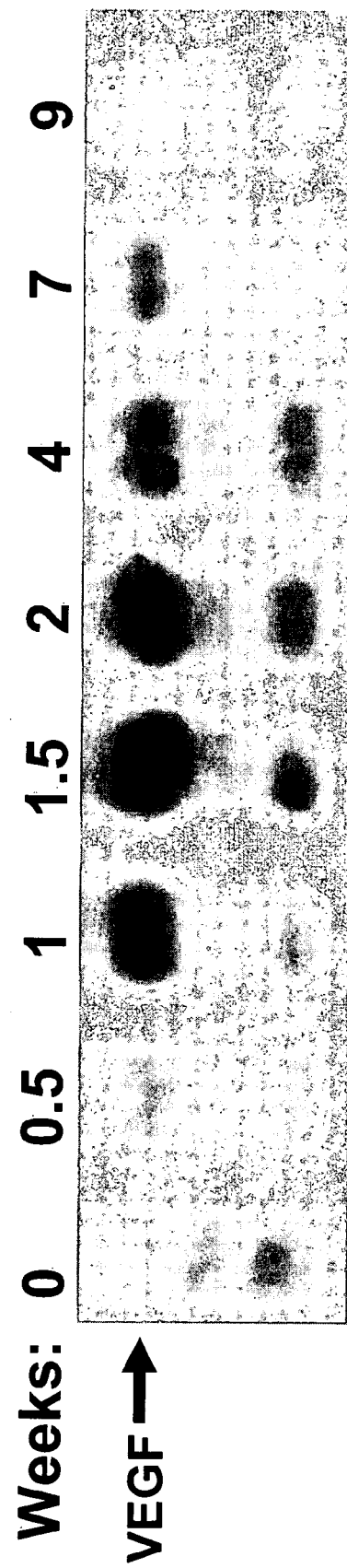
FIG. 5 is a Western blot showing VEGF protein expression in conditioned media at various time points collected from mouse myoblasts that were infected with AdVEGF and plated.

VEGF Protein Expression in Myoblast In Vitro:

In order to achieve the goal of large muscle tissue engineering, vascularization of the regenerating tissue is essential. To enhance neovascularization, myoblast were infected with an adenovirus vector encoding for mouse $VEGF_{165}$ under the regulation of the strong CMV promoter (AdVEGF). Conditioned media was collected from VEGF infected myoblasts at 4, 7 and 10 days and at 2, 4, 7, 9 weeks after infection. The presence of VEGF in conditioned media was determined by VEGF western blot analysis (FIG. 5). VEGF protein appeared as a 25 KDa immunoreactive band. VEGF expression was highest 1.5 weeks after infection. VEGF levels progressively increased during the first 10 days after infection and then gradually decreased until the $9^{th}$ week. Conditioned media collected after 10 weeks showed no detectable VEGF (not shown). These results indicate that myoblasts infected with AdVEGF secrete VEGF for a limited period of time that may be sufficient to support tissue vascularization following implantation.

Figure 4:
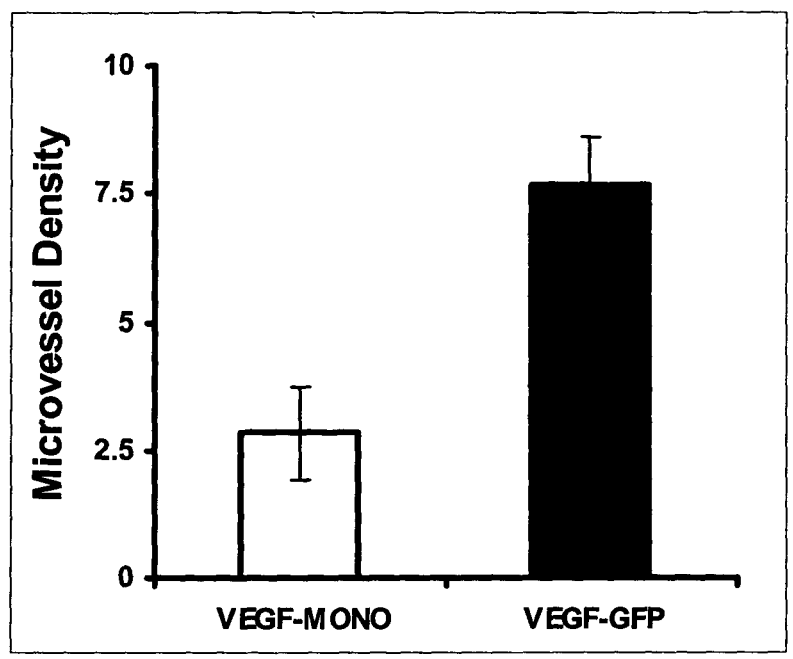
FIG. 4 is a bar graph showing microvessel density (C) of neovascularization of engineered muscle tissue, which was calculated by counting the number of capillaries in 8 high power fields in each section.
Figure 6:
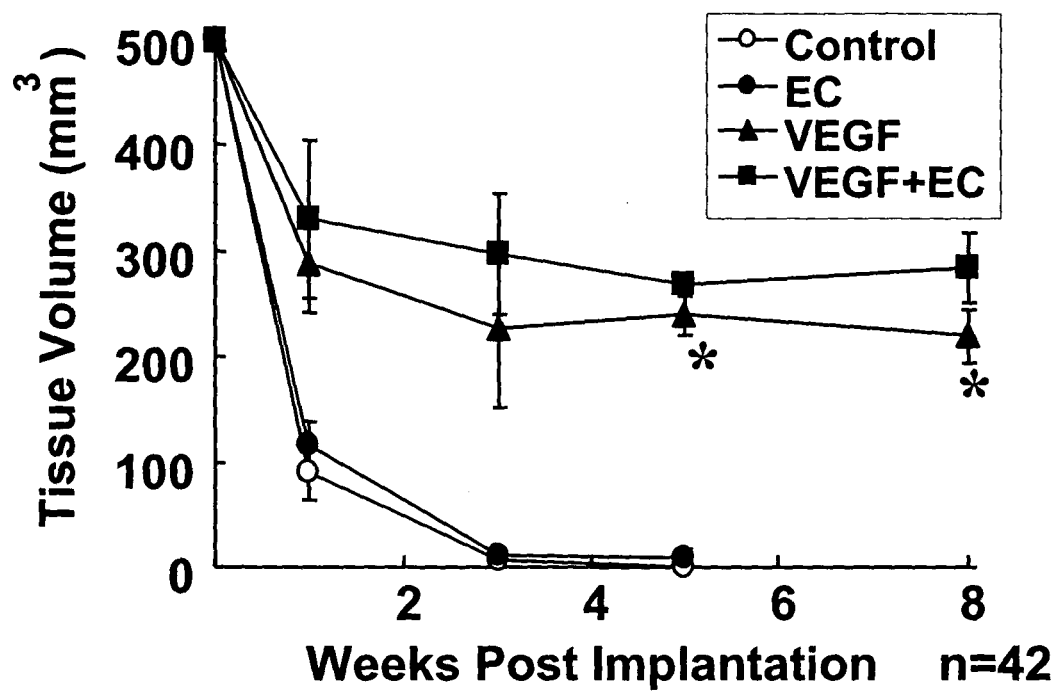
FIG. 6 is a graph showing formation of muscle tissue in vivo following injection of infected myoblasts and EC combinations with collagen gel into subcutaneous of nude mice.

In Vivo Muscle Tissue Engineering:

For an additional support for tissue neovascularization we investigated the incorporation of vascular EC into the engineered muscle tissue. In order to distinguish between the implanted and host EC we used human dermal capillary EC (HMEC-1) that were labeled by infection with an adenovirus vector encoding for β-galactosidase (AdLacZ). In vitro staining for LacZ expression, using X-gal staining, indicated that more than 95% of infected HMEC-1 expressed LacZ (not shown). VEGF expressing myoblasts in combination with LacZ expressing HMEC-1 were suspended in 0.5 ml collagen type I and injected subcutaneously to athymic mice. Four cell combinations were used: 1. VEGF-expressing myoblasts with LacZ expressing HMEC-1 (VEGF+EC). 2. VEGF-expressing myoblasts alone (VEGF). 3. LacZ expressing HMEC-1 and non-infected myoblasts (EC). 4. Non-infected myoblasts (Control). Three mice from each group were sacrificed after 1, 3, 5 and 8 weeks and tissue volumes were determined (FIG. 6). A macro view (not shown) of tissue formation was analyzed, under the mouse skin, 5 weeks after implantation. In control and EC groups the implanted tissues were mostly undetected and only a small scar was noted in some of the EC group. In contrast, bulky yellowish tissues were observed in VEGF and VEGF+EC groups that were surrounded by newly formed blood vessels. In addition dilation of the subcutaneous blood vessels could be seen in VEGF and VEGF+EC groups. The volumes of control and EC groups decreased by about 80% during the first week after implantation and continued to decrease until it was undetectable at 3 weeks after implantation (FIG. 6). The tissue volumes of VEGF+EC and VEGF groups decreased by about 40% during the first week after implantation and then remained without a significant change for additional 7 weeks. The size of engineered tissues was significantly larger in the VEGF+EC group than in the VEGF group only at 5 and 8 weeks after implantation (FIG. 4). These results indicate that VEGF supplementation to newly formed muscle tissues helps to maintain tissue volume. On the other hand, the addition of EC to the engineered muscle had no significant effect on the volumes of the tissue.

Neovascularization of Engineered Muscle Tissue:

Histological and immunohistochemical stainings were performed on the engineered tissues that were retrieved 5 weeks after implantation (not shown). H&E staining of control and EC groups indicated that a large proportion of the tissue consisted of extracellular matrix and the cells were scatter with no signs of organized tissue compared with higher cellularity and tissue organization in the VEGF and VEGF+EC groups (not shown). To analyze tissue vascularization, the newly formed tissues were stained with anti mouse CD31 antibodies (not shown). These antibodies are species-specific and detect only mouse EC within the engineered tissues but not the implanted HMEC-1. Only a few capillaries were detected in the control and EC groups whereas the VEGF and VEGF+EC groups showed intense neovascularization. In the VEGF+EC group some dilated vessels with a larger diameter could be observed, indicating of VEGF activity in the tissue. We next examined the presence of implanted HMEC-1 using X-gal staining that stains all cells that express LacZ in a blue color (not shown). There were no blue stained cells in the control and VEGF groups that did not receive HMEC-1 cells. Only few blue-stained EC were detected in the EC group. Although the number of implanted EC in the EC group was the same as in the VEGF+EC group, many blue stained EC were detected in the latter one. Some of the blue EC cells were associated with vascular structures (not shown). These results indicate that VEGF supplementation to the engineered tissue resulted in a massive neovascularization whereas implanted EC, although integrated in some of the capillaries, had no significant effect on tissue neovascularization. In addition, VEGF supplementation was required to preserve the implanted HMEC-1. These results support our observation of the effects of VEGF on tissue volume preservation (FIG. 6).

Figure 7:
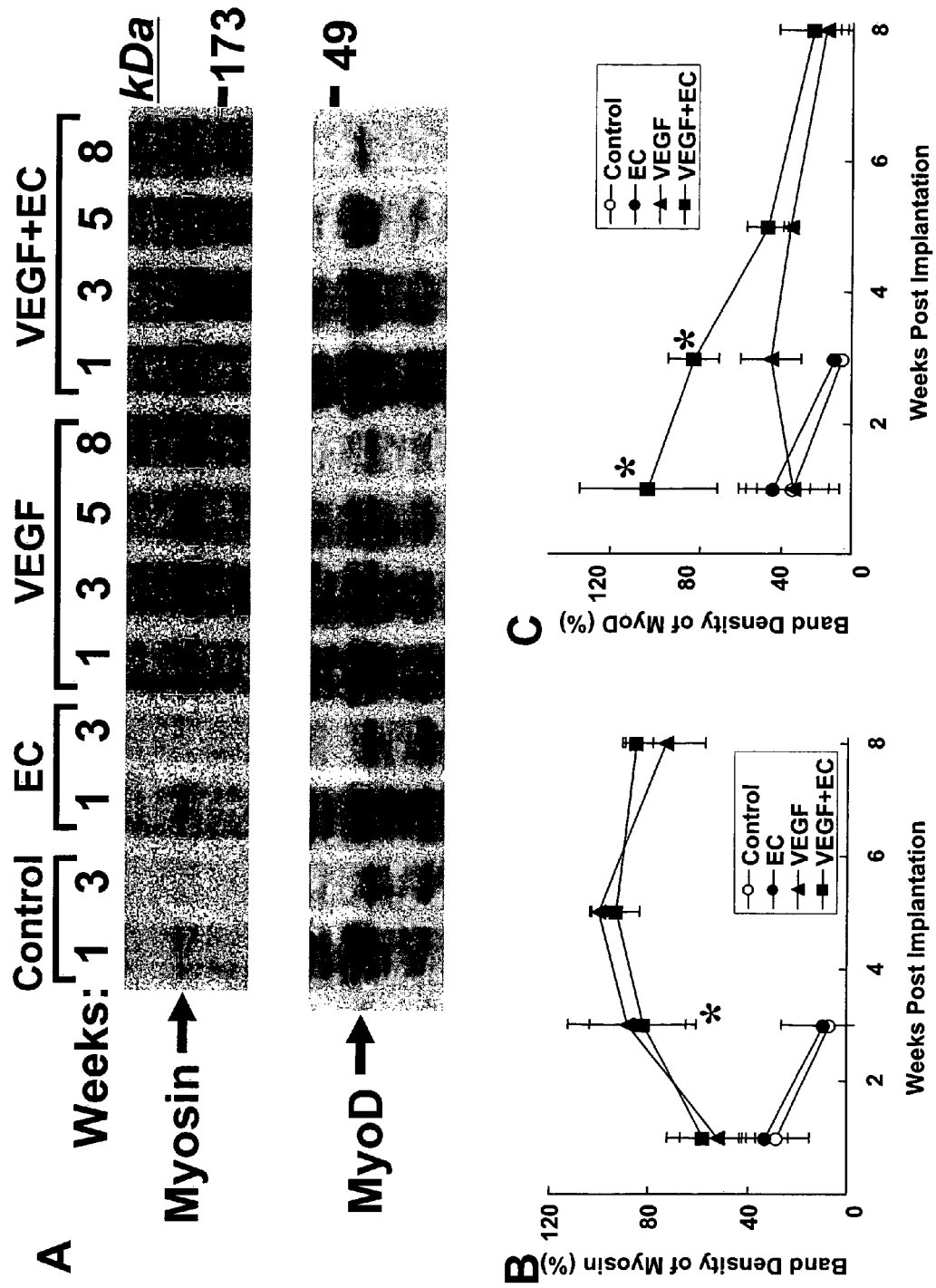
FIG. 7A is a Western blot showing expression of muscle specific proteins myosin and MyoD in engineered tissue in vivo following injection with infected myoblasts and EC combinations with collagen gel into subcutaneous of nude mice.
FIG. 7B is a graph of the densitometrical analysis of myosin expression in engineered tissue in vivo.
FIG. 7C is a graph of the densitometrical analysis of MyoD expression in engineered tissue in vivo.

Expression of Muscle Specific Proteins in Engineered Muscle Tissue:

Gross examination of the engineered tissues suggested that organized tissues were formed in the VEGF and VEGF+EC groups. In order to test if the implanted myoblasts formed muscle tissue in vivo we analyzed the expression of muscle specific genes in the newly formed tissues. The expression of skeletal muscle myosin heavy chain and of MyoD were examined using Western blot analysis (FIG. 5A). Control and EC groups showed Myosin and MyoD expression only in the first week after implantation whereas VEGF and VEGF+EC groups showed myosin expression for up to 8 weeks and MyoD expression for up to 5 weeks (FIG. 7A). We further analyzed myosin and MyoD expression by densitometry (FIG. 7B and FIG. 7C, respectively). The expression of myosin sharply decreased in the control and EC groups during the first 3 weeks after implantation and was undetectable after that. In contrast, myosin expression gradually increased in the VEGF and VEGF+EC groups during the first 5 weeks after implantation and was constant after that. MyoD expression pattern behaved similar to myosin expression in the control and EC groups. Although MyoD expression in the VEGF group, 1 week after implantation, was at the same level as in the control and EC groups, these levels were not significantly changed for up to 5 weeks and then gradually decreased. In contrast, MyoD expression in the VEGF+EC group was significantly higher than in the other groups during the first 3 weeks after implantation. MyoD expression in this group was progressively decreased and was similar to that of the VEGF group from week 5 to 8 after implantation. These results indicate that the engineered tissues have muscle properties that were maintained for at least 8 weeks in vivo. In addition, these results support the methods of the present invention by showing that VEGF helps to preserve the newly formed muscle tissue and suggesting that the presence of EC in the implanted tissue may have a role in muscle tissue formation.

Example 4

In Vitro Culture and Transfection of Human Skin-Derived Mesenchymal Cells with VEGF and GFP Expression Vectors To explore additional cell sources from human origin for microencapsulation, a method was developed to isolate mesenchymal cells (MC) from skin. Human skin biopsies were obtained and the dermal layers were isolated, sectioned into small pieces (1 mm$^3$) and digested with collagenase for 2 hours at 37° C. The cells were resuspended in culture medium and plated on non-treated petri dishes. Skin MC were maintained in culture for more than 50 passages. Microscopic image of human skin-derived mesenchymal cells showing elongated fibroblast-like cells. The cells were analyzed by immunostaining for CD90 (Thy-1) and CD105 (endoglin), markers usually associated with mesenchymal stem cells (not shown). Most cells stained positively for CD90 and CD105, confirming their mesenchymal origin (200× magnification). FACS analysis confirmed that the majority of the cells express CD90 (98.5%) or CD105 (85.7%). IgG-FITC sorting was used to determine non-specific background.

To test the feasibility of recombinant protein expression in the skin MC they were transfected with 2 different plasmids encoding for GFP, using LipofectAMINE PLUS™. The identification of transfected cells was done using fluorescent microscopy. Many cells per high power field showed green fluorescence, indicating positive transfection. No green cells could be observed in cells transfected with a similar plasmid that did not encode for GFP. These results indicate that MC can be retrieved from human skin, maintained in culture and are transfectable with plasmids.

Expression of GFP in transfected skin-derived mesenchymal cells Skin mesenchymal cells in a 6 well culture dish were transfected with 1 □g DNA of pIRES-GFP, pVEGF-GFP and pCDNA3 using LipofectAMINE PLUS™. Two days later cells were inspected by light and fluorescent microscopy and images were captured. Individual green fluorescent cells were observed only in cultures transfected with GFP encoding plasmids.

Example 5

In Vivo Transfection of VEGF$_{165}$ cDNA Improves Wound Healing in Diabetic Mice Wound healing is impaired in diabetic patients in part because of inadequate angiogenesis. We studied the effects of delivering VEGF cDNA to the wound site in order to provide constant production of the protein and enhance angiogenesis. For these experiments we used genetically healing-impaired diabetic mice (C57BL/KsJ db/db, Jackson laboratories, Bar Harbor Me.). These mice were previously shown to exhibit several characteristics of adult onset diabetes, including obesity and markedly delayed wound closure. Mice were anesthetized and their back was carefully shaved and washed with sterile water. Using a 1×1 cm template, full thickness skin wounds were created with a surgical scalpel (one wound/mouse). Plasmid DNA (100 μg) encoding for hVEGF165 under the strong CMV promoter (pCMV-VEGF) was applied topically to the left side of the back and ultrasound energy (1 MHz, 2 w/cm$^2$, 20% pulsatile mode) was applied for 20 minutes. At the end of the ultrasound application, the skin was cleansed and washed with water to remove any residual plasmid DNA. All wounds were covered with a transparent dressing (Bioclusive Select, Johnson & Johnson; Skipton, UK) to prevent loss of fluids and possible infection. Control treatments included nontreated wounds, transfection without DNA and VEGF plasmid alone. Measurements of the wound size were performed on day 0, one, and every two days for up to 12 days. The wound edges were measured using a caliper, and by placing a transparency on the wound and marking the wound margins. The wound areas were assessed using image analysis software. Wound closure using both measuring techniques was calculated as follows: Percent closed=[(area on day 0-open area on day X)/area on day 0]×100.

Figure 8:
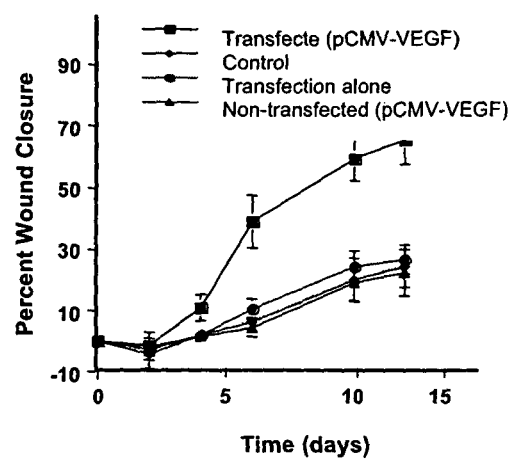
FIG. 8 is a graph showing percent wound closure in diabetic mice post transfection with a hVEGF cDNA plasmid.

Mice transfected with pCMV-VEGF showed a significant acceleration of wound closure when compared to control treatments (FIG. 8). By day 12 after treatment, mice treated with VEGF transfection had approximately 65% of these wounds closed compared with 20% in the control treatments. Gross examination of the VEGF transfected mice showed the presence of erythema at days 4 to 6, which was not seen in the control groups (not shown). At day six, thick granulation tissue was observed in the transfected group, covering large areas of the wounds, whereas the control groups did not show any granular tissue. Immunohistochemical staining for newly formed capillaries, using anti-PECAM (CD31) antibodies revealed the generation of newly formed capillaries as early as 6 days post wounding in the VEGF transfected group (not shown) but not in non-treated wounds. At day 12 post treatment, vigorous neovascularization was observed in the entire wound harvested from the VEGF transfected wounds, whereas only a few vessels were seen in the non-treated wounds and none in the skin adjacent to the wounds. Each group consisted of 6-9 mice and standard deviations were calculated. Representative pictures of wounds (not shown) were taken at days 0 (I), 6 (II and IV) and 12 (III and V) post wounding from non treated mice (IV and V) and mice transfected with VEGF165 cDNA (II and III).

Wound tissue was harvested on day 6 and 12 post wounding from wounds treated with VEGF transfection and non treated wounds. Skin adjacent to the wound was harvested 12 days post wounding from treated and non-treated wounds. Sections were immunostained with anti-CD-31 antibodies and photographed at 250× magnification.

Figure 9:
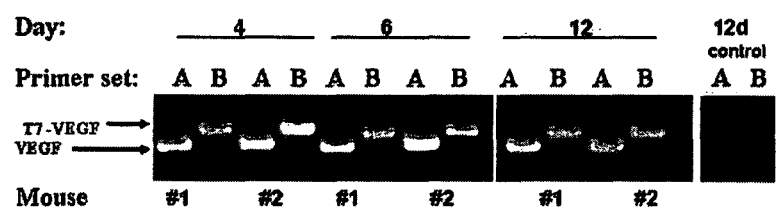
FIG. 9 shows elevated levels of hVEGF transcript following hVEGF cDNA transfection into skin.

In order to verify that the enhanced wound neovascularization was the result of VEGF transcription from the transfected plasmid we used 2 different sets of PCR primers. The first set (A) was derived from the N and C-termini of VEGF165 cDNA sequence. The second set (B) had the same reverse primer that was derived from the C-terminus of hVEGF sequence but the forward primer was derived from a T7 promoter sequence, located between the CMV promotet and the hVEGF sequence, which is present only in the plasmid-derived hVEGF transcripts. A strong amplified VEGF DNA could be detected using set A, in two representative mice analyzed at 4, 6 and 12 days post transfection (FIG. 9). Skin samples adjacent to the wounds were harvested from mice treated with VEGF ultrasound on days 4, 6 and 12 after wounding and from nontreated mouse. Total RNA was prepared and used for RT-PCR analysis, using two sets of primers, as described above. The corresponding size of the amplified DNA product using the natural VEGF set (A) is 580 bp for VEGF165 and 610 bp using the T7-VEGF set (B). The size of the amplified DNA was approximately 650 bp, in agreement with the expected size of the VEGF 165 transcript. In addition, a larger DNA product was detected in these mice and the size difference between the two DNA products was about 30 bp longer, consistent with the location of the T7 promoter upstream of the VEGF cDNA. In contrast, a sample derived from the skin of a mouse from the control group yielded a relatively low intensity VEGF amplified DNA product, only with the first primer set that detects the natural VEGF transcripts, but not with the T7-VEGF set. These results indicated that the majority of the VEGF in the skin of mice was a result of hVEGF cDNA transfection.

Taken together, these results indicate that secretion of the VEGF protein through hVEGF165 cDNA transfection to the skin of diabetic mice results in abundant VEGF expression that leads to increased neovascularization and enhanced wound closure. In another embodiment, a novel system of encapsulated VEGF transfected cells is disclosed that can be applied topically to the wound region, thus avoiding direct gene delivery in the in vivo setting.

Example 6

Neovascularization of a Urinary Organ Structure Using VEGF

I. Isolation of Kidney Cells.

Small kidneys, for example, from one week old C7 black mice, were decapsulated, dissected, minced and suspended in Dulbecco's Modified Eagles's Medium (DMEM; Sigma, St. Louis, Mo.) containing 15 mM Hepes, pH 7.4 and 0.5 µg/ml insulin, 1.0 mg/ml collagenase and 0.5 mg/ml dispase, a neutral protease from *Bacillus polymyxal* (Boehringer Mannheim, Indianapolis, Ind.).

Large kidneys, for example, swine kidneys, were arterially perfused at 37° C. for 10 minutes with calcium free Eagles minimum essential medium within three hours of extraction. The kidneys were then perfused with 0.5 mg/ml collagenase (Type IV, Sigma, St. Louis, Mo.) in the same buffer supplemented with 1.5 mM $MgCl_2$ and 1.5 mM $CaCl_2$. The kidneys were then decapsulated, dissected, minced and suspended in Dulbecco's Modified Eagles's Medium (DMEM; Sigma, St. Louis, Mo.) containing 15 mM Hepes, pH 7.4 and 0.5 µg/ml insulin, 1.0 mg/ml collagenase and 0.5 mg/ml dispase, a neutral protease from *Bacillus polymyxal* (Boehringer Mannheim, Indianapolis, Ind.).

The kidney cell suspension, from either large or small kidneys, was gently agitated in a water bath for 30 minutes at 37° C. The cells and fragments were recovered by centrifugation at 50 g for five minutes. The pellets were resuspended in DMEM containing 10% fetal bovine serum (Biowhittaker, Walkersville, Md.) to stop proteolysis, and the turbid solution was passed through sterile 80 mesh nylon screens to eliminate large fragments. The cells were recovered by centrifugation and washed twice with calcium free Dulbecco's Modified Eagles's Medium.

II. In Vitro Culturing of Kidney Cells.
Isolation of Rat Tail Collagen:

Tendon was stripped from rat tails and stored in 0.12 M acetic acid in deionized water in 50 ml tubes. After 16 hours at 4° C. overnight.

Dialysis bags were pretreated to ensure a uniform pore size and removal of heavy metals. Briefly, the dialysis bag is submerged in a solution of 2% sodium bicarbonate and 0.05% EDTA and boiled for ten minutes. Multiple rinses of distilled water was used to remove the sodium bicarbonate and 0.05% EDTA.

The 0.12 M acetic acid solution comprising rat tendons was placed in treated dialysis bags and dialyzed for two or three days to remove acetic acid. The dialysis solution was changed every 3 to 4 hours.
Coating Tissue Culture Plates:

The culture flasks, 75 $cm^2$, were coated with a solution containing about 30 µg/ml collagen (Vitrogen or rat tail collagen), about 10 µg/ml human fibronectin (Sigma, St. Louis, Mo.) and about 10 µg/ml bovine serum albumin (Sigma, St. Louis, Mo.) in a total volume of about 2 ml of supplemented medium by incubation at 37° C. for 3 hours.
Cell Culture:

Digested single suspended renal cells were plated on, a modified collagen matrix at a concentration of about $1 \times 10^6$ cells/ml and grown in DMEM supplemented with about 10% fetal bovine serum, about 5 µg/ml bovine insulin, about 10 µg/ml transferrin, about 10 µg/ml sodium selenite, about 0.5 µM hydrocortisone, about 10 ng/ml prostaglandin $E_2$, about 100 units/ml penicillin G, about 100 µg/ml streptomycin (Sigma, St. Louis, Mo.) in a 5% $CO_2$ incubator at about 37° C.

Confluent monolayers, were subcultured by treatment with about 0.05% trypsin, about 0.53 mM EDTA (Gibco BRL, Grand Island, N.Y.) in calcium ion free phosphate buffer saline (PBS) (about 1.51 mM $KH_2PO_4$, about 155.17 mM NaCl, about 2.8 mM $Na_2HPO.7H_2O$). Cells may be cultured any time from the first passage by suspension in about 10% DMSO in culture medium for freezing and storage in liquid medium.

III. Isolation and Culturing of Endothelial Cells.

Endothelial cells, were isolated from a dissected vein. Perivenous heparin/papaverine solution (3 mg papaverine HCl diluted in 25 ml Hanks balanced salt solution (HBSS) containing 100 units of heparin (final conc. 4 µ/ml)), was used to improve endothelial cell preservation. A proximal silk loop was placed around the vein and secured with a tie. A small venotomy was made proximal to the tie and the tip of vein cannula was inserted and secured in place with a second tie. A second small venotomy was made beyond the proximal tie and the vein was gently flushed with Medium 199/heparin solution Medium 199 (M-199) supplemented with 20% fetal bovine serum, ECGF (100 mg/ml), L-glutamine, heparin (Sigma, 17.5 µ/ml) and antibiotic-antimycotic), to remove blood and blood clots. Approximately 1 ml of a collagenase solution (0.2% Worthington type I collagenase dissolved in 98 ml of M-199, 1 ml of FBS, 1 ml of PSF, at 37° C. for 15-30 min, and filter sterilized), was used to flush through the dissected vein. The collagenase solution was also used to gently distend the vein and the distended vein was placed into 50 ml tube containing Hank's Balanced Salt Solution (HBSS). The tube containing the collagenase distended vein was incubated for 12 minutes at 37° C. to digest the inner lining of the vein. After digestion, the contents of the vein, which contain the endothelial cells, were removed into a sterile 15 ml tube. The endothelial cell suspension was centrifuged at 125× g for 10 minutes. Endothelial cells were resuspended in 2 ml of Dulbecco.'s Modified Eagle Media with 10% FBS and penicillin/streptomycin (DMEM/10% FBS) and plated into a 24 well plate coated with 1% difcogelatin. The endothelial cells were incubated overnight at 37° C.

After overnight incubation, the cells were rinsed with HBSS and placed in 1 ml of fresh DMEM/10% FBS. The media was changed 3 times a week. When cultures reached confluence (after 3-7 days), the confluent monolayers were subcultured by treatment with 0.05% trypsin, 0.53 mM EDTA, for 3-5 min until the cells dispersed. The dispersed cells were plated onto culture dishes coated with 0.1% difcogelatin at a 1:4-1:6 split ratio. The endothelial cells were expanded until sufficient cell quantities were achieved. Cells were trypsinized, collected, washed and counted for seeding.
IV. Isolation and Culturing of Urothelial and Smooth Muscle Cells.

The harvested cells were cultured according to previously published protocols of Atala et al., (1993) *J. Urol.* 150: 608, Cilento et al., (1994) *J. Urol.* 152: 655, Fauza et al., (1998) *J. Ped. Surg,* 33, 7-12, which are herein specifically incorporated by reference.

Culturing Urothelial Cell Populations:

A bladder specimen was obtained and prepared for culturing. To minimize cellular injury, the specimen was sharply excised rather than cut with an elecrocautery. The serosal surface was marked with a suture to ensure there will be no ambiguity as to which side represented the urothelial surface.

The specimen was processed in laminar flow cell culture hood, using sterile instruments. Culture medium with Keratinocyte-SFM (GIBCO BRL (Cat. No. 17005), with Bovine Pituitary Extract (Cat. No. 13028, 25 mg/500 ml medium) and Recombinant Epidermal Growth Factor (Cat. No. 13029, 2.5 µg/500 ml medium) as supplement was prepared. 10 ml of culture medium at 4° C., was placed in each of two 10 cm cell culture dishes, and 3.5 ml in a third dish. Blood was removed from the specimen by placing the specimen in the first dish and gently agitating it back and forth. The process was repeated in the second dish, and finally the specimen was transferred to the third dish. The urothelial surface was gently scraped with a No. 10 scalpel blade without cutting into the specimen. The urothelial cells were visible as tiny opaque material dispersing into the medium. The urothelial cell/medium suspension was aspirated and seeded into six wells of a 24-well cell culture plate with approximately 0.5 to 1 ml of medium to each well to give a total of 1 to 1.5 ml per well. The cells were incubated at 37° C. with 5% $CO_2$.

The following day (Day 1 post harvesting), the medium was aspirated from the six wells and fresh medium applied. the cells were centrifuged at 1000 rpm for 4 minutes and the supernatant was removed. The cells were resuspended in 3 to 4.5 ml of fresh medium warmed to 37° C. in a 24-well plate.

The culture medium was removed and PBS/EDTA (37° C., pH 7.2, 0.53 mM EDTA (0.53 ml of 0.5 M EDTA, pH 8.0, in each 500 ml of PBS)), was added to each 24-well plate well, or 10 ml to each 10 cm dish. The cells were then passaged in two 10 cm dishes. Hereafter the cells were passaged whenever they reached 80 to 90% confluence, without allowing the cells to reach 100% confluence.

The cells were observed under a phase contrast microscope. When the cell-cell junctions were separated for the majority of the cells (approximately 5 to 15 minutes), the PBS/EDTA was removed and 300 µl Trypsin/EDTA (37° C., GIBCO BRL, Cat. No. 25300-054), was added to each 24-well plate well or, 7 ml to each 10 cm dish. The plate/dish was periodically agitated. When 80 to 90% of the cells detached from the plate and started to float (approximately 3 to 10 minutes), the action of the Trypsin was inhibited by adding 30 µl soy bean Trypsin inhibitor (GIBCO BRL, Cat. No. 17075-029, 294 mg of inhibitor to 20 ml PBS), to each 24-well place well or 700 µl to each 10 cm dish to stop the action of the EDTA. 0.5 ml culture medium was added to each 24-well plate well or 3 ml culture medium was added to each 10 cm dish. The PBS/EDTA and Trypsin/EDTA incubations were performed at room temperature, but were more effective if the plates were incubated at 37° C.

The cells were harvested by centrifugation at 1000 rpm for 4 minutes, and the supernatant removed. The cells were resuspended in 5 ml culture medium, and the number of cells was determined using a hemocytometer. Cell viability was determined by the standard Trypan blue stain test. The optimal seeding density for a 100 mm culture plate was approximately $1 \times 10^6$ cells/plate. The desired number of cells was aliquoted into the dish and the volume of a medium was added to a total of approximately 10 µl/plate.

Culturing Bladder Smooth Muscle Cells:

After removing the urothelial cell layer from the bladder specimen as described inabove, the remaining muscle was dissected into 2-3 mm muscle segments. Each muscle segment was spaced evenly onto a 100 mm cell culture dish. The muscle segments were dried and allowed to adhere to the dish (approximately 10 minutes). 20 ml of Dulbecco's Modified Eagle Media with 10% FCS was added to the dried muscle segments. The muscle segments were incubated for 5 days undisturbed at 37° C. with 5% $CO_2$. The culture media was changed on the 6th day and any non-adherent segments were removed. The remaining segments were cultured for a total of 10 days, after which all the muscle segments were removed. The cells from the muscle segments that had adhered to the dish were incubated until small islands of cells appeared. These cells were trypsinized, counted and seeded into a T75 culture flask.

The cells were fed every 3 days depending on the cell density, and the cells were passaged when they reached 80-90% confluence.

The cells can be transfected with a plasmid encoding $VEGF_{165}$ or with a plasmid encoding monomeric VEGF ($VEGF^{mono}$). Alternatively, the cells can be transfected with other growth factors according to the methods of this invention.

V. Preparation of a Decellularized Organs, or Parts of Organs.

The following method describes a process for removing the entire cellular content of an organ or tissue without destroying the complex three-dimensional infra-structure of the organ or tissue. A kidney, was surgically removed from a C7 black mouse using standard techniques for tissue removal. The kidney was placed in a flask containing a suitable volume of distilled water to cover the isolated kidney. A magnetic stir plate and magnetic stirrer were used to rotate the isolated kidney in the distilled water at a suitable speed for 24-48 hours at 4° C. This process removes the cellular debris and cell membrane surrounding the isolated kidney.

After this first removal step, the distilled water was replaced with a 0.05% ammonium hydroxide solution containing 0.5% Triton X-100. The kidney was rotated in this solution for 72 hours at 4° C. using a magnetic stir plate and magnetic stirrer. This alkaline solution solubilized the nuclear and cytoplasmic components of the isolated kidney. The detergent Triton X-100, was used to remove the nuclear components of the kidney, while the ammonium hydroxide solution was used to lyse the cell membrane and cytoplasmic proteins of the isolated kidney.

The isolated kidney was then washed with distilled water for 24-48 hours at 4° C. using a magnetic stir plate and magnetic stirrer. After this washing step, removal of cellular components from the isolated was confirmed by histological analysis of a small piece of the kidney. If necessary, the isolated kidney was again treated with the ammonium hydroxide solution containing Triton X-100 until the entire cellular content of the isolated kidney was removed. After removal of the solubilized components, a collagenous three-dimensional framework in the shape of the isolated kidney was produced.

This decellularized kidney was equilibrated with 1× phosphate buffer solution (PBS) by rotating the decellularized kidney overnight at 4° C. using a magnetic stir plate and magnetic stirrer. After equilibration, the decellularized kidney was lyophilized overnight under vacuum. The lyophilized kidney was sterilized for 72 hours using ethylene oxide gas. After sterilization, the decellularized kidney was either used immediately, or stored at 4° C. or at room temperature until required. Stored organs were equilibrated in the tissue culture medium overnight at 4° C. prior to seeding with cultured cells.

VI. Preparation of a Kidney Augmenting Organ Structure.

This example describes the preparation of wafers for implantation into one or more regions of an organ, e.g., a kidney. In one example, renal cells transfected with VEGF can be used. In another example, encapsulated cells that have been transfected with VEGF can be places at the site of implantation. The size and configuration of the renal tissue matrix (wafer) for placing in the kidney parenchyma is determined. For example, a matrix about 1 mm thick, that is about 2 cm in length and width. Single suspended renal cells are seeded on kidney tissue matrix at a concentration of about cells $10 \times 10^6$ cells cm$^3$. The cells were allowed to attach onto the matrix wall for about 2 hours at 37° C. The matrix was then turned over to the opposite side and single suspended renal cells were seeded on kidney tissue matrix. The cells were allowed to attach onto the matrix wall for about 2 hours at 37° C. After incubation is completed, culture medium was slowly added to the flask to cover the entire renal matrix. Care was taken not to disturb the cells within the matrix. The matrix was incubated at 37° C. in an incubator with $CO_2$. The culture medium was changed daily, or more frequently, depending on the level of lactic acid produced. On day 4 after the initial seeding, the cell-matrix system was placed in a rotating bioreactor system for additional 3 days in order to achieve uniform cell distribution and growth.

VII. Implantation of the Kidney Augmenting Organ Structure.

The kidney augmenting organ wafers were placed into one or more region of the organ, e.g., a kidney. The surface of the recipient kidney was exposed. Renal vessels were clamped temporarily with vascular clamp in order to minimize bleeding. An incision was made on the kidney capsule for accessing the renal parenchyma. The capsule should be carefully pushed away from the parenchyma. The kidney parenchymal tissue similar in size and shape of the renal tissue matrix was removed without disrupting the collecting system during the removal. The cell-seeded renal tissue matrix was placed in the renal parenchyma and the kidney capsule was sutured over the implanted renal tissue matrix. The vascular clamp was removed for recirculation. Hemostasis was achieved by a gentle compression over the implants for a few minutes. After hemostatis, the wound was closed.

Following implantation, the growth and development of the cells in the kidney augmenting organ structures was examined. A photograph of renal biomatrices one week after implantation shows that the cells are cell viable and test positive with a lipophilic red fluorescent tracer, carbocyanine at ×100 magnification (Photograph not shown). Four weeks after implantation, the formation of tubular and glomerular-like structures is seen (H&E ×200, photographs not shown). The development of these tubular structures continues at week 8 post-implantation (photograph not shown). Histological and immunohistochemical stainings can be performed on the engineered tissues to compare vascularization, cellularity and tissue organization between VEGF treated, VEGF+EC, and control groups. VEGF supplementation to the engineered tissue can greatly enhance neovascularization and improve volume preservation.

The invention claimed is:

1. A method for augmenting organ function comprising:
   transiently transfecting a first population of cells with a plasmid encoding an angiogenesis modulating agent;
   culturing at least a second population of cells on a matrix material to produce an organ construct, wherein the second population of cells comprises cells of a different cell type than the first population; and
   implanting the organ construct and the first population of cells in vivo at a target site to replace or augment organ function, such that the first population of cells express the angiogenesis modulating agent thereby inducing the second population of cells to assimilate and differentiate at the target site.

2. The method of claim 1, wherein the matrix is decellularized tissue.

3. The method of claim 1, wherein the matrix is a hydrogel.

4. The method of claim 1, Wherein the matrix is a polymer.

5. The method of claim 1, Wherein the angiogenesis modulating agent is VEGF.

6. The method of claim 1, wherein the method further comprises assimilating the first population of cells into a tissue layer.

7. The method of claim 1, wherein the step of transiently transfecting the first population of cells further comprises:
   encapsulating the transfected first population of cells and
   implanting the organ construct and the encapsulated first population of cells in vivo at the target site to replace or augment organ function such that the first population of cells express the angiogenesis modulating agent and the second population of cells assimilate and differentiate at the target site.

8. The method of claim 7, wherein the step of encapsulating the transfected first population of cells further comprises using microspheres.

9. The method of claim 7, wherein the step of encapsulating the transfected first population of cells further comprises using alginate-PLL capsules.

10. The method of claim 1, wherein the first population of cells comprises endothelial progenitor cells.

11. The method of claim 1, wherein the first population of cells comprises vascular endothelial cells (EC).

12. The method of claim 1, wherein the first population of cells comprises myoblasts.

13. The method of claim 1, wherein the second population of cells comprises endothelial progenitor cells.

14. The method of claim 1, wherein the second population of cells comprises myoblasts.

15. A method of organ augmentation comprising the steps of:
   transiently transfecting a first population of cells with a plasmid encoding the angiogenesis modulating agent VEGF;
   selecting a second population of cells to be assimilated at a target tissue region upon implantation,
   suspending the first population of cells and the second population of cells in an injectable polymer matrix;
   injecting the first population of cells and the second population of cells and the polymer matrix into the target tissue region where the first population of cells will express the VEGF angiogenesis modulating agent, thereby inducing assimilation and differentiation of the second population of cells in the target region and augmenting organ function.

16. The method of claim 15, wherein the polymer matrix comprises collagen.

17. The method of claim 16, wherein the polymer matrix comprises collagen type I.

18. The method of claim 1, wherein the step of transiently transfecting the first population of cells further comprises:
encapsulating the transfected first population of cells;
suspending the encapsulated first population of cells and the second population of cells in an injectable polymer matrix
injecting the encapsulated first population of cells and the second population of cells and the polymer matrix into the target tissue region where the encapsulated first population of cells will express the VEGF angiogenesis modulating agent, thereby inducing assimilation and differentiation of the second population of cells in the target region and augmenting organ function.

19. The method of claim 18, wherein the step of encapsulating the transfected first population of cells further comprises using microspheres.

20. The method of claim 18, wherein the step of encapsulating the transfected first population of cells further comprises using alginate-PLL capsules.

21. The method of claim 15, wherein the step of transfecting the first population of cells comprises transiently transfecting the cells such that the angiogenesis modulating agent is produced for less than three weeks.

22. The method of claim 15, wherein the first population of cells comprises undifferentiated cells.

23. The method of claim 15, wherein the first population of cells comprises endothelial progenitor cells.

24. The method of claim 15, wherein the first population of cells comprises vascular endothelial cells (EC).

25. The method of claim 15, wherein the first population of cells comprises myoblasts.

26. The method of claim 15, wherein the second population of cells comprises endothelial progenitor cells (EPC).

27. The method of claim 1, wherein the second population of cells comprises myoblasts.

* * * * *

UNITED STATES PATENT AND TRADEMARK OFFICE
CERTIFICATE OF CORRECTION

| | | |
|---|---|---|
| PATENT NO. | : 8,940,292 B2 | Page 1 of 1 |
| APPLICATION NO. | : 10/766642 | |
| DATED | : January 27, 2015 | |
| INVENTOR(S) | : Anthony Atala et al. | |

It is certified that error appears in the above-identified patent and that said Letters Patent is hereby corrected as shown below:

Title page, item [75], line 2, inventor's name should read:

--[75] inventor: Shay Stoker--

Signed and Sealed this
Second Day of June, 2015

Michelle K. Lee
*Director of the United States Patent and Trademark Office*